United States Patent [19]

Bridges et al.

[11] Patent Number: 5,654,307
[45] Date of Patent: Aug. 5, 1997

[54] BICYCLIC COMPOUNDS CAPABLE OF INHIBITING TYROSINE KINASES OF THE EPIDERMAL GROWTH FACTOR RECEPTOR FAMILY

[75] Inventors: Alexander James Bridges, Saline, Mich.; William Alexander Denny, Pakuranga, New Zealand; David Fry, Ypsilanti, Mich.; Alan Kraker; Robert Frederick Meyer, both of Ann Arbor, Mich.; Gordon William Rewcastle, Manurewa; Andrew Mark Thompson, Mount Eden, both of New Zealand

[73] Assignee: Warner-Lambert Company, Morris Plains, N.J.

[21] Appl. No.: 358,351

[22] Filed: Dec. 23, 1994

Related U.S. Application Data

[63] Continuation-in-part of Ser. No. 186,735, Jan. 25, 1994, abandoned, and a continuation-in-part of Ser. No. 186,745, Jan. 24, 1994, abandoned.

[51] Int. Cl.$^6$ .................... A61K 31/505; C07D 239/70; C07D 487/00
[52] U.S. Cl. .................... 514/258; 544/253; 544/279
[58] Field of Search .................... 544/235, 253, 544/279; 514/258

[56] References Cited

U.S. PATENT DOCUMENTS

| 3,634,427 | 1/1972 | Schweizer et al. | 260/256.5 |
|---|---|---|---|
| 3,748,355 | 7/1973 | Bourgau et al. | 260/534 |
| 5,141,941 | 8/1992 | Fujii et al. | 514/256 |

FOREIGN PATENT DOCUMENTS

| 0404355 | 12/1990 | European Pat. Off. |
|---|---|---|
| 0414386 | 2/1991 | European Pat. Off. |
| 0537463 | 4/1993 | European Pat. Off. |
| 0602851 | 6/1994 | European Pat. Off. |
| 1934172 | 1/1970 | Germany |
| 2725019 | 12/1977 | Germany |
| 157280 | 5/1984 | India |
| 6041134 | 2/1994 | Japan |
| 6220059 | 8/1994 | Japan |
| 9307124 | 4/1993 | WIPO |
| 9413677 | 6/1994 | WIPO |
| 9421613 | 9/1994 | WIPO |

OTHER PUBLICATIONS

Registry No. 144511-63-7, Chem. Abstr., 1993.
Registry No. 144511-62-6, Chem. Abstr., 1993.
Registry No. 144511-49-9, Chem. Abstr., 1993.
Registry No. 144511-48-8, Chem. Abstr., 1993.
Registry No. 144511-45-5, Chem. Abstr., 1993.
Registry No. 144511-41-1, Chem. Abstr., 1993.
Registry No. 144511-40-0, Chem. Abstr., 1993.
Registry No. 142716-71-0, Chem. Abstr., 1993.
Registry No. 114984-45-1, Chem. Abstr., 1993.
Registry No. 111243-63-1, Chem. Abstr., 1993.
Registry No. 111218-85-0, Chem. Abstr., 1993.
Registry No. 111218-84-9, Chem. Abstr., 1993.
Registry No. 111218-82-7, Chem. Abstr., 1993.
Registry No. 111218-81-6, Chem. Abstr., 1993.
Registry No. 111218-79-2, Chem. Abstr., 1993.
Registry No. 111218-78-1, Chem. Abstr., 1993.
Registry No. 111218-77-0, Chem. Abstr., 1993.
Registry No. 108799-95-7, Chem. Abstr., 1993.
Registry No. 102932-27-4, Chem. Abstr., 1993.
Registry No. 99272-99-8, Chem. Abstr., 1993.
Registry No. 86414-79-1, Chem. Abstr., 1993.
Registry No. 65962-89-2, Chem. Abstr., 1993.
Registry No. 65962-88-1, Chem. Abstr., 1993.
Registry No. 152358-89-9, Chem. Abstr., 1993.
Registry No. 70026-96-9, Chem. Abstr., 1993.
Registry No. 105217-91-2, Chem. Abstr., 1993.
Registry No. 134999-86-3, Chem. Abstr.
Registry No. 105217-93-4, Chem. Abstr., 1993.
Registry No. 105217-92-3, Chem. Abstr., 1993.
Registry No. 135000-27-0, Chem. Abstr., 1993.
Registry No. 152358-87-7, Chem. Abstr., 1993.
Registry No. 101901-01-3, Chem. Abstr., 1993.
Registry No. 135034-87-6, Chem. Abstr., 1993.
Registry No. 152358-90-2, Chem. Abstr., 1993.
Registry No. 152358-86-6, Chem. Abstr., 1993.
Registry No. 134999-80-7, Chem. Abstr., 1993.
Registry No. 135000-29-2, Chem. Abstr., 1993.
Registry No. 152358-88-8, Chem. Abstr., 1993.
Registry No. 101900-99-6, Chem. Abstr., 1993.
Registry No. 134999-92-1, Chem. Abstr., 1993.
PCT International Search Report, PCT/US 94/00941, 1995.
Arzneim.–Forsch./Drug Res., vol. 39, No. 1, 1989, pp. 78–81, Hladon et al.
J. Am. Chem. Soc., vol. 82, 1960, pp. 5711–5718, Taylor et al.
Physiology and Biochemistry of Cytokinins in Plants, Symposium at Liblice, Czech, 1990, pp. 205–209, Nishikawa et al.
J. Med. Chem., vol. 26, No. 6, 1993, pp. 838–844, Iwamura et al.
Phytochemistry, vol. 18, 1979, pp. 217–222, Iwamura et al.
Chemical Abstracts, vol. 118, 1993, abstract No. 249833e.
Registry No. 144511-80-8, Chem. Abstr., 1993.
Registry No. 144511-78-4, Chem. Abstr., 1993.
Registry No. 144511-72-8, Chem. Abstr., 1993.
Registry No. 144511-66-0, Chem. Abstr., 1993.
Registry No. 144511-65-9, Chem. Abstr., 1993.
Registry No. 144511-64-8, Chem. Abstr., 1993.

Primary Examiner—Shean C. Wu
Attorney, Agent, or Firm—Francis J. Tinney

[57] ABSTRACT

Novel 4-substituted amino pyrido pyrimidine and 4-substituted amino pyrido pyrimidine inhibitors of epidermal growth factor receptor family of tyrosine kinase are described, as well as pharmaceutical compositions of the same, which are useful in treating proliferative diseases such as cancer, synovial pannus invasion in arthritis, psoriasis, vascular restenosis and angiogenesis and additionally useful in the treatment of pancreatitis and kidney disease as well as a contraceptive agent.

2 Claims, 17 Drawing Sheets

BICYCLIC COMPOUNDS CAPABLE OF INHIBITING TYROSINE KINASES OF THE EPIDERMAL GROWTH FACTOR RECEPTOR FAMILY

CROSS-REFERENCE TO RELATED APPLICATIONS

This application is a continuation-in-part of U.S. application Ser. No. 186,735, filed Jan. 25, 1994 and U.S. application Ser. No. 186,745, filed Jan. 24, 1994, both of which are hereby incorporated by reference both now abandoned.

TECHNICAL FIELD

The present invention relates to bicyclic heteroaromatic compounds which inhibit the epidermal growth factor receptor and related receptors and, in particular, their tyrosine kinase enzymic activity.

BACKGROUND ART

Cancer is generally a disease of the intracellular signalling system, or signal transduction mechanism. Cells receive instructions from many extracellular sources, instructing them to either proliferate or not to proliferate. The purpose of the signal transduction system is to receive these and other signals at the cell surface, get them into the cell, and then pass the signals on to the nucleus, the cytoskeleton, and transport and protein synthesis machinery. The most common cause of cancer is a series of defects, either in these proteins, when they are mutated, or in the regulation of the quantity of the protein in the cell such that it is over or under produced. Most often, there are key lesions in the cell which lead to a constitutive state whereby the cell nucleus receives a signal to proliferate, when this signal is not actually present. This can occur through a variety of mechanisms. Sometimes the cell may start to produce an authentic growth factor for its own receptors when it should not, the so-called autocrine loop mechanism. Mutations to the cell surface receptors, which usually signal into the cell by means of tyrosine kinases, can lead to activation of the kinase in the absence of ligand, and passing of a signal which is not really there. Alternatively, many surface kinases can be overexpressed on the cell surface leading to an inappropriately strong response to a weak signal. There are many levels inside the cell at which mutation or overexpression can lead to the same spurious signal arising in the cell, and there are many other kinds of signalling defect involved in cancer. This invention touches upon cancers which are driven by the three mechanisms just described, and which involve cell surface receptors of the epidermal growth factor receptor tyrosine kinase family (EGFR). This family consists of the EGF receptor (also known as Erb-B1), the Erb-B2 receptor, and its constituitively active oncoprotein mutant Neu, the Erb-B3 receptor and the Erb-B4 receptor. Additionally, other biological processes driven through members of the EGF family of receptors can also be treated by compounds of the invention described below.

The EGFR has as its two most important ligands Epidermal Growth Factor (EGF) and Transforming Growth Factor alpha (TGFalpha). The receptors appear to have only minor functions in adult humans, but are apparently implicated in the disease process of a large portion of all cancers, especially colon and breast cancer. The closely related Erb-B2 Erb-B3 and Erb-B4 receptors have a family of Heregulins as their major ligands, and receptor overexpression and mutation have been unequivocally demonstrated as the major risk factor in poor prognosis breast cancer. Additionally, it has been demonstrated that all four of the members of this family of receptors can form heterodimeric signalling complexes with other members of the family, and that this can lead to synergistic transforming capacity if more than one member of the family is overexpressed in a malignancy. Overexpression of more than one family member has been shown to be relatively common in human malignancies.

The proliferative skin disease psoriasis has no good cure at present. It is often treated by anticancer agents such as methotrexate, which have very serious side effects, and which are not very effective at the toxicity-limited doses which have to be used. It is believed that TGFalpha is the major growth factor overproduced in psoriasis, since 50% of transgenic mice which overexpress TGF alpha develop psoriasis. This suggests that a good inhibitor of EGFR signalling could be used as an antipsoriatic agent, preferably, but not necessarily, by topical dosing.

EGF is a potent mitogen for renal tubule cells. Fourfold increases in both EGF urinary secretion and EGF mRNA have been noted in mice with early stage streptozoicin-induced diabetes. In addition increased expression of the EGFR has been noted in patients with proliferative glomerulonephritis (Roychaudhury et al. *Pathology* 1993, 25, 327). The compounds of the current invention should be useful in treating both proliferative glomerulonephritis and diabetes-induced renal disease.

Chronic pancreatitis in patients has been reported to correlate with large increases in expression for both EGFR and TGF alpha. (Korc et al. *Gut* 1994, 35, 1468). In patients showing a more severe form of the disease, typified by an enlargement of the head of the pancreas, there was also shown to be overexpression of the erb-B2 receptor (Friess et al. *Ann. Surg.* 1994, 220, 183). The compounds of the current invention should prove useful in the treatment of pancreatitis.

In the processes of blastocyte maturation, blastocyte implantation into the uterine endometrium, and other peri-implantation events, uterine tissues produce EGF and TGF alpha (Taga *Nippon Sanka Fujinka Gakkai Zasshi* 1992, 44, 939), have elevated levels of EGFR (Brown et al. *Endocrinology*, 1989, 124, 2882), and may well be induced to produce heparin-binding EGF by the proximity of the developing, but not arrested, blastocyte (Das et al. *Development* 1994, 120, 1071). In turn the blastocyte has quite a high level of TGF alpha and EGFR expression (Adamson *Mol. Reprod. Dev.* 1990, 27, 16). Surgical removal of the submandibular glands, the major site of EGF secretion in the body, and treatment with anti-EGFR monoclonal antibodies both greatly reduce fertility in mice (Tsutsumi et al. *J. Endocrinology* 1993, 138, 437), by reducing successful blastocyte implantation. Therefore, compounds of the current invention should prove to have useful contraceptive properties.

PCT patent application Nos. WO92/07844 published May 14, 1992 and WO92/14716 published Sep. 3, 1992 describe 2,4-diaminoquinazoline as potentiators of chemotherapeutic agents in the treatment of cancer.

PCT published application No. WO92/20642 published Nov. 26, 1992 discloses bismono- and bicyclic aryl and heteroaryl compounds which inhibit EGF and/or PDGF receptor tyrosine kinase.

It is an object of the present invention to inhibit the mitogenic effects of epidermal growth factor utilizing an effective amount of bicyclic pyrimidine derivatives, in particular fused heterocyclic pyrimidine derivatives.

It is another object of the present invention to describe bicyclic pyrimidine derivatives, in particular fused heterocyclic pyrimidine derivatives, as inhibitors of the EGF, Erb-B2 and Erb-B4 receptor tyrosine kinases.

It is yet another object of the present invention to describe bicyclic pyrimidine derivatives, in particular fused heterocyclic pyrimidine derivatives, that are useful at low dosages as inhibitors of EGF-induced mitogenesis. This therefore leads to a further object of compounds having extremely low cytotoxicity.

It is a further object of the present invention to describe bicyclic pyrimidine derivatives, in particular fused heterocyclic pyrimidine derivatives, that are useful in suppressing tumors, especially breast cancers, where mitogenesis is heavily driven by EGFR family members.

It is another object of the present invention to describe bicyclic pyrimidine derivatives, in particular fused heterocyclic pyrimidine derivatives, that have utility as chronic therapy as inhibitors of EGF-induced responses.

It is another object of the current invention to describe bicyclic pyrimidine derivatives, in particular fused heterocyclic pyrimidine derivatives, that have utility as therapeutic agents against proliferative overgrowth diseases, including but not limited to, synovial pannus invasion in arthritis, vascular restenosis, psoriasis and angiogenesis. The compounds disclosed herein also are useful to treat pancreatitis and kidney disease and as a contraceptive agent.

SUMMARY OF THE INVENTION

Described is a method to inhibit epidermal growth factor by treating, with an effective inhibiting amount, a mammal, in need thereof, a compound of Formula I:

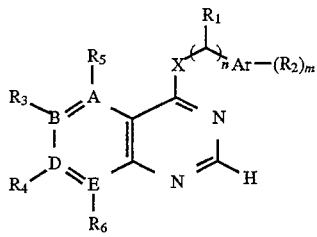

Formula I wherein at least one, and as many as three of A–E are nitrogen, with the remaining atom(s) carbon, or any two contiguous positions in A–E taken together can be a single heteroatom, N, O or S, in which case one of the two remaining atoms must be carbon, and the other can be either carbon or nitrogen;

X=O, S, NH or $NR^7$, such that $R^7$=lower alkyl (1–4 carbon atoms), OH, $NH_2$, lower alkoxy (1–4 carbon atoms) or lower monoalkylamino (1–4 carbon atoms);

n=0, 1, 2;

$R^1$=H or lower alkyl (1–4 carbon atoms); if n=2, $R^1$ can be independently H or lower alkyl (1–4 carbon atoms) on either linking carbon atom;

$R^2$ is lower alkyl (1–4 carbon atoms), cycloalkyl (3–8 carbon atoms), lower alkoxy (1–4 carbon atoms), cycloalkoxy (3–8 carbon atoms), nitro, halo (fluoro, chloro, bromo, iodo), lower perfluoroalkyl (1–4 carbon atoms), hydroxy, lower acyloxy (1–4 carbon atoms; —O—C(O)R), amino, lower mono or dialkylamino (1–4 carbon atoms), lower mono or dicycloalkylamino (3–8 carbon atoms), hydroxymethyl, lower acyl (1–4 carbon atoms; —C(O)R), cyano, lower thioalkyl (1–4 carbon atoms), lower sulfinylalkyl (1–4 carbon atoms), lower sulfonylalkyl (1–4 carbon atoms), thiocycloalkyl (3–8 carbon atoms), sulfinylcycloalkyl (3–8 carbon atoms), sulfonylcycloalkyl (3–8 carbon atoms), sulfonamido, lower mono or dialkylsulfonamido (1–4 carbon atoms), mono or dicycloalkylsulfonamido (3–8 carbon atoms), mercapto, carboxy, carboxamido (—C(O)—$NH_2$), lower mono or dialkylcarboxamido (1–4 carbon atoms), mono or dicycloalkylcarboxamido (3–8 carbon atoms), lower alkoxycarbonyl (1–4 carbon atoms), cycloalkoxycarbonyl (3–8 carbon atoms), lower alkenyl (2–4 carbon atoms), cycloalkenyl (4–8 carbon atoms), lower alkynyl (2–4 carbon atoms), or two $R^2$ taken together on contiguous carbon atoms can form a carbocyclic ring of 5–7 members or a monounsaturated 1,3-dioxolanyl, 1,4-dioxanyl, 1,4-dioxepinyl, pyranyl, furanyl, pyrrolidyl, piperidinyl, thiolanyl, oxazolanyl, thiazolanyl, diazolanyl, piperazinyl, morpholino or thiomorpholino ring; and m=0–3, wherein Ar is phenyl, thienyl, furanyl, pyrrolyl, pyridyl, pyrimidyl, imidazoyl, pyrazinyl, oxazolyl, thiazolyl, naphthyl, benzothienyl, benzofuranyl, indolyl, quinorinyl, isoquinolinyl and quinazolinyl;

$R^3$, $R^4$, $R^5$ and $R^6$ are independently, (not present), H, lower alkyl (1–4 carbon atoms), cycloalkyl (3–8 carbon atoms), lower alkoxy (1–4 carbon atoms), cycloalkoxy (3–8 carbon atoms), hydroxy, lower acyloxy (1–4 carbon atoms), amino, lower mono or dialkylamino (1–4 carbon atoms), lower mono or dicycloalkylamino (3–8 carbon atoms), lower alkyl (1–4 carbon atoms) or cycloalkyl (3–8 carbon atoms), carbonato (—OC(O)OR) where the R is lower alkyl of 1 to 4 carbon atoms or cycloalkyl of 3–8 carbon atoms;

or ureido or thioureido or N- or O- linked urethane any one of which is optionally substituted by mono or di-lower alkyl (1–4 carbon atoms) or cycloalkyl (3–8 carbon atoms);

lower thioalkyl (1–4 carbon atoms), thiocycloalkyl (3–8 carbon atoms), mercapto, lower alkenyl (2–4 carbon atoms), hydrazino, N'-lower alkylhydrazino (1–4 carbon atoms), lower acylamino (1–4 carbon atoms), hydroxylamino, lower O-alkylhydroxylamino (1–4 carbon atoms);

or any two of $R^3$–$R^6$ taken together on contiguous carbon atoms can form a carbocyclic ring of 5–7 members or a monounsaturated 1,3-dioxolanyl, 1,4-dioxanyl, 1,4-dioxepinyl, pyranyl, furanyl, pyrrolidyl, piperidinyl, thiolanyl, oxazolanyl, thiazolanyl, diazolanyl, piperazinyl, morpholino or thiomorpholino ring;

any lower alkyl group substituent on any of the substituents in $R^3$–$R^6$ which contain such a moiety can be optionally substituted with one or more of hydroxy, amino, lower monoalkylamino, lower dialkylamino, N-pyrrolidyl, N-piperidinyl, N-pyridinium, N-morpholino, N-thiomorpholino or N-piperazino groups;

if one or more of A through E are N, then any of $R^3$–$R^6$ on a neighboring C atom to one of the N atoms, cannot be either OH or SH; and if any of the substituents $R^1$, $R^2$, $R^3$, $R^4$, $R^5$ or $R^6$ contain chiral centers, or in the case of $R^1$ create chiral centers on the linking atoms, then all stereoisomers thereof both separately and as racemic and/or diastereoisomeric mixtures are included.

Described also is a method to inhibit epidermal growth factor by treating, with an effective inhibiting amount, a mammal, in need thereof, a compound of Formula II:

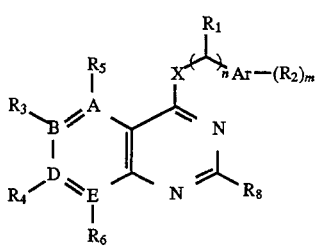

Formula II wherein

Ar, n, m, $R_1$-$R_7$ and X are the same as in Formula I;

$R^8$ is alkyl of from 1–4 carbon atoms or amino or mono or dilower alkyl (1–4 carbon atoms) amino.

The invention is also applicable to the compositions of Formulae I and II with the proviso that at least one of the $R^3$-$R^6$ substituents must be taken singly as a substituent other than hydrogen, halo, lower alkyl (1–4 carbon atoms) or lower alkoxy (1–4 carbon atoms), and with the proviso that A, B, D and E must all be taken singly as carbon or nitrogen atoms.

DESCRIPTION OF PREFERRED EMBODIMENTS

Figure 1:
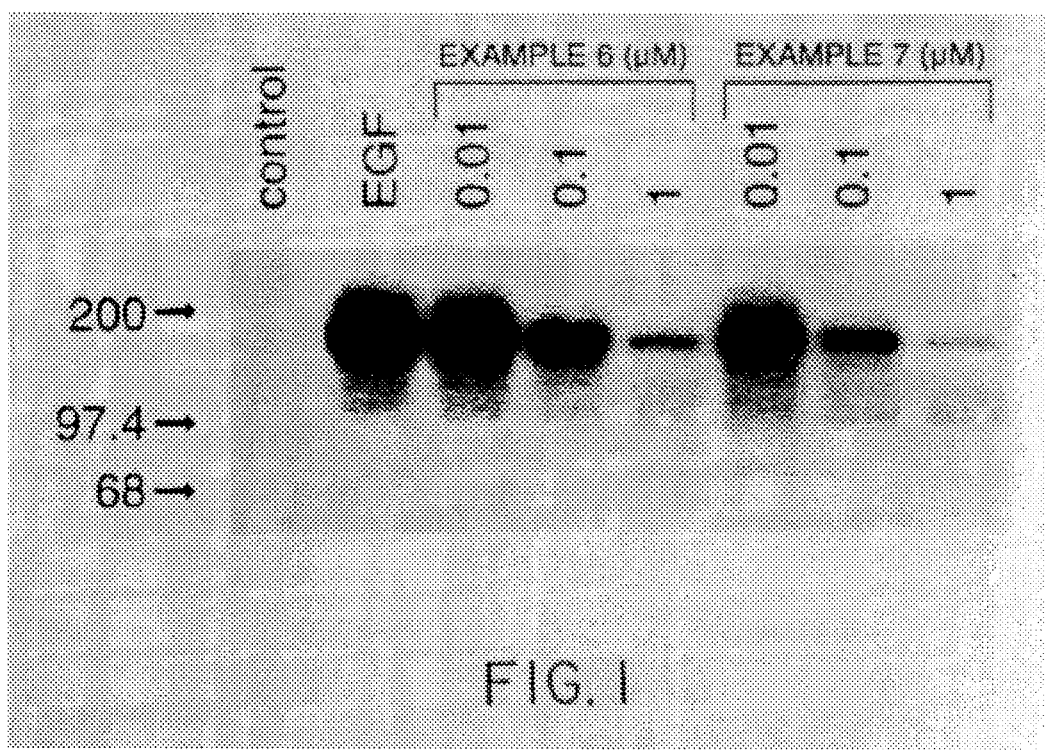
FIG. 1 is an effect of Examples 6 and 7 on EGF receptor autophosphorylation in A431 human epidermoid carcinoma.
Figure 2:
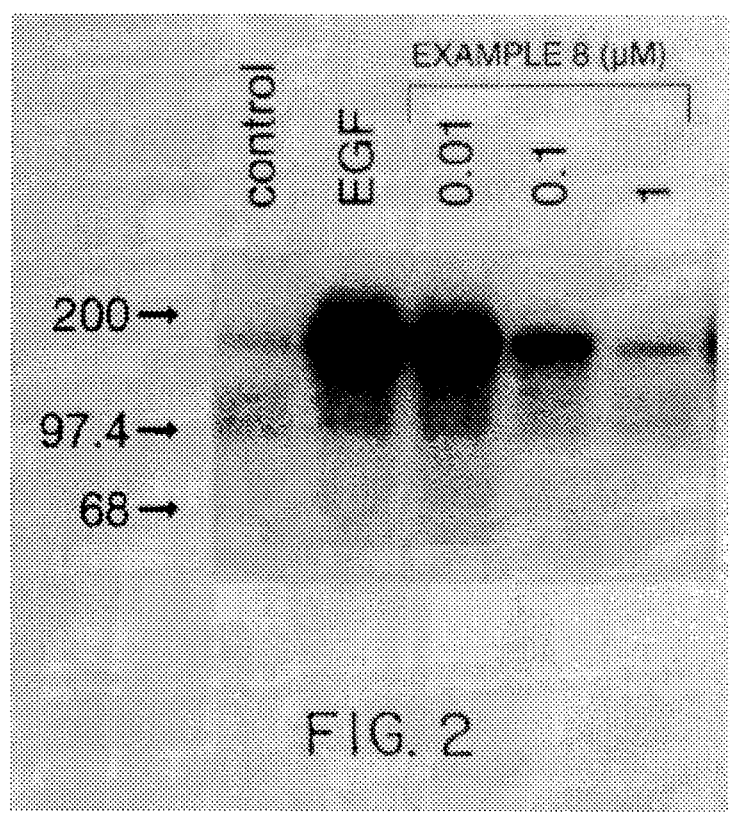
FIG. 2 is an effect of Example 8 on EGF receptor autophosphorylation in A431 human epidermoid carcinoma.
Figure 3:
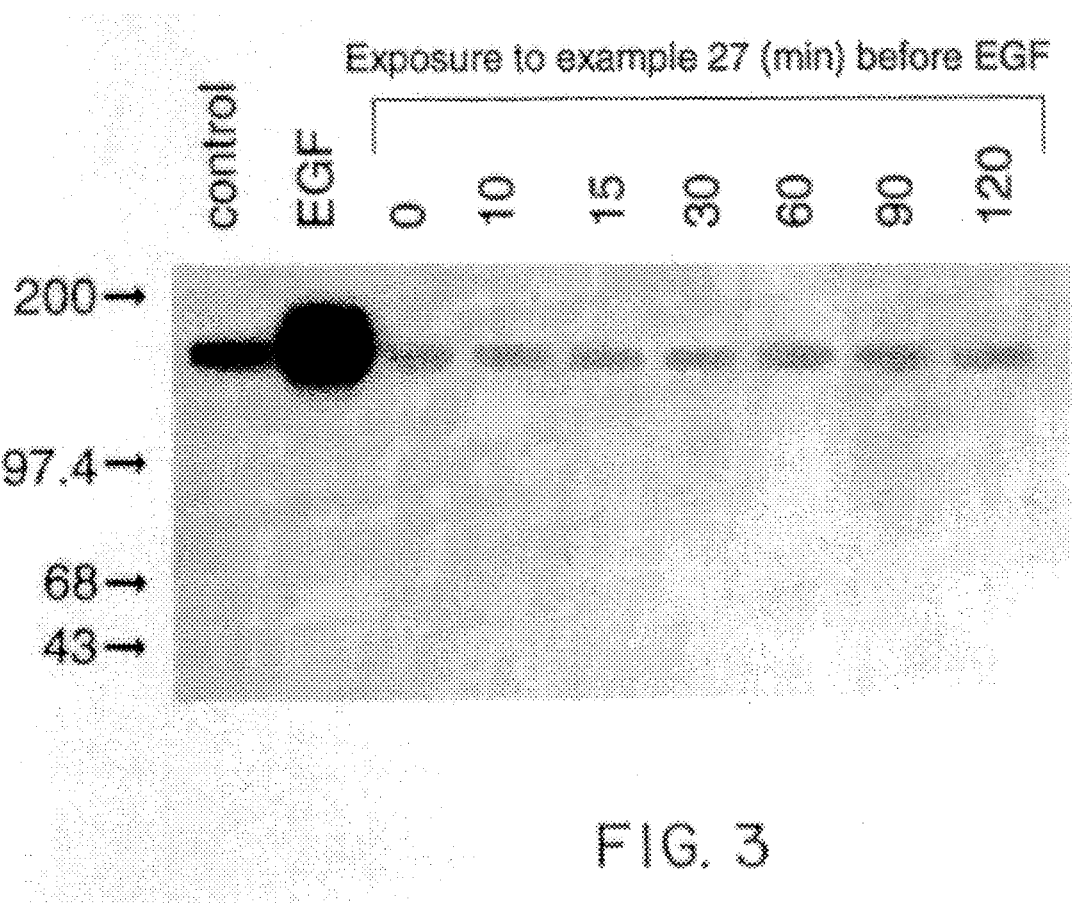
FIG. 3 is a time course for the inhibition of EGF receptor autophosphorylation in A431 by Example 27.
Figure 4:
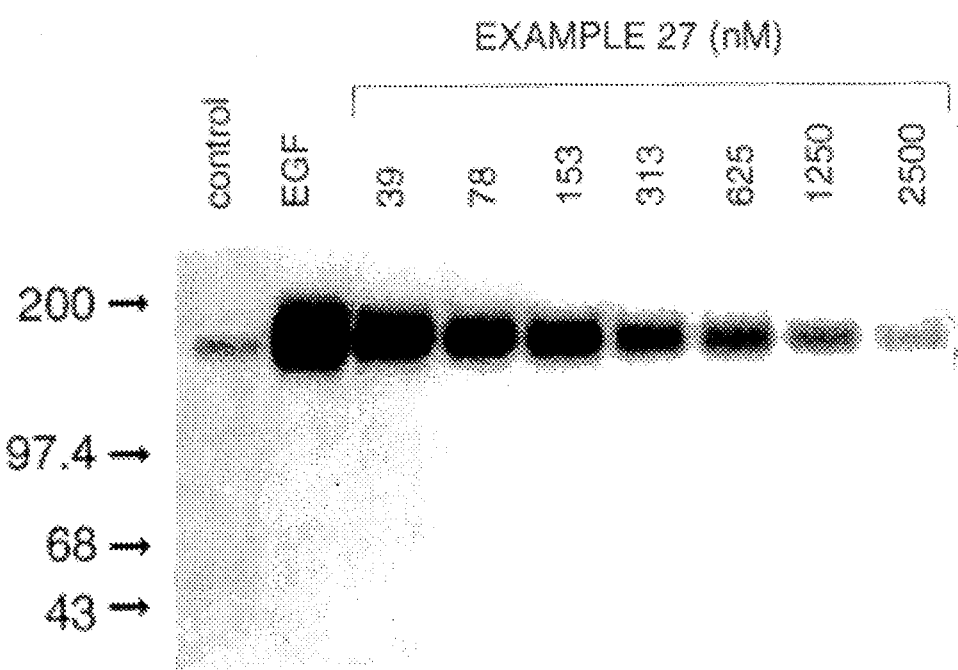
FIG. 4 is an effect of Example 27 on EGF receptor autophosphorylation in A431 cells.
Figure 5:
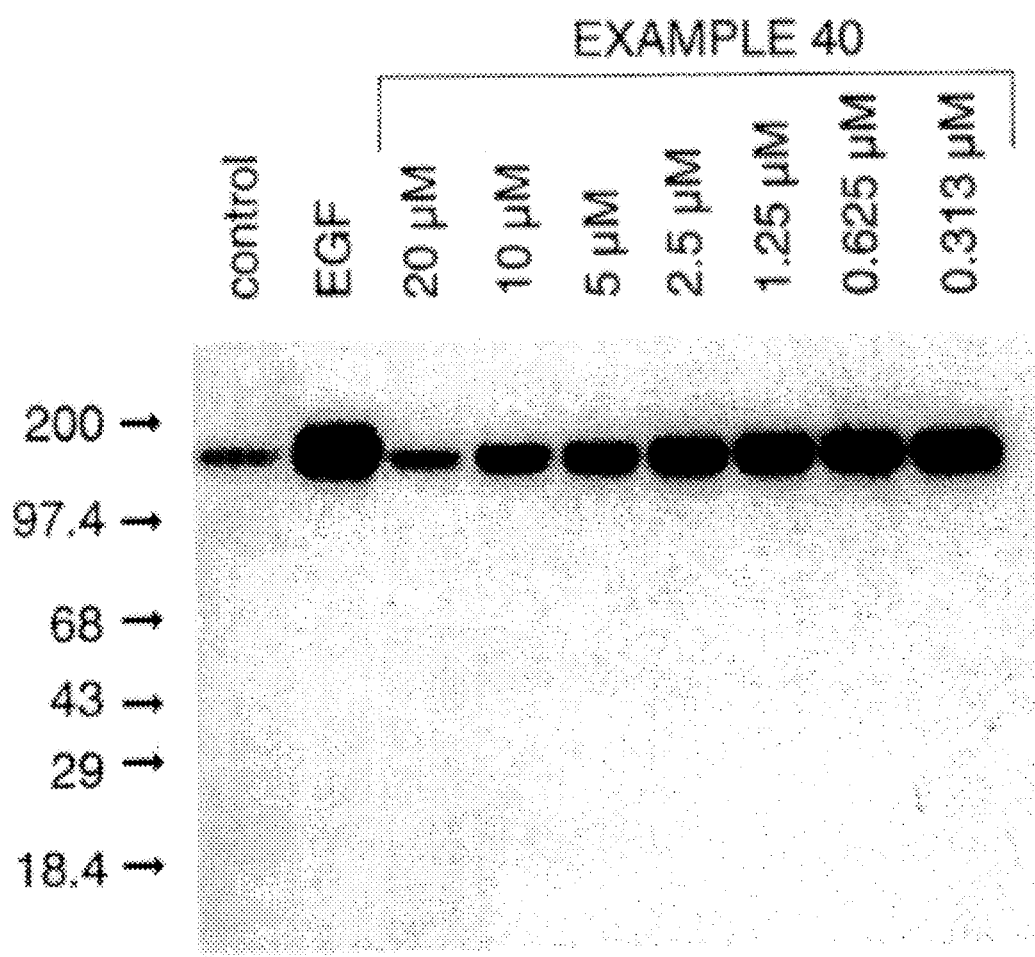
FIG. 5 is an inhibition of EGF receptor autophosphorylation in A431 human epidermoid carcinoma by Example 40.
Figure 6A:
FIG. 6 is an effect of Example 40 on growth factor-mediated tyrosine phosphorylation in Swiss 3T3.
Figure 6B:
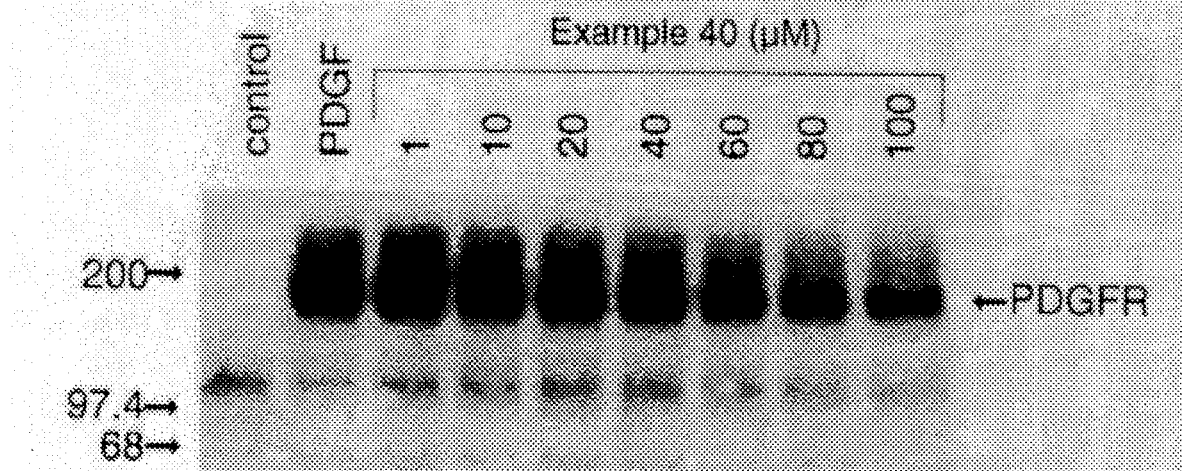
Figure 6C:
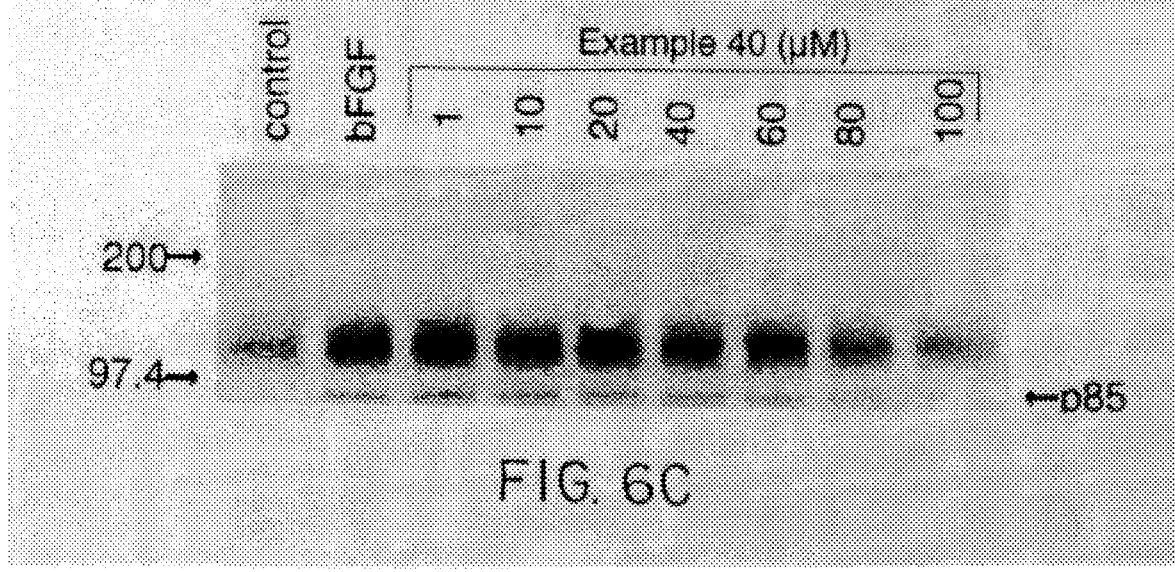

1. A preferred form of the invention has X=NH, n=0 or 1, in which case $R^1$=H, the aromatic ring phenyl optionally substituted, B, D & E carbon, with A nitrogen and $R^3$ or $R^4$ H, with the other one lower alkoxy or halogen.

2. Another preferred form of the invention has X=NH, n=0 or 1, in which case $R^1$=H, the aromatic ring phenyl optionally substituted, B, D & E carbon, with A nitrogen and $R^3$ or $R^4$ H, with the other one amino.

3. Another preferred form of the invention has X=NH, n=0 or 1, in which case $R^1$=H, the aromatic ring phenyl optionally substituted, B, D & E carbon, with A nitrogen and $R^3$ or $R^4$ H, with the other one lower mono or dialkylamino.

4. Another preferred form of the invention has X=NH, n=0 or 1, in which case $R^1$=H, the aromatic ring phenyl optionally substituted, B, D & E carbon, with A nitrogen and $R^3$ or $R^4$ H, with the other one hydrazino.

5. Another preferred form of the invention has X=NH, n=0 or 1, in which case $R^1$=H, the aromatic ring phenyl optionally substituted, B, D & E carbon, with A nitrogen and $R^3$ or $R^4$ H, with the other one lower alkyl.

6. Another preferred form of the invention has X=NH, n=0 or 1, in which case $R^1$=H, the aromatic ring phenyl optionally substituted, B, D & E carbon, with A nitrogen and $R^3$ and $R^4$ lower alkoxy.

7. Another preferred form of the invention has X=NH, n=0 or 1, in which case $R^1$=H, the aromatic ring phenyl optionally substituted, B, D & E carbon, with A nitrogen and $R^3$ and $R^4$ lower alkyl.

8. Another preferred form of the invention has X=NH, n=0 or 1, in which case $R^1$=H, the aromatic ring phenyl optionally substituted, B, D & E carbon, with A nitrogen, and $R^3$ or $R^4$ amino, with the other one lower alkoxy.

9. Another preferred form of the invention has X=NH, n=0 or 1, in which case $R^1$=H, the aromatic ring phenyl optionally substituted, B, D & E carbon, with A nitrogen, and $R^3$ or $R^4$ lower mono or dialkylamino, with the other one lower alkoxy.

10. Another preferred form of the invention has X=NH, n=0 or 1, in which case $R^1$=H, the aromatic ring phenyl optionally substituted, B, D & E carbon, with A nitrogen and $R^3$ lower mono or dialkylamino, with $R^4$ hydroxy.

A suitable ring structure for groups 1–10 is:

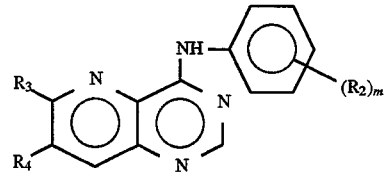

11. Another preferred form of the invention has X=NH, n=0 or 1, in which case $R^1$=H, the aromatic ring phenyl optionally substituted, B, D & E carbon, with A nitrogen, and $R^3$ and $R^4$ taken together are dioxymethylene, dioxyethylene, 2,3-fused piperazine, 2,3-fused morpholine or 2,3-fused thiomorpholine. Suitable ring structures are:

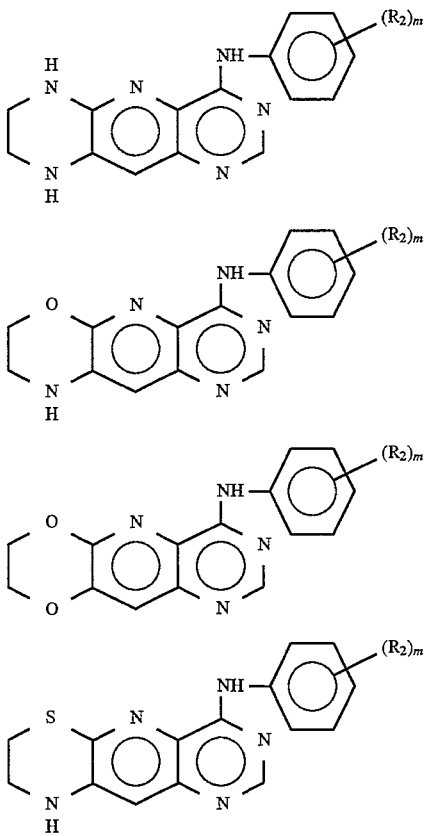

12. Another preferred form of the invention has X=NH, n=0 or 1, in which case R¹=H, the aromatic ring phenyl optionally substituted, A, D & E carbon, with B nitrogen and R⁴ lower alkoxy or halogen.

13. Another preferred form of the invention has X=NH, n=0 or 1, in which case R¹=H, the aromatic ring phenyl optionally substituted, A, D & E carbon, with B nitrogen and R⁴ amino.

14. Another preferred form of the invention has X=NH, n=0 or 1, in which case R¹=H, the aromatic ring phenyl optionally substituted, A, D & E carbon, with B nitrogen and R⁴ lower mono or dialkylamino.

15. Another preferred form of the invention has X=NH, n=0 or 1, in which case R¹=H, the aromatic ring phenyl optionally substituted, A, D & E carbon, with B nitrogen and R⁴ hydrazino.

16. Another preferred form of the invention has X=NH, n=0 or 1, in which case R¹=H, the aromatic ring phenyl optionally substituted, A, C & E carbon, with B nitrogen and R⁴ lower alkyl.

A suitable ring structure for groups 12–16 is:

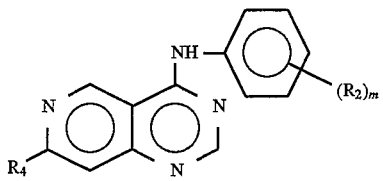

17. Another preferred form of the invention has X=NH, n=0 or 1, in which case R¹=H, the aromatic ring phenyl optionally substituted, A, B & E carbon, with D nitrogen and R³ lower alkoxy or halogen.

18. Another preferred form of the invention has X=NH, n=0 or 1, in which case R¹=H, the aromatic ring phenyl optionally substituted, A, B & E carbon, with D nitrogen and R³ amino.

19. Another preferred form of the invention has X=NH, n=0 or 1, in which case R¹=H, the aromatic ring phenyl optionally substituted, A, B & E carbon, with D nitrogen and R³ lower mono or dialkylamino.

20. Another preferred form of the invention has X=NH, n=0 or 1, in which case R¹=H, the aromatic ring phenyl optionally substituted, A, B & E carbon, with D nitrogen and R³ hydrazino.

21. Another preferred form of the invention has X=NH, n=0 or 1, in which case R¹=H, the aromatic ring phenyl optionally substituted, A, B & E carbon, with D nitrogen and R³ lower alkyl.

A suitable ring structure for groups 17–21 is:

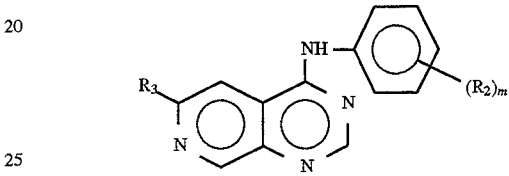

22. Another preferred form of the invention has X=NH, n=0 or 1, in which case R¹=H, the aromatic ring phenyl optionally substituted, A, B & D carbon, with E nitrogen and R³ or R⁴ H, with the other one lower alkoxy.

23. Another preferred form of the invention has X=NH, n=0 or 1, in which case R¹=H, the aromatic ring phenyl optionally substituted, A, B & D carbon, with E nitrogen and R³ or R⁴ H, with the other one amino.

24. Another preferred form of the invention has X=NH, n=0 or 1, in which case R¹=H, the aromatic ring phenyl optionally substituted, A, B & D carbon, with E nitrogen and R³ or R⁴ H, with the other one lower mono or dialkylamino.

25. Another preferred form of the invention has X=NH, n=0 or 1, in which case R¹=H, the aromatic ring phenyl optionally substituted, A, B & D carbon, with E nitrogen and R³ or R⁴ H, with the other one hydrazino.

26. Another preferred form of the invention has X=NH, n=0 or 1, in which case R¹=H, the aromatic ring phenyl optionally substituted, A, B & D carbon, with E nitrogen and R³ or R⁴ H, with the other one lower alkyl.

27. Another preferred form of the invention has X=NH, n=0 or 1, in which case R¹=H, the aromatic ring phenyl optionally substituted, A, B & D carbon, with E nitrogen and R³ and R⁴ lower alkoxy.

28. Another preferred form of the invention has X=NH, n=0 or 1, in which case R¹=H, the aromatic ring phenyl optionally substituted, A, B & D carbon, with E nitrogen and R³ and R⁴ lower alkyl.

29. Another preferred form of the invention has X=NH, n=0 or 1, in which case R¹=H, the aromatic ring phenyl optionally substituted, A, B & D carbon, with E nitrogen, and R³ or R⁴ amino, with the other one lower alkoxy.

30. Another preferred form of the invention has X=NH, n=0 or 1, in which case R¹ =H, the aromatic ring phenyl optionally substituted, A, B & D carbon, with E nitrogen, and R³ or R⁴ lower mono or dialkylamino, with the other one lower alkoxy.

31. Another preferred form of the invention has X=NH, n=0 or 1, in which case R¹=H, the aromatic ring phenyl optionally substituted, A, B & D carbon, with E nitrogen and $R^4$ lower mono or dialkylamino, with $R^3$ hydroxy.

A suitable ring structure for groups 22–31 is:

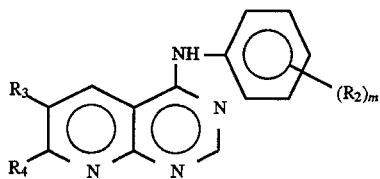

32. Another preferred form of the invention has X=NH, n=0 or 1, in which case $R^1$=H, the aromatic ring phenyl optionally substituted, A, B & D carbon, with E nitrogen, and $R^3$ and $R^4$ taken together are dioxymethylene, dioxyethylene, 2,3-fused piperazine, 2,3-fused morpholine or 2,3-fused thiomorpholine.

33. Another preferred form of the invention has X=NH, n=0, the aromatic ring phenyl optionally substituted, A & D carbon, with B and E nitrogen and $R^4$ lower alkoxy.

34. Another preferred form of the invention has X=NH, n=0, the aromatic ring phenyl optionally substituted, A & D carbon, with B and E nitrogen and $R^4$ lower mono or dialkylamino.

35. Another preferred form of the invention has X=NH, n=0, the aromatic ring phenyl optionally substituted, A & D carbon, with B and E nitrogen and $R^4$ amino.

36. Another preferred form of the invention has X=NH, n=0, the aromatic ring phenyl optionally substituted, A & D carbon, with B and E nitrogen and $R^4$ hydrazino.

A suitable ring structure for groups 33–36 is:

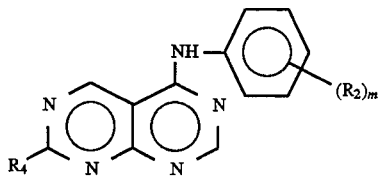

37. Another preferred form of the invention has X=NH, n=0, the aromatic ring phenyl optionally substituted, B & D carbon, with A and E nitrogen and $R^3$ and $R^4$ lower alkoxy.

38. Another preferred form of the invention has X=NH, n=0, the aromatic ring phenyl optionally substituted, B & D carbon, with A and E nitrogen and $R^3$ and $R^4$ lower mono or dialkylamino.

39. Another preferred form of the invention has X=NH, n=0, the aromatic ring phenyl optionally substituted, B & D carbon, with A and E nitrogen and $R^3$ or $R^4$ lower alkoxy, with the other lower mono or dialkylamino.

40. Another preferred form of the invention has X=NH, n=0, the aromatic ring phenyl optionally substituted, B & D carbon, with A and E nitrogen and $R^3$ and $R^4$ taken together are ethylenedioxy, 2,3-fused piperazine, 2,3-fused morpholine or 2,3-fused thiomorpholine.

A suitable ring structure for groups 37–40 is:

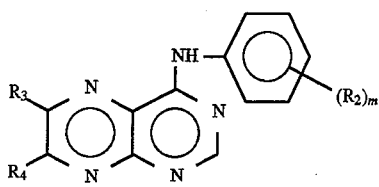

41. Another preferred form of the invention has X=NH, n=0 or 1, in which case $R^1$=H, the aromatic ring phenyl optionally substituted, and either A and B taken together are a sulfur atom, with D & E carbon, or A & B are carbon with D and E taken together as a sulfur atom, with $R^4$ or $R^3$ H, lower alkyl, lower alkoxy, amino, or lower mono or dialkylamino.

42. Another preferred form of the invention has X=NH, n=0 or 1, in which case $R^1$=H, the aromatic ring phenyl optionally substituted, and either A and B taken together are an oxygen atom, with D & E carbon, or A & B are carbon with D and E taken together as an oxygen atom, with $R^4$ or $R^3$ H, lower alkyl, lower alkoxy, amino, or lower mono or dialkylamino.

43. Another preferred form of the invention has X=NH, n=0 or 1, in which case $R^1$=H, the aromatic ring phenyl optionally substituted, and either A and B taken together are a nitrogen atom, with D & E carbon, or A & B are carbon with D and E taken together as a nitrogen atom, with $R^4$ or $R^3$ H, lower alkyl, lower alkoxy, amino, or lower mono or dialkylamino.

44. Another preferred form of the invention has X=NH, n=0 or 1, in which case $R^1$=H, the aromatic ring phenyl optionally substituted, and either A and B taken together are a sulfur atom with D carbon and E nitrogen, or D and E taken together are a sulfur atom, and A is nitrogen and B is carbon, with $R^{3/4}$ H, lower alkyl, lower alkoxy, amino, or lower mono or dialkylamino.

45. Another preferred form of the invention has X=NH, n=0 or 1, in which case $R^1$=H, the aromatic ring phenyl optionally substituted, and either A and B taken together are an oxygen atom with D carbon and E nitrogen, or D and E taken together are an oxygen atom, and A is nitrogen and B is carbon, with $R^{3/4}$ H, lower alkyl, lower alkoxy, amino, or lower mono or dialkylamino.

46. Another preferred form of the invention has X=NH, n=0 or 1, in which case $R^1$=H, the aromatic ring phenyl optionally substituted, A and B taken together are a nitrogen atom, and D is carbon and E is nitrogen, with $R^{3/6}$ H, or lower alkyl, and $R^4$ H, lower alkyl, lower alkoxy, amino, or lower mono or dialkylamino.

47. Another preferred form of the invention has X=NH, n=0 or 1, in which case $R^1$=H, the aromatic ring phenyl optionally substituted, and either A and B taken together are an oxygen atom with D nitrogen and E carbon, or A and B taken together are a carbon atom with D nitrogen and E oxygen, with $R^{3/6}$ H, lower alkyl, lower alkoxy, amino, or lower mono or dialkylamino.

48. Another preferred form of the invention has X=NH, n=0 or 1, in which case $R^1$=H, the aromatic ring phenyl optionally substituted, and either A and B taken together are a sulfur atom with D nitrogen and E carbon, or A and B taken together are a carbon atom with D nitrogen and E sulfur, with $R^{3/6}$ H, lower alkyl, lower alkoxy, amino, or lower mono or dialkylamino.

49. Another preferred form of the invention has X=NH, n=0 or 1, in which case $R^1$=H, the aromatic ring phenyl optionally substituted, and either A and B taken together are a nitrogen atom with D nitrogen and E carbon, or A and B taken together are a carbon atom with D and E nitrogen atoms, with $R^{3/6}$ H or lower alkyl if on nitrogen, or H, lower alkyl, lower alkoxy, amino, or lower mono or dialkylamino if on carbon.

Other suitable ring structures are:

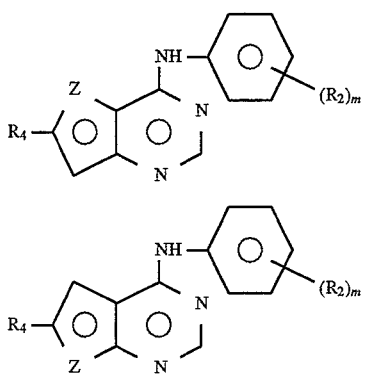

Where Z = nitrogen, oxygen or sulfur

The compounds of the present invention are prepared according to a number of alternative reaction sequences.

Preparative Routes to Compounds of the Invention

Scheme 1—Route for Preferred Groups 1–5, $R^4$=H

Displacement of the 2-chloro of 2,6-dichloro-3-nitropyridine is carried out by cuprous cyanide in NMP. Displacement of the second chlorine of this nitrile by fluoride at this step can be advantageous. This is followed by a mild reduction of the nitro group, under conditions where the halogen is not hydrogenolysed. Hydrolysis of the nitrile followed by orthoformate cyclization, and Viismeier-type chlorination will give the dihalopyridopyrimidine. Displacement of the more reactive 4-chlorine with an appropriate amine is followed by displacement of the 6-halogen with the appropriate nucleophile, ammonia, lower alkylamine, hydrazine, methoxide, to form the final products. (NMP is a solvent, N-methyl-2-pyrrolidone).

1. A preferred form of the invention has X=NH, n=0 or 1, in which case $R^1$=H, the aromatic ring phenyl optionally substituted, B, D & E carbon, with A nitrogen and $R^3$ or $R^4$ H, with the other one lower alkoxy or halogen.

2. Another preferred form of the invention has X=NH, n=0 or 1, in which case $R^1$=H, the aromatic ring phenyl optionally substituted, B, D & E carbon, with A nitrogen and $R^3$ or $R^4$ H, with the other one amino.

3. Another preferred form of the invention has X=NH, n=0 or 1, in which case $R^1$=H, the aromatic ring phenyl optionally substituted, B, D & E carbon, with A nitrogen and $R^3$ or $R^4$ H, with the other one lower mono or dialkylamino.

4. Another preferred form of the invention has X=NH, n=0 or 1, in which case $R^1$=H, the aromatic ring phenyl optionally substituted, B, D & E carbon, with A nitrogen and $R^3$ or $R^4$ H, with the other one hydrazino.

5. Another preferred form of the invention has X=NH, n=0 or 1, in which case $R^1$=H, the aromatic ring phenyl optionally substituted, B, D & E carbon, with A nitrogen and $R^3$ or $R^4$ H, with the other one lower alkyl.

Scheme 2—Route to Preferred Groups 1–5, $R^3$=H

Displacement of chlorine from 2-chloro-3,5-dinitropyridine is accomplished with CuCN in NMP. Reduction of the nitro groups to amines is followed by hydrolysis of the nitrile to an amide. This is cyclized to the pyrimidone with orthoformate, which is converted to the chloride by $POCl_3$ or possibly turned into the thiomethyl derivative by treatment with phosphorus pentasulfide followed by MeI and a mild base. Displacement with the appropriate amine gives the desired 7-amino compound. The amine functionality can be reductively alkylated or activated by diazotisation of the amino group under acidic or basic conditions, followed by a reduction to the hydrazide, or conversion into a lower alkyl ether, or to a halogen followed by a cuprate or Stille coupling by methods familiar to those skilled in the art. Alternatively, the amine can be reductively aminated, or acylated and reduced to form the alkylamino side chain.

Scheme 3—Route to Preferred Groups 6 and 8–10 where $R^4$=RO

The known metalation of 2,6-difluoropyridine is exploited twice. LDA treatment followed by a borate/hydrogen peroxide introduces the 3-hydroxy substituent. If the pyridine undergoes the 2nd metalation at the 4 position, the alcohol can be protected as a TIPS (triisopropyl silyl) ether, which will force the second metalation to the 5-position. Alternative nitrations may be used, such as converting the lithium intermediate to a stannane and treatment with tetranitromethane, or the use of $NO_2BF_4$ (nitronium tetrafluoroborate). The $C_1$ displacement may be effected by cuprous cyanide or other sources of cyanide ion. After nitrile hydrolysis and nitro group reduction, ethyl orthoformate may be used instead of formamide for the cyclization, and it may be that some cyclizations will require displacement of F by MeS prior to the reaction. The 4-position is activated by chlorination, and the sidechain amine is then introduced. The final displacement can be by alkoxide or amine nucleophiles to generate the various dialkoxy and amino-alkoxy species, and the appropriate use of R can allow the 7-hydroxyl group to be unmasked at the end of the synthesis. (LDA means lithium diisopropyl amide).

6. Another preferred form of the invention has X=NH, n=0 or 1, in which case $R^1$=H, the aromatic ring phenyl optionally substituted, B, D & E carbon, with A nitrogen and $R^3$ and $R^4$ lower alkoxy.

8. Another preferred form of the invention has X=NH, n=0 or 1, in which case $R^1$=H, the aromatic ring phenyl optionally substituted, B, D & E carbon, with A nitrogen, and $R^3$ or $R^4$ amino, with the other one lower alkoxy.

9. Another preferred form of the invention has X=NH, n=0 or 1, in which case $R^1$=H, the aromatic ring phenyl optionally substituted, B, D & E carbon, with A nitrogen, and $R^3$ or $R^4$ lower mono or dialkylamino, with the other one lower alkoxy.

10. Another preferred form of the invention has X=NH, n=0 or 1, in which case $R^1$=H, the aromatic ring phenyl optionally substituted, B, D & E carbon, with A nitrogen and $R^3$ lower mono or dialkylamino, with $R^4$ hydroxy.

Scheme 4—Route to Preferred Group 7

Use of the 6-alkylquinaldic acid followed by ionic bromination under forcing conditions gives an anhydride, which is opened with ammonia, recyclized to the imide, and then the Hoffman degradation occurs at the less active carbonyl. Cyclization and ring side chain addition in the normal manner is followed by a Stille coupling to introduce the $R^4$ alkyl group. At this step alkenyl or aryl substituents could also be introduced using this coupling technology.

7. Another preferred form of the invention has X=NH, n=0 or 1, in which case $R^1$=H, the aromatic ring phenyl optionally substituted, B, D & E carbon, with A nitrogen and $R^3$ and $R^4$ lower alkyl.

Scheme 5—Route to Preferred Groups 8, 9, $R^3$=OR

Dinitration of 2,6-dihydroxypyridine is followed by conversion to the very reactive dichlorocompound. The dinitrodichloropyridine is singly displaced by cuprous cyanide in NMP, and then the compound is reduced under mild conditions to the diamine. The nitrile is hydrolysed to the amide, which can then be cyclized to the pyridopyrimidone, which is 4-chlorinated in the usual fashion. Displacement of the more reactive chlorine with the 4-sidechain is followed by displacement of the 6-chlorine with alkoxid. For group 9, the amine should be alkylated appropriately by methods familiar to one skilled in the art.

Scheme 6—Route to Preferred Group 11

Compounds of preferred group 11 are specialized cases of preferred groups 6, 8, 9 and 10, where $R^3$ and $R^4$ are cyclized together. They can be made using the same routes as those described for the preferred groups, with minor modifications, which will be obvious to one skilled in the art. For example vicinally substituted alkoxy amino compounds can be dealkylated, and the corresponding vicinal aminoalcohols can be bisalkylated with an appropriate dihaloalkane.

11. Another preferred form of the invention has X=NH, n=0 or 1, in which case $R^1$=H, the aromatic ring phenyl optionally substituted, B, D & E carbon, with A nitrogen, and $R^3$ and $R^4$ taken together are dioxymethylene, dioxyethylene, 2,3-fused piperazine, 2,3-fused morpholine or 2,3-fused thiomorpholine.

Scheme 7—Route for Preferred Groups 12–16

2,4-Diamino-5-cyanopyridine can be cyclized directly to many 4-benzylaminopyridopyrimidine derivatives by treatment with the benzylamine and formic acid at high temperature. For less nucleophilic amines 2,4-diamino-5-cyanopyridine is converted via ethyl orthoformate/acetic anhydride treatment, followed by cyclization with hydrosulfide ion in anhydrous conditions, to give 7-amino-4-thiono-3H-pyrido[4,3-d]pyrimidine. S-Alkylation and displacement with an appropriate amine gives the desired product. If $R^4$ is not amino, the amine can be acylated, or reductively alkylated. Alternatively 2,4-diamino-5-cyanopyridine can be hydrolysed to the corresponding amide, and this species can be cyclized to 7-amino-4-oxo-3H-pyrido[4,3-d]pyrimidine with orthoformate. Diazotization of the 7-amine and replacement with fluorine allows for introduction of other amine and alkoxide nucleophiles at the end of the synthesis after the C4 substituent has been introduced in the usual manner. Diazotization and replacement of the amine with bromide allows for Stille couplings at the 7-position.

12. Another preferred form of the invention has X=NH, n=0 or 1, in which case $R^1$=H, the aromatic ring phenyl optionally substituted, A, D & E carbon, with B nitrogen and $R^4$ lower alkoxy or halogen.

13. Another preferred form of the invention has X=NH, n=0 or 1, in which case $R^1$=H, the aromatic ring phenyl optionally substituted, A, D & E carbon, with B nitrogen and $R^4$ amino.

14. Another preferred form of the invention has X=NH, n=0 or 1, in which case $R^1$=H, the aromatic ring phenyl optionally substituted, A, D & E carbon, with B nitrogen and $R^4$ lower mono or dialkylamino.

15. Another preferred form of the invention has X=NH, n=0 or 1, in which case $R^1$=H, the aromatic ring phenyl optionally substituted, A, D & E carbon, with B nitrogen and $R^4$ hydrazino.

16. Another preferred form of the invention has X=NH, n=0 or 1, in which case $R^1$=H, the aromatic ring phenyl optionally substituted, A, C & E carbon, with B nitrogen and $R^4$ lower alkyl.

Scheme 8—Route for Preferred Groups 17–21

2-Chloro-5-nitropyridine is converted to the corresponding 2-fluoro compound by KF in DMSO. Reduction of the nitro group followed by treatment with Boc anhydride gives the Bocamino derivative, which can be metalated and carboxylated at the 4-position. Removal of the Boc with TFA and cyclization of the pyrimidone ring with formamide gives 6-fluoro-4-oxo-3H-pyrido[3,4-d]pyrimidine. This is 4-chlorinated in the usual manner and the 4-sidechain is introduced via displacement with an appropriate amine. Displacement of the 6-fluorine with appropriate nucleophiles leads to various different final products. If the fluorine is displaced by thiomethoxide, that in turn can be displaced by alkyl groups in Ni-catalyzed Grignard displacements.

17. Another preferred form of the invention has X=NH, n=0 or 1, in which case $R^1$=H, the aromatic ring phenyl optionally substituted, A, B & E carbon, with D nitrogen and $R^3$ lower alkoxy or halogen.

18. Another preferred form of the invention has X=NH, n=0 or 1, in which case $R^1$=H, the aromatic ring phenyl optionally substituted, A, B & E carbon, with D nitrogen and $R^3$ amino.

19. Another preferred form of the invention has X=NH, n=0 or 1, in which case $R^1$=H, the aromatic ring phenyl optionally substituted, A, B & E carbon, with D nitrogen and $R^3$ lower mono or dialkylamino.

20. Another preferred form of the invention has X=NH, n=0 or 1, in which case $R^1$=H, the aromatic ring phenyl optionally substituted, A, B & E carbon, with D nitrogen and $R^3$ hydrazino.

21. Another preferred form of the invention has X=NH, n=0 or 1, in which case $R^1$=H, the aromatic ring phenyl optionally substituted, A, B & E carbon, with D nitrogen and $R^3$ lower alkyl.

Scheme 9—Route to Preferred Groups 22–26, $R^4$=H

Nitration of 2-methoxynicotinic acid is followed by displacement of the activated methoxy group and cyclization of the pyrimidone ring, possibly all in one step with formamidine, or alternatively in two steps with ammonia followed by cyclization with a formamide equivalent. The carbonyl is converted to the chloride and displaced with the sidechain in the usual fashion, and the nitro group is then selectively reduced to amino. This can be alkylated, acylated or diazotized. The diazo compound can be converted to hydroxy or to the bromide or iodide, and these latter can undergo a Stille coupling to introduce lower alkyl, alkenyl, aryl, etc. at $R^3$.

22. Another preferred form of the invention has X=NH, n=0 or 1, in which case $R^1$=H, the aromatic ring phenyl optionally substituted, A, B & D carbon, with E nitrogen and $R^3$ or $R^4$ H, with the other one lower alkoxy.

23. Another preferred form of the invention has X=NH, n=0 or 1, in which case $R^1$=H, the aromatic ring phenyl optionally substituted, A, B & D carbon, with E nitrogen and $R^3$ or $R^4$ H, with the other one amino.

24. Another preferred form of the invention has X=NH, n=0 or 1, in which case $R^1$=H, the aromatic ring phenyl optionally substituted, A, B & D carbon, with E nitrogen and $R^3$ or $R^4$ H, with the other one lower mono or dialkylamino.

25. Another preferred form of the invention has X=NH, n=0 or 1, in which case $R^1$=H, the aromatic ring phenyl optionally substituted, A, B & D carbon, with E nitrogen and $R^3$ or $R^4$ H, with the other one hydrazino.

26. Another preferred form of the invention has X=NH, n=0 or 1, in which case $R^1$=H, the aromatic ring phenyl optionally substituted, A, B & D carbon, with E nitrogen and $R^3$ or $R^4$ H, with the other one lower alkyl.

Scheme 10—Route to Preferred Groups 22–26, $R^3$=H

This route uses the known metalation and carboxylation of 2,6-difluoropyridine, followed by displacement of the 2-fluoro substituent. Cyclization of the pyrimidone ring with formamide, followed by conversion of the carbonyl into chloride in a normal manner gives a chlorofluoropyridopyrimidine. The ar(alk)ylamino sidechain is introduced by displacement of the more reactive pyrimidine chlorine, and the $R^4$ substituent is then introduced by fluoride displacement. The introduction of alkyl utilizes displacement of F by alkoxide, later ether cleavage to the pyridone, O-triflation and Stille coupling.

Scheme 11—Route to Preferred Groups 27 and 29–31, $R^3$=RO

This scheme relies on the metalation of 2,6-difluoropyridine similarly to scheme 10. The first metalation is used to introduce oxygen, and the second to introduce the carboxylic acid. If required to force the second metalation to the 5-position the oxygen may be protected as the very bulky TIPS ether, and stronger bases than LDA may be required. Ammonia is introduced at the 2-position under high temperature and pressure, and the pyridone ring is cyclized, and activated at the 4-position in the usual manner and then displaced with the 4-position sidechain. Displacement of the 7-fluoro substituent with an appropriate nucleophile, followed by conversions as described in previous schemes finishes the synthesis.

27. Another preferred form of the invention has X=NH, n=0 or 1, in which case $R^1$=H, the aromatic ring phenyl optionally substituted, A, B & D carbon, with E nitrogen and $R^3$ and $R^4$ lower alkoxy.

29. Another preferred form of the invention has X=NH, n=0 or 1, in which case $R^1$=H, the aromatic ring phenyl optionally substituted, A, B & D carbon, with E nitrogen, and $R^3$ or $R^4$ amino, with the other one lower alkoxy.

30. Another preferred form of the invention has X=NH, n=0 or 1, in which case $R^1$=H, the aromatic ring phenyl optionally substituted, A, B & D carbon, with E nitrogen, and $R^3$ or $R^4$ lower mono or dialkylamino, with the other one lower alkoxy.

31. Another preferred form of the invention has X=NH, n=0 or 1, in which case $R^1$=H, the aromatic ring phenyl optionally substituted, A, B & D carbon, with E nitrogen and $R^4$ lower mono or dialkylamino, with $R^3$ hydroxy.

Scheme 12—Route to Preferred Group 28

5-Bromo-2,6-difluoronicotinic acid is prepared from 2,6-difluoropyridine by successive lithiations using LDA. The 5-position is alkylated via a Stille coupling, and the pyrimidone ring is cyclized on in two steps. The 4-substituent is introduced in the usual fashion and the 7-fluoro group is displaced with thiomethoxide. This thioether in turn is displaced by a Grignard agent in the presence of a nickel salt catalyst. Again use of appropriate organometallic reagents in the Stille and Grignard couplings could lead to alkenyl, alkynyl and aryl substituents at $R^3$ and $R^4$.

28. Another preferred form of the invention has X=NH, n=0 or 1, in which case $R^1$=H, the aromatic ring phenyl optionally substituted, A, B & D carbon, with E nitrogen and $R^3$ and $R^4$ lower alkyl.

Scheme 13—Route to Preferred Groups 29 and 30, $R^4$=RO

Nitration of the commercially available dichloronicotinic acid is followed by a selective displacement of the more reactive Cl under mild conditions, followed by a more forcing displacement of the other Cl, in the appropriate order. The resulting 6-alkoxy-2-amino-5-nitronicotinic acid is cyclized to the pyrimidone, and the 4-carbonyl is converted to a chloride and displaced in the usual fashion with an appropriate amine to give the 4-amino-7-alkoxy-6-nitropyrido[2,3-d]pyrimidine. Reduction of the nitro group, followed by any desired alkylation or acylation gives the desired compounds.

Scheme 14—Route to Preferred Group 32

Compounds of group 32 are specialized cases of preferred groups 27, 29, 30 and 31, where $R^3$ and $R^4$ are cyclized together. They can be made using the same routes as those described for these preferred groups with minor modifications. For example, vicinally substituted alkoxy amino compounds can be dealkylated, and the corresponding vicinal amino alcohols can be bisalkylated with an appropriate dihaloalkane. Piperazines can be made by the route shown in Scheme 13, provided that a suitable amine nucleophile is used to displace the 6-chloro substituent instead of an alkoxide.

32. Another preferred form of the invention has X=NH, n=0 or 1, in which case $R^1$=H, the aromatic ring phenyl optionally substituted, A, B & D carbon, with E nitrogen, and $R^3$ and $R^4$ taken together are dioxymethylene, dioxyethylene, 2,3-fused piperazine, 2,3-fused morpholine or 2,3-fused thiomorpholine.

Scheme 15—Route to Preferred Groups 33–36

Reaction of a suitable S-alkylisothiouronium salt with methoxymethylidine malononitrile yields a fully functionalized pyrimide precursor. The initially formed pyrimidine can have the SEt displaced by $R^4$ either before or after the nitrile hydrolysis, if displacement or oxidation prove problematic later. Displacement of the SEt group can also be achieved without an oxidation to activate the sulfur. Cyclization of the second pyrimidine ring is followed by activation of the 4-carbonyl by thiation and alkylation. Even if the 7-thio group has not been displaced at this point, introduction of the 4-amino sidechain occurs preferentially.

33. Another preferred form of the invention has X=NH, n=0, the aromatic ring phenyl optionally substituted, A & D carbon, with B and E nitrogen and $R^4$ lower alkoxy.

34. Another preferred form of the invention has X=NH, n=0, the aromatic ring phenyl optionally substituted, A & D carbon, with B and E nitrogen and $R^4$ lower mono or dialkylamino.

35. Another preferred form of the invention has X=NH, n=0, the aromatic ring phenyl optionally substituted, A & D carbon, with B and E nitrogen and $R^4$ amino.

36. Another preferred form of the invention has X=NH, n=0, the aromatic ring phenyl optionally substituted, A & D carbon, with B and E nitrogen and $R^4$ hydrazino.

Scheme 16—Route to Preferred Groups 37–40

The pterine nucleus is made by well-established procedure. For group 37, the pterindione intermediate can be O-alkylated, and for it, and the other groups, the pterindione can be converted to the trichloropterin, and selective displacements can be carried out on the halogens in an order appropriate to give the desired compound.

37. Another preferred form of the invention has X=NH, n=0, the aromatic ring phenyl optionally substituted, B & D carbon, with A and E nitrogen and $R^3$ and $R^4$ lower alkoxy.

38. Another preferred form of the invention has X=NH, n=0, the aromatic ring phenyl optionally substituted, B & D carbon, with A and E nitrogen and $R^3$ and $R^4$ lower mono or dialkylamino.

39. Another preferred form of the invention has X=NH, n=0, the aromatic ring phenyl optionally substituted, B & D carbon, with A and E nitrogen and $R^3$ or $R^4$ lower alkoxy, with the other lower mono or dialkylamino.

40. Another preferred form of the invention has X=NH, n=0, the aromatic ring phenyl optionally substituted, B & D carbon, with A and E nitrogen and $R^3$ and $R^4$ taken together are ethylenedioxy, 2,3-fused piperazine, 2,3-fused morpholine or 2,3-fused thiomorpholine.

Scheme 17—Route to Preferred Groups 41 [3,2-d] ring fusion

3,H-Thieno[3,2-d]pyrimid-4-one can be made by standard chemistry from commercially available ethyl 3-aminothiophene carboxylate and formamide. Conversion of the carbonyl to chloride by standard techniques followed by displacement with an appropriate amine gives the desired thieno[3,2-d]pyrimidines. If $R^4$ is not H, an appropriate electrophile, for example nitro for amine based or diazotization derived substituents, or Br for Stille coupled final products, can be introduced either at the stage shown or an earlier stage, and then be converted to $R^4$, by reduction and amination for example or by Stille coupling, or other methods known to those skilled in the art. [This technique follows also for all of the following preferred categories which have the possibility of substitution on $R^3$ or $R^4$, as they are all contain electron rich five membered rings which can be readily manipulated by electrophilic aromatic substitution.] (DMSO is dimethyl sulfoxide).

41. Another preferred form of the invention has X=NH, n=0 or 1, in which case $R^1$=H, the aromatic ring phenyl optionally substituted, and either A and B taken together are a sulfur atom, with D & E carbon, or A & B are carbon with D and E taken together as a sulfur atom, with $R^4$ or $R^3$ H, lower alkyl, lower alkoxy, amino, or lower mono or dialkylamino.

Scheme 18—Route to Preferred Groups 41 [2,3-d] ring fusion

Thieno[2,3-d]pyrimid-4-one is built up by the Gewald synthesis from 2,5-dihydroxy-1,4-dithiane and ethyl cyanoacetate, followed by formamide cyclization. Conversion of the carbonyl to chloride by standard techniques followed by displacement with an appropriate amine gives the desired thieno[2,3-d]pyrimidines.

Scheme 19—Route to Preferred Groups 42 [3,2-d] ring fusion

The [3,2-d]ring fusion compounds are obtained from 3-bromofurfural as shown above in Scheme A. Displacement of the bromide by azide, followed by oxidation of the aldehyde sets up the basic aminofuroic acid needed to fuse on the pyrimidine ring. The annulation shown can be used, or by manipulating which acid derivative is actually used, one could use a variety of other ring annularions, and subsequent activations of the 4-position if required.

42. Another preferred form of the invention has X=NH, n=0 or 1, in which case $R^1$=H, the aromatic ring phenyl optionally substituted, and either A and B taken together are an oxygen atom, with D & E carbon, or A & B are carbon with D and E taken together as an oxygen atom, with $R^4$ or $R^3$ H, lower alkyl, lower alkoxy, amino, or lower mono or dialkylamino.

Scheme 20—Route to Preferred Groups 42 [2,3-d] ring fusion

Reaction of 6-chloro-4-methylthiopyrimidine with LDA followed by DMF gives the corresponding 5-aldehyde, which is treated with the sodium salt of an appropriate glycollate ester, displacing chlorine, and in situ forming the furan ring by intramolecular aldol condensation. Cleavage of the ester and decarboxylation of the unwanted 7-acid functionality may be done in a single reaction with a good nucleophile in a dipolar aprotic solvent at high temperature, or in separate saponification and Cu/quinoline decarboxylation steps. Displacement of the 4-methylthio group by an appropriate amine gives the desired furano[2,3-d]pyrimidines.

Scheme 21—Route to Preferred Groups 43 [2,3-d] ring fusion

To make the pyrrolo[2,3-d]pyrimidine a pyrimidine ring is cyclized onto the cyano aminopyrrole using known techniques as shown in scheme B above. Activation and displacement of the thiol by the side chain can be preceded or followed by the optional electrophilic substitution of the pyrrole ring.

43. Another preferred form of the invention has X=NH, n=0 or 1, in which case $R^1$=H, the aromatic ring phenyl optionally substituted, and either A and B taken together are a nitrogen atom, with D & E carbon, or A & B are carbon with D and E taken together as a nitrogen atom, with $R^4$or $R^3$ H, lower alkyl, lower alkoxy, amino, or lower mono or dialkylamino.

Scheme 22—Route to Preferred Groups 43 [3,2-d] ring fusion

The preparation of the pyrrolo[3,2-d]pyrimidine exploits the known condensation of orthoformate with the acidified 4-methyl group of 6-pyrimidones to form the pyrrolopyrimidine as shown above. The side chain can be put on by standard techniques such as in Scheme 1, and the $R^4$ substituent can be introduced by standard electrophilic chemistry as described above.

Scheme 23—Route to Preferred Groups 44 [5,4-d] ring fusion

Condensation of dithioformic acid with 2-aminomalononitrile in the presence of a dehydrating agent such as PPA gives 5-amino-4-cyanothiazole. Reaction of this with orthoformate, followed by treatment with MeSNa gives a thiazolo[5,4-d]pyrimidine derivative, which on treatment with an appropriate amine give the desired compounds.

44. Another preferred form of the invention has X=NH, n=0 or 1, in which case $R^1$=H, the aromatic ring phenyl optionally substituted, and either A and B taken together are a sulfur atom with D carbon and E nitrogen, or D and E taken together are a sulfur atom, and A is nitrogen and B is carbon, with $R^{3/4}$ H, lower alkyl, lower alkoxy, amino, or lower mono or dialkylamino.

Scheme 24—Route to Preferred Groups 44 [4,5-d] ring fusion

Reaction of N-cyanobismethylthiomethyl-eneimine with ethyl thioglycollate gives ethyl 2-methylthio-4-aminothiazole-5-carboxamide. Cyclization with formamide or equivalent, followed by desulfurization of the methylthio gives a thiazolopyrimidone, which can be activated by Viismeier reagent ,and the chloride displaced by the desired amine to give the desired thiazolo[4,5-d]pyrimidine derivatives as shown above.

Scheme 25—Route to Preferred Groups 45 [5,4-d] ring fusion

The known 5-amino-4-cyanooxazole is treated with ethyl orthoformate/acetic anhydride, and is then reacted with MeSNa to give 4-methylthiooxazolo[5,4-d]pyrimidine, which on displacement with the appropriate amine gives the desired oxazolo[5,4-d]pyrimidines as shown above.

45. Another preferred form of the invention has X=NH, n=0 or 1, in which case R¹=H, the aromatic ring phenyl optionally substituted, and either A and B taken together are an oxygen atom with D carbon and E nitrogen, or D and E taken together are an oxygen atom, and A is nitrogen and B is carbon, with $R^{3/4}$ H, lower alkyl, lower alkoxy, amino, or lower mono or dialkylamino.

Scheme 26—Route to Preferred Groups 45 [4,5-d] ring fusion

Diazotization of the known 5-amino-4,6-dichloropyrimidine, followed by dilute sulfuric acid treatment give the corresponding 5-hydroxy compound. One of the chlorines is displaced with ammonia, and the oxazole ring is annulated with formic acid or an appropriate equivalent. Displacement of the other chlorine with an appropriate amine gives the desired oxazolo[4,5-d]pyrimidines as shown above.

Scheme 27—Route to Preferred Groups 46

These compounds can be made by straightforward displacement of halogen on appropriate 6-chloropurines, by means well documented in the art. R³ substituents can be introduced via facile electrophilic substitutions at the activated 8-position of the purine nucleus, followed by the types of transformation discussed in previous examples.

46. Another preferred form of the invention has X=NH, n=0 or 1, in which case R¹=H, the aromatic ring phenyl optionally substituted, A and B taken together are a nitrogen atom, and D is carbon and E is nitrogen, with $R^{3/6}$ H, or lower alkyl, and R⁴ H, lower alkyl, lower alkoxy, amino, or lower mono or dialkylamino.

Scheme 28—Route to Preferred Groups 47 [5,4-d] ring fusion

Reaction of 6-chloro-4-methylthiopyrimidine with LDA followed by DMF gives the corresponding 5-aldehyde, which is treated with hydroxylamine under mild acidic conditions, and then basic conditions to complete the ring annulation giving 4-methylthioisoxazolo[5,4-d]pyrimidine, which on displacement with an appropriate amine gives the desired isoxazolo[5,4-d]pyrimidine derivatives as shown above.

47. Another preferred form of the invention has X=NH, n=0 or 1, in which case R¹=H, the aromatic ring phenyl optionally substituted, and either A and B taken together are an oxygen atom with D nitrogen and E carbon, or A and B taken together are a carbon atom with D nitrogen and E oxygen, with $R^{3/6}$ H, lower alkyl, lower alkoxy, amino, or lower mono or dialkylamino.

Scheme 29—Route to Preferred Groups 47 [4,5-d] ring fusion

Reaction of 4,6-dichloro-5-nitropyrimidine with CuCN/NMP gives the 4-nitrile. Reduction of the nitro group to the corresponding amine is followed by diazotization and treatment with dilute sulfuric acid to give the corresponding 5-hydroxy compound. Reaction of this with Me₃Al/NH₄Cl gives the amidine which is oxidatively cyclized to 7-amino-4-chloroisoxazolo[4,5-d]pyrimidine. Removal of the amino functionality by diazotization/hypophosphorus acid is followed by displacement of the 4-chlorine with an appropriate amine to give the desired isoxazolo[4,5-d]pyrimidine derivatives as shown above.

Scheme 30—Route to Preferred Groups 48 [5,4-d] ring fusion

Reaction of 6-chloro-4-methylthiopyrimidine with LDA followed by DMF gives the corresponding 5-aldehyde, which is treated sequentially with NaSH, NBS and ammonia to complete the ring annulation giving 4-methylthioisothiazolo[5,4-d]pyrimidine, which on displacement with an appropriate amine gives the desired isothiazolo[5,4-d]pyrimidine derivatives as shown above.

48. Another preferred form of the invention has X=NH, n=0 or 1, in which case R¹=H, the aromatic ring phenyl optionally substituted, and either A and B taken together are a sulfur atom with D nitrogen and E carbon, or A and B taken together are a carbon atom with D nitrogen and E sulfur, with $R^{3/6}$ H, lower alkyl, lower alkoxy, amino, or lower mono or dialkylamino.

Scheme 31—Route to Preferred Groups 48 [4,5-d] ring fusion

Reaction of 4,6-dichloro-5-nitropyrimidine with CuCN/NMP gives the 4-nitrile. Reduction of the nitro group to the amine is followed by diazotization/thiation to give the corresponding 5-mercapto compound. Reaction of this with Me₃Al/NH₄Cl gives the amidine which is oxidatively cyclized with NBS to 7-amino-4-chloroisothiazolo[4,5-d]pyrimidine. Removal of the amino functionality by diazotization/hypophosphorus acid is followed by displacement of the 4-chlorine with an appropriate amine to give the desired isothiazolo4,3-d]pyrimidine derivatives as shown above.

Scheme 32—Route to Preferred Groups 49 [3,4-d] ring fusion

Reaction of 6-chloro-4-methylthiopyrimidine with LDA followed by DMF gives the corresponding 5-aldehyde, which is treated with hydrazine to do the ring annulation giving 4-methylthiopyrazolo[3,4-d]pyrimidine, which on displacement with an appropriate amine gives the desired pyrazolo[3,4-d]pyrimidine derivatives as shown above.

49. Another preferred form of the invention has X=NH, n=0 or 1, in which case R¹=H, the aromatic ring phenyl optionally substituted, and either A and B taken together are a nitrogen atom with D nitrogen and E carbon, or A and B taken together are a carbon atom with D and E nitrogen atoms, with $R^{3/6}$ H or lower alkyl if on nitrogen, or H, lower alkyl, lower alkoxy, amino, or lower mono or dialkylamino if on carbon.

Scheme 33—Route to Preferred Groups 49 [4,3-d] ring fusion

Nitration of pyrazole-3-carboxylic acid followed by reduction gives 4-aminopyrazole-3-carboxylic acid. This is cyclized to pyrazolo[4,3-d]pyrimid-4-one with formamidine HCl, and replacement of the carbonyl with halide by standard procedures, followed by displacement of the chloride by an appropriate amine yields the desired pyrazolo[4,3-d]pyrimidine, as shown above.

Most Preferred Forms of the Invention

1. A most preferred form of the invention is one where X=NH, x=0, the aromatic ring ms 3-bromophenyl, B, D & E are carbon, A ms nitrogen, and R⁴ is amino.

2. A most preferred form of the invention is one where X=NH, x=0, the aromatic ring ms 3-bromophenyl, B, D & E are carbon, A ms nitrogen, and R⁴ is methylamino.

3. A most preferred form of the invention is one where X=NH, x=0, the aromatic ring ms 3-bromophenyl, B, D & E are carbon, A is nitrogen, and R⁴ is dimethylamino.

4. A most preferred form of the invention is one where X=NH, x=0, the aromatic ring ms 3-nitrophenyl, A, D & E are carbon, B ms nitrogen, and R⁴ is amino.

5. A most preferred form of the invention is one where X=NH, x=0, the aromatic ring ms 3-bromophenyl, A, D & E are carbon, B ms nitrogen, and R⁴ is amino.

6. A most preferred form of the invention is one where X=NH, x=0, the aromatic ring ms 4-bromophenyl, A, D & E are carbon, B ms nitrogen, and $R^4$ is amino.

7. A most preferred form of the invention is one where X=NH, x=0, the aromatic ring ms 3-trifluoromethylphenyl, A, D & E are carbon, B is nitrogen, and $R^4$ is amino.

8. A most preferred form of the invention is one where X=NH, x=0, the aromatic ring is 3-bromophenyl, A, D & E are carbon, B is nitrogen, and $R^4$ is acetylamino.

9. A most preferred form of the invention is one where X=NH, x=1, $R^1$=H, the aromatic ring is phenyl, A, D & E are carbon, B is nitrogen.

10. A most preferred form of the invention is one where X=NH, x=1, $R^1$=H, the aromatic ring is phenyl, A, D & E are carbon, B is nitrogen, and $R^4$ is acetylamino.

11. A most preferred form of the invention is one where X=NH, x=0, the aromatic ring is 3-bromophenyl, A, B & E are carbon, D is nitrogen, $R^3$=Cl.

12. A most preferred form of the invention is one where X=NH, x=0, the aromatic ring is 3-bromophenyl, A, D & E are carbon, D is nitrogen, and $R^3$ is methoxy.

13. A most preferred form of the invention is one where X=NH, x=0, the aromatic ring is 3-bromophenyl, A, D & E are carbon, D is nitrogen, and $R^3$ is methylamino.

14. A most preferred form of the invention is one where X=NH, x=0, the aromatic ring is 3-bromophenyl, A, D & E are carbon, D is nitrogen, and $R^3$ is dimethylamino.

15 A most preferred form of the invention is one where X=NH, x=0, the aromatic ring is 3-bromophenyl, D & E are carbon, and A and B taken together are S.

16 A most preferred form of the invention is one where X=NH, x=1, $R^1$=H, the aromatic ring is phenyl, D & E are carbon, and A and B taken together are S.

17 A most preferred form of the invention is one where X=NH, x=0, the aromatic ring is 3-bromophenyl, A & B are carbon, and D and E taken together are S.

18 A most preferred form of the invention is one where X=NH, x=0, the aromatic ring is 3-bromophenyl, B is carbon, and A, and D and E taken together, are nitrogen.

19 A most preferred form of the invention is one where X=NH, x=0, the aromatic ring is 3-bromophenyl, A, B & E are carbon, D is nitrogen, and $R^3$ is N-piperinyl.

20 A most preferred form of the invention is one where X=NH, x=0, the aromatic ring is 3-bromophenyl, A, D & E are carbon, B is nitrogen, and $R^4$ is fluoro.

21. A most preferred form of the invention is one where X=NH, x=0, the aromatic ring is 3-hydroxyphenyl, A, D & E are carbon, B is nitrogen, and $R^4$ is amino.

22. A most preferred form of the invention is one where X=NH, x=0, the aromatic ring is 3-bromophenyl, A, D & E are carbon, B is nitrogen, and $R^4$ is methylamino.

23. A most preferred form of the invention is one where X=NH, x=0, the aromatic ring is 3-bromophenyl, A, D & E are carbon, B is nitrogen, and $R^4$ is dimethylamino.

24. A most preferred form of the invention is one where X=NMe, x=0, the aromatic ring is 3-bromophenyl, A, D & E are carbon, B is nitrogen, and $R^4$ is methylamino.

25. A most preferred form of the invention is one where X=NH, x=0, the aromatic ring is 3-bromophenyl, A, D & E are carbon, B is nitrogen, and $R^4$ is methoxy.

26. A most preferred form of the invention is one where X=NH, x=0, the aromatic ring is 3-bromophenyl, A, B & D are carbon, E is nitrogen, and $R^4$ is fluoro.

Biology

These compounds are potent and selective inhibitors of the human EGF receptor tyrosine kinase, and other members of the EGF receptor family, including the ERB-B2, ERB-B3 and ERB-B4 receptor kinases, and are useful for the treatment of proliferative diseases in mammals. These inhibitors prevent mitogenesis in cells where mitogenesis is driven by one or more of this family of receptor kinases. This can include normal cells, where it is desired to prevent mitogenesis, as exemplified by the cells transformed by overexpression or mutation of this kinase family as exemplified by poor prognosis breast cancer where overexpression of EGFR, ERB-B2 and ERB-B3 or mutation of ERB-B2 to the oncoprotein NEU is a major factor in cellular transformation. As the preferred compounds are not highly cytotoxic and do not show potent growth inhibitory properties, because of their high specificity toward inhibition of the EGFR kinase family, they should have a much cleaner toxicity profile than most anti-cancer and anti-proliferative drugs. Their very different mode of action to current anti-cancer drugs should allow for their use in multiple drug therapies, where synergism with available agents is anticipated.

Compounds of the invention have been shown to be very potent, reversible inhibitors of the EGF receptor tyrosine kinase, by binding with high affinity at the adenosine triphosphate (ATP) binding site of the kinase. These compounds exhibit potent $IC_{50}$s, varying from 10 micromolar to 5 picomolar, for the tyrosine kinase activity of the enzyme, based on an assay examining phosphorylation of a peptide derived from the phosphorylation site of the protein PLC gammal, a known EGFR phosphorylation substrate. This data is shown in Table 1.

Biological Data

Materials and Methods

*Purification of Epidermal Growth Factor Receptor Tyrosine Kinase*—Human EGF receptor tyrosine kinase was isolated from A431 human epidermoid carcinoma cells which overexpress EGF receptor by the following methods. Cells were grown in roller bottles in 50% Delbuco's Modified Eagle and 50% HAM F-12 nutrient media (Gibco) containing 10% fetal calf serum. Approximately $10^9$ cells were lysed in two volumes of buffer containing 20 mM 2-(4N-[2-hydroxyethyl]piperazin-1-yl)ethanesulfonic acid (hepes), pH 7.4, 5 mM ethylene glycol bis(2-aminoethyl ether) N,N,N',N'-tetraacetic acid, 1% Triton X-100, 10% glycerol, 0.1 mM sodium orthovanadate, 5 mM sodium fluoride, 4 mM pyrophosphate, 4 mM benzamide, 1 mM dithiothreitol, 80 µg/mL aprotinin, 40 µg/mL leupeptin and 1 mM phenylmethylsulfonyl fluoride. After centrifugation at 25,000×g for 10 minutes, the supernatant was equilibrated for 2 h at 4° C. with 10 mL of wheat germ agglutinin sepharose that was previously equilibrated with 50 mM Hepes, 10% glycerol, 0.1% Triton X-100 and 150 mM NaCl, pH 7.5, (equilibration buffer). Contaminating proteins were washed from the resin with 1M NaCl in equilibration buffer, and the enzyme was eluted with 0.5M N-acetyl-1-D-glucosamine in equilibration buffer, followed by 1 mM urea. The enzyme was eluted with 0.1 mg/ml EGF. The receptor appeared to be homogeneous as assessed by Coomassie blue stained polyacrylamide electrophoretic gels.

Determination of $IC_{50}$ values—enzyme assays for $IC_{50}$ determinations were performed in a total volume of 0.1 mL, containing 25 mM Hepes, pH 7.4, 5 mM $MgCl_2$, 2 mM $MnCl_2$, 50 µM sodium vanadate, 5–10 ng of EGF receptor tyrosine kinase, 200 μM of a substrate peptide, (Ac-Lys-His-Lys-Lys-Leu-Ala-Glu-Gly-Ser-Ala-Tyr$^{472}$-Glu-Glu-Val-NH$_2$, derived from the amino acid (Tyr$^{472}$ has been shown to be one of four tyrosines in PLC (phospholipaseC)-gamma 1 that are phosphorylated by the EGF receptor tyrosine kinase [Wahl, M. I.; Nishibe, S.; Kim, J. W.; Kim, H.; Rhee, S. G.; Carpenter, G., J. Biol. Chem., (1990), 265, 3944–3948.], and peptides derived from the enzyme sequence surrounding this site are excellent substrates for the enzyme.), 10 μM ATP containing 1 μCi of [$^{32}$P]ATP and incubated for ten minutes at room temperature. The reaction was terminated by the addition of 2 mL of 75 mM phosphoric acid and passed through a 2.5 cm phosphocellulose filter disc to bind the peptide. The filter was washed five times with 75 mM phosphoric acid and placed in a vial along with 5 mL of scintillation fluid (Ready gel Beckman).

TABLE 1

EGF Receptor Tyrosine Kinase Inhibition

| Example | IC$_{50}$ |
|---|---|
| 1 | 8 μM |
| 2 | 3.6 μM |
| 3 | 1.1 μM |
| 4 | 225 nM |
| 5 | 1.9 μM |
| 6 | 7.6 nM |
| 7 | 3.1 nM |
| 8 | 9.6 nM |
| 9 | 405 nM |
| 10 | 6.1 μM |
| 11 | 194 nM |
| 12 | 13 nM |
| 13 | 250 nM |
| 14 | 70 nM |
| 15 | 134 nM |
| 16 | 3.7 μM |
| 17 | 1.55 μM |
| 18 | 173 nM |
| 19 | 1.8 μM |
| 20 | 4.9 μM |
| 21 | 1.25 μM |
| 22 | 39 nM |
| 23 | 840 nM |
| 24 | 123 nM |
| 25 | 377 nM |
| 26 | 241 nM |
| 27 | 10 nM |
| 28 | 94 nM |
| 29 | 262 nM |
| 30 | 10 μM |
| 31 | 15 nM |
| 32 | 4.7 μM |
| 33 | 130 pM |
| 34 | 91 pM |
| 35 | 3.1 nM |
| 36 | 29 nM |
| 37 | 39 nM |
| 38 | 71 nM |
| 39 | 590 nM |
| 40 | 578 nM |
| 41 | 220 nM |
| 42 | 226 nM |
| 43 | 10 μM |
| 44 | 10 μM |
| 45 | 2.87 μM |
| 46 | 1.42 μM |
| 47 | 1.67 μM |
| 48 | 1.0 μM |
| 49 | 2.5 μM |
| 50 | 10 μM |
| 51 | 1.95 μM |
| 52 | 8 μM |
| 53 | 1.8 μM |
| 54 | 100 nM |
| 55 | 400 nM |

TABLE 1-continued

EGF Receptor Tyrosine Kinase Inhibition

| Example | IC$_{50}$ |
|---|---|
| 56 | 110 nM |
| 57 | 124 nM |
| 58 | 40 nM |
| 59 | 2.6 nM |
| 60 | 8 pM |
| 61 | 6 pM |
| 62 | 6.1 μM |
| 63 | 6.1 μM |
| 64 | 11 nM |
| 65 | 5.1 μM |
| 66 | 190 nM |
| 67 | 6.1 μM |
| 68 | 263 nM |
| 69 | 7.0 μM |
| 70 | 473 nM |
| 71 | 11 nM |
| 72 | 35 nM |
| 73 | 36 nM |
| 74 | 11.5 μM |
| 75 | 55 nM |
| 76 | 10 μM |
| 77 | 39 nM |
| 78 | 670 nM |
| 79 | 6.7 nM |

Cells

Swiss 3T3 mouse fibroblasts, A431 human epidermoid carcinoma cells, and MCF-7 (Michigan Cancer Foundation human mammary carcinoma cells), SK-BR-3 (human mammary carcinoma cells), MDA-MB-231 and MDA-MB-468 (human mammary carcinoma cells) breast carcinomas were obtained from the American Type Culture Collection, Rockville, Md. and maintained as monolayers in dMEM (Dulbecco's modified eagle medium)/F12, 50:50 (Gibco/BRL) containing 10% fetal bovine serum. To obtain conditioned medium, MDA-MB-231 cells were grown to confluency in an 850 cm$^2$ roller bottle and the medium replaced with 50 ml of serum-free medium. After 3 days the conditioned medium was removed, frozen down in aliquots and used as a heregulin source to stimulate erbB-2, 3, 4.

Antibodies

Monoclonal antibodies raised to the PDGF (platelet-desired growth factor) receptor or phosphotyrosine were from Upstate Biotechnology, Inc., Lake Placid, N.Y. Anti-pp39$^{jun}$ (antibody to the transcription factor c-jun, which is a 39 kDalton phosphoprotein) and anti-EGF receptor antibodies were from Oncogene Science, Uniondale, N.Y.

Immunoprecipitation and Western Blot

Cells were grown to 100% confluency in 100 mm Petrie dishes (Corning). After the cells were treated for 5 minutes with either EGF (epidermal growth factor), PDGF, or bFGF (basic fibroblast growth factor) (20 ng/ml) or 1 ml of conditioned media from MDA-MB-231 cells, the media was removed and the monolayer scraped into 1 ml of ice cold lysis buffer (50 mM Hepes, pH 7.5, 150 mM NaCl, 10% glycerol, 1% triton X-100, 1 mM EDTA, 1 mM EGTA, 10 mM sodium pyrophosphate, 30 mM p-nitrophenyl phosphate, 1 mM orthovanadate, 50 mM sodium fluoride, 1 mM phenylmethylsulfonylfluoride, 10 μg/ml of aprotinin, and 10 μg/ml of leupeptin). The lysate was transferred to a microfuge tube (small centrifuge that holds 1–2 ml plastic centrifuge tubes), allowed to sit on ice 15 minutes and centrifuged 5 minutes at 10,000×g. The supernatant was transferred to a clean microfuge tube and 5 μg of antibody was added to designated samples. The tubes were rotated for 2 hours at 4° C. after which 25 µl of protein A sepharose was added and then rotation continued for at least 2 more hours. The protein A separose was washed 5 times with 50 mM Hepes, pH 7.5, 150 mM NaCl, 10% glycerol and 0.02% sodium azide. The precipitates were resuspended with 30 µl of Laemlli buffer (Laemmli, NATURE, Vol. 727, pp. 680–685, 1970), heated to 100° C. for 5 minutes and centrifuged to obtain the supernatant. Whole cell extracts were made by scraping cells grown in the wells of 6 well plates into 0.2 ml of boiling Laemmli buffer. The extract were transferred to a microfuge tube and heated to 100° C. for 5 minutes. The entire supernatant from the immunoprecipitation or 35 µl of the whole cell extract was loaded onto a polyacrylamide gel (4–20%) and electrophoresis carried out by the method of Laemlli (Laemmli, 1970). Proteins in the gel were electrophoretically transferred to nitrocellulose and the membrane was washed once in 10 mM Tris buffer, pH 7.2, 150 mM NaCl, 0.01% Azide (TNA) and blocked overnight in TNA containing 5% bovine serum albumin and 1% ovalbumin (blocking buffer). The membrane was blotted for 2 hours with the primary antibody (1 µg/ml in blocking buffer) and then washed 2 times sequentially in TNA, TNA containing 0.05% Tween-20 and 0.05% Nonidet P-40 (commercially available detergent) and TNA. The membranes were then incubated for 2 hours in blocking buffer containing 0.1 µCi/ml of [$^{125}$I] protein A and then washed again as above. After the blots were dry they were loaded into a film cassette and exposed to X-ARX-ray film for 1–7 days. Protein A is a bacterial protein that specifically bonds certain IgG subtypes and is useful in binding to and isolating antibody-antigen complexes.

Northern Blots

Total cellular RNA was isolated from untreated control or treated Swiss 3T3 cells using RNAzol-B (trademark of Tel Test Inc. for a kit used to isolate RNA from tissues) and adhered to the protocol described by the manufacturer. Forty to fifty µg of RNA was loaded onto a 1% agarose gel and electrophoresis carried out for 3–4 hours at 65 volts. The RNA in the gel was transferred by capillary action to a nylon membrane (Hybond-N, Amersham). The 40 mer c-jun probe was end labeled with [$^{32}$P]ATP using T4 nucleotide kinase (Promega) and purified on a G25 sephadex column according to the procedure recommended by the supplier, Oncogene Science. Hybridization was performed overnight at 65° C. (c-jun is an immediate early transcription factor; it is one of the components of AP-1 while FOS is the second component of AP-1.

Growth Factor-Mediated Mitogenesis

Swiss 3T3 fibroblasts were grown to 90–100% confluency in 24- well plates (1.7×1.6 cm, flat bottom) and growth arrested in serum-free media for 18 hours. Drug was added to specified wells 2 hours prior to growth factors and then the cells were exposed to either 20 ng/ml EGF, PDGF or bFGF or 10% serum for 24 hours. Two µCi of [methyl-$^{3}$H] thymidine was added to each well and incubated for 2 hours at 37° C. The cells were trypsinized and injected into 2 ml of ice cold 15% trichloroacetic acid (TCA). The resulting precipitate was collected on glassfiber filters, washed five times with 2-ml aliquots of ice-cold 15% TCA, dried and placed in scintillation vials along with 10 ml Ready gel (Beckman, Irvine, Calif.). Radioactivity was determined in a Beckman LS 6800 scintillation counter.

Growth Inhibition Assay

Cells (2×10$^{4}$) were seeded in 24-well plates (1.7×1.6 cm, flat bottom) in two mls of medium with or without various concentrations of drug. Plates were incubated for 3 days at 370° in a humidified atmosphere containing 5% $CO_2$ in air. Cell growth was determined by cell count with a Coulter Model AM electronic cell counter (Coulter Electronics, Inc., Hialeah, Fla.).

INHIBITION OF EGF-INDUCED AUTOPHOSPHORYLATION IN A431 EPIDERMOID CARCINOMA CELLS AND CONDITIONED MEDIA-INDUCED AUTOPHOSPHORYLATION IN SK-BR-3 BREAST TUMOR CELLS BY COMPOUNDS OF THE CURRENT INVENTION

| Example # | EGFR $IC_{50}$ nM | A431 $IC_{50}$ nM | SKBR-3 $IC_{50}$ nM |
| --- | --- | --- | --- |
| 4 | 225 | >1000 | >10,000 |
| 6 | 7.6 | 53 | 2660 |
| 7 | 3.1 | 20 | 100 |
| 8 | 9.6 | 32 | 71 |
| 22 | 39 | 252 | ~1500 |
| 27 | 10 | 110 | ~800 |
| 59 | 2.6 | 12 | <10 |
| 60 | 0.008 | 13 | <10 |
| 61 | 0.006 | 21 | 39 |
| 70 | 11 | 124 | <10 |
| 74 | 55 | >1000 | >1000 |

ANTIPROLIFERATIVE PROPERTIES OF TYROSINE KINASE INHIBITORS $IC_{50}$ (nM)

|  | Ex 60 | Ex 61 |
| --- | --- | --- |
| B104-1-1 | 2100 | 1000 |
| SK-BR-3 | 600 | 900 |
| MDA-468 | 3000 | 12000 |

Figure 7:
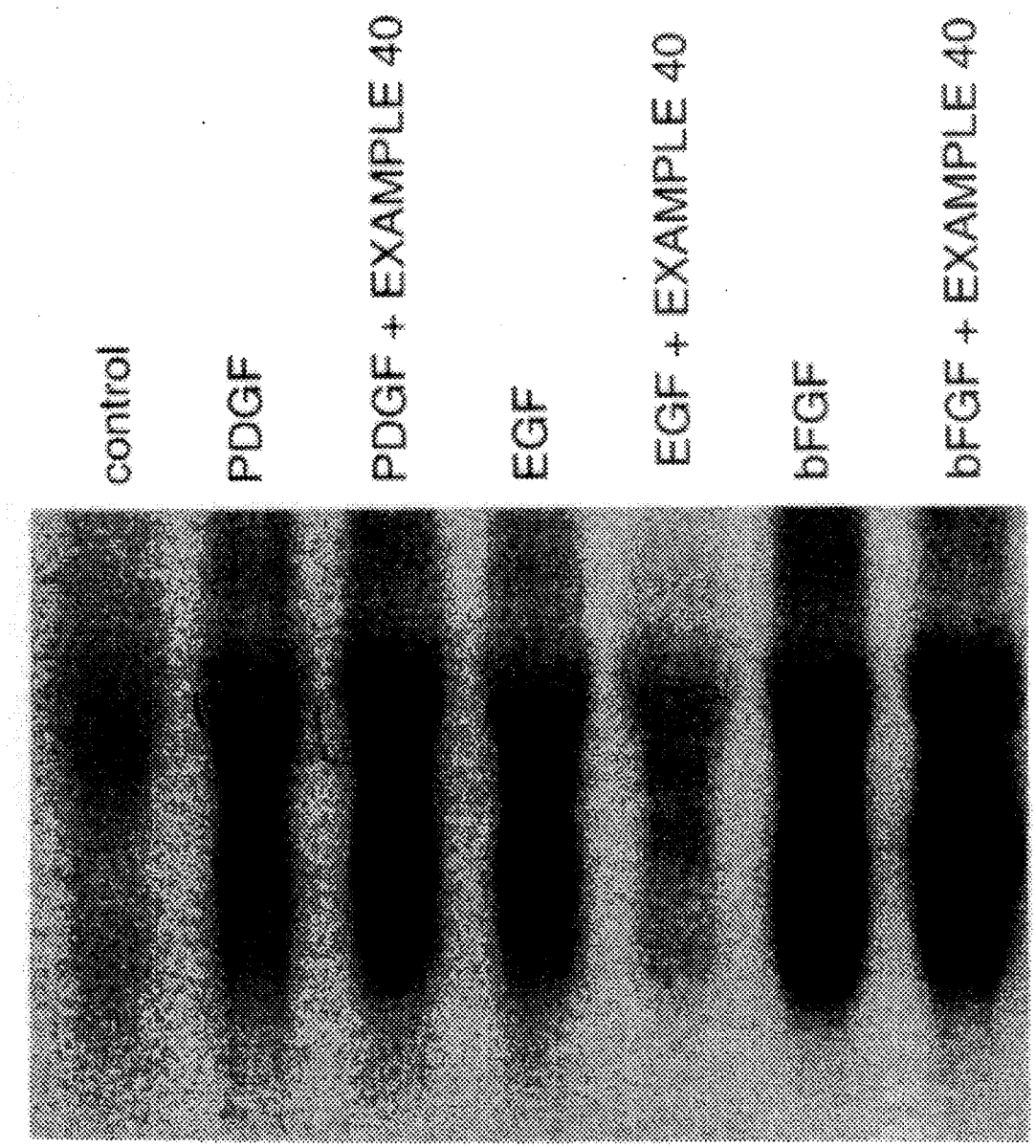
FIG. 7 is an effect of Example 40 on growth factor dependent expression of c-jun mRNA in Swiss 3T3 mouse fibroblasts.
Figure 8A:
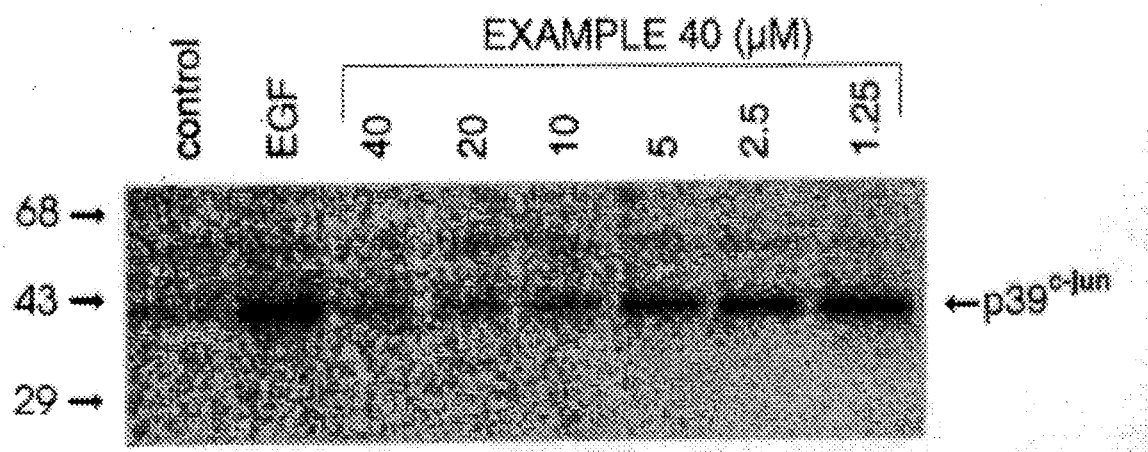
FIG. 8 is an effect of Example 40 on growth factor mediated expression of $p39^{c-jun}$.
Figure 8B:
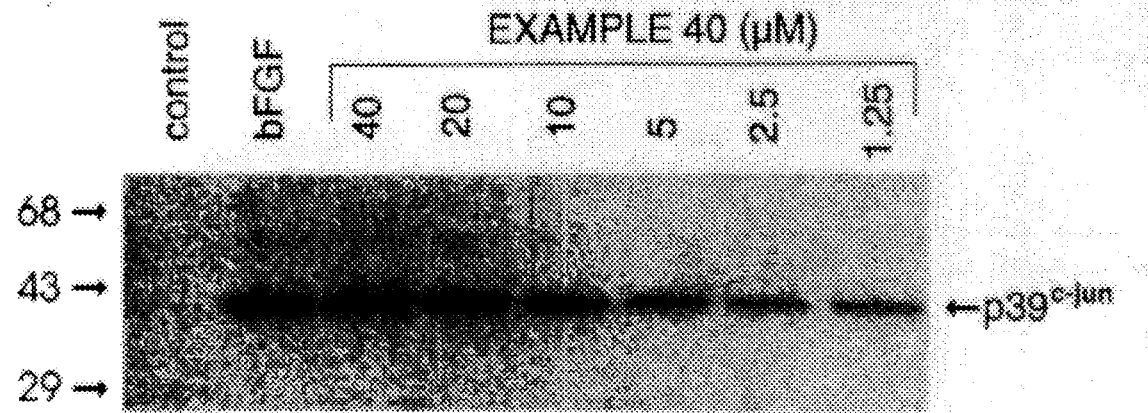
Figure 8C:
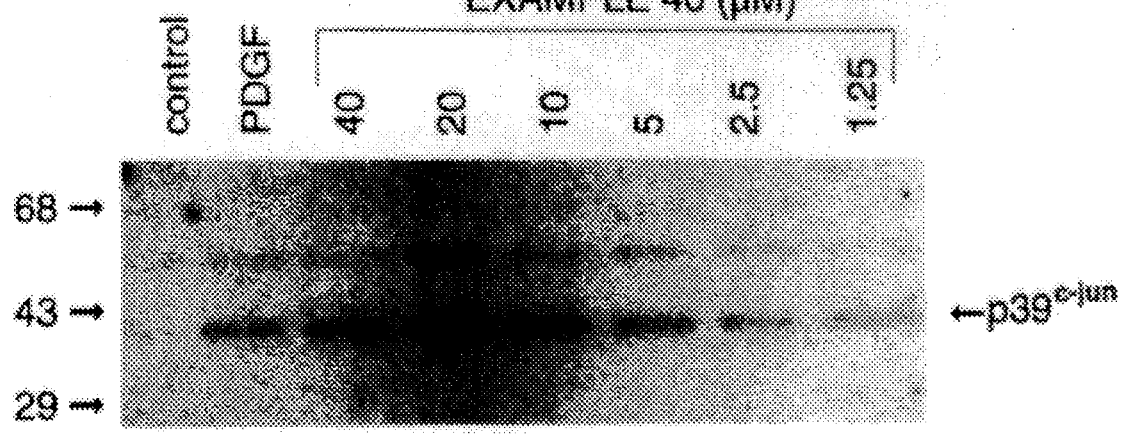
Figure 9:
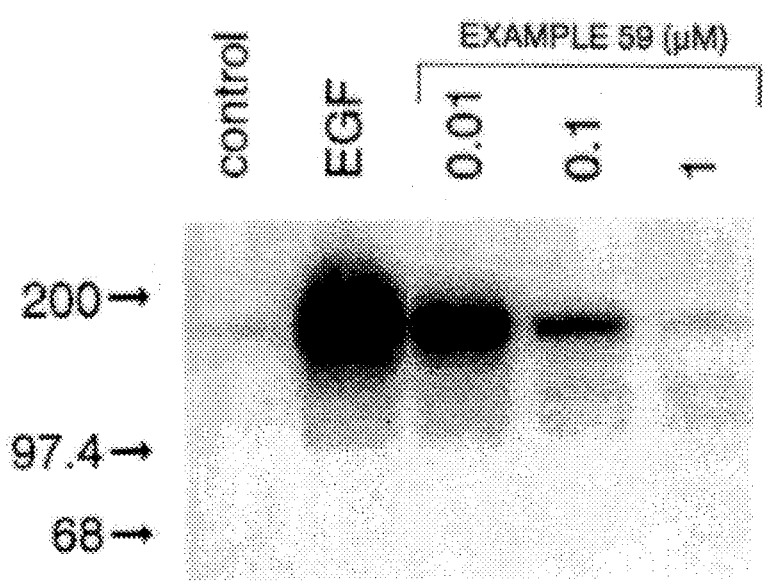
FIG. 9 is an effect of Example 59 of EGF receptor autophosphorylation in A431 human epidermoid carcinoma.
Figure 10:
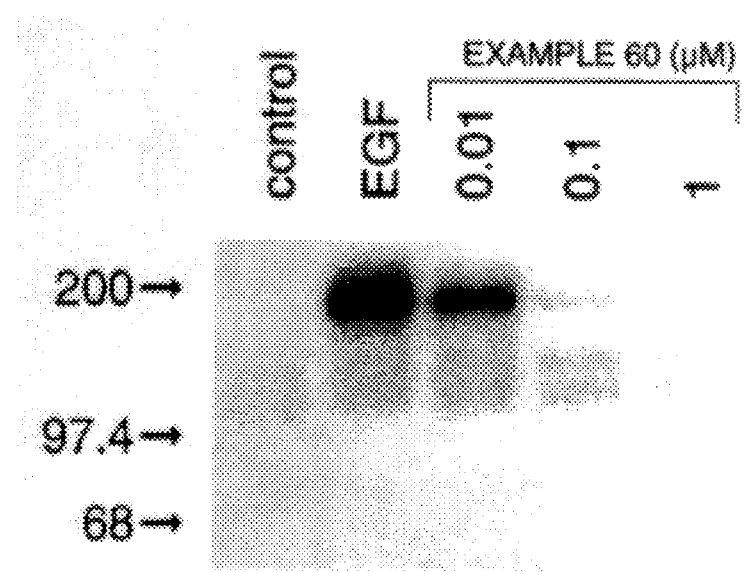
FIG. 10 is an effect of Example 60 on EGF receptor autophosphorylation in A431 human epidermoid carcinoma.
Figure 11:
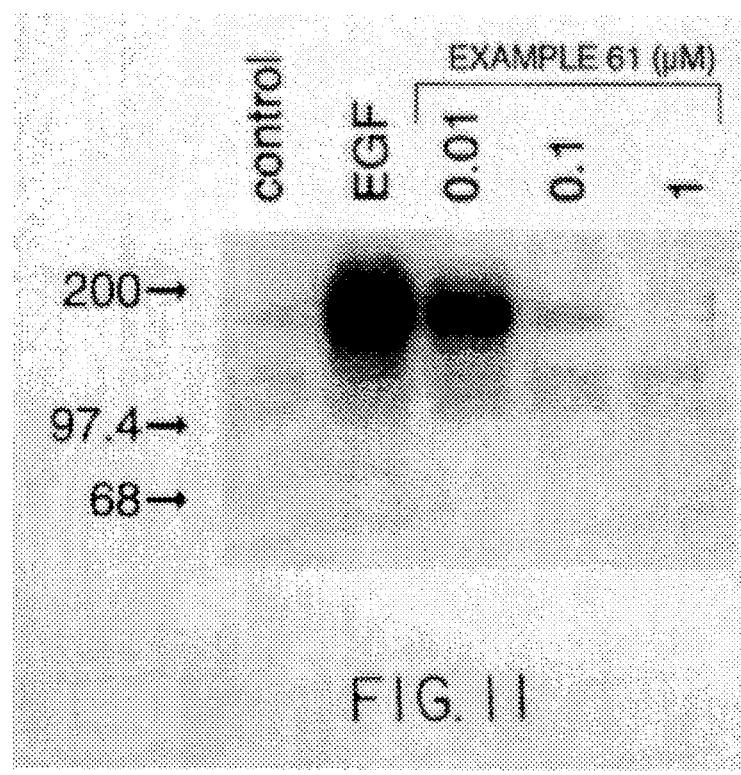
FIG. 11 is an effect of Example 61 on EGF receptor autophosphorylation in A431 human epidermoid carcinoma.
Figure 12:
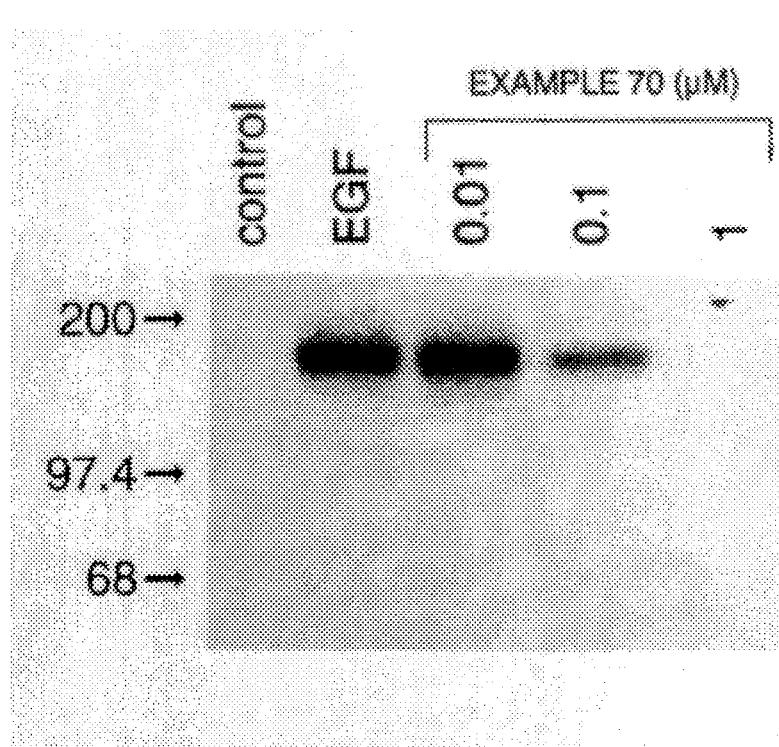
FIG. 12 is an effect of Example 70 on EGF receptor autophosphorylation in A431 human epidermoia carcinoma.
Figure 13:
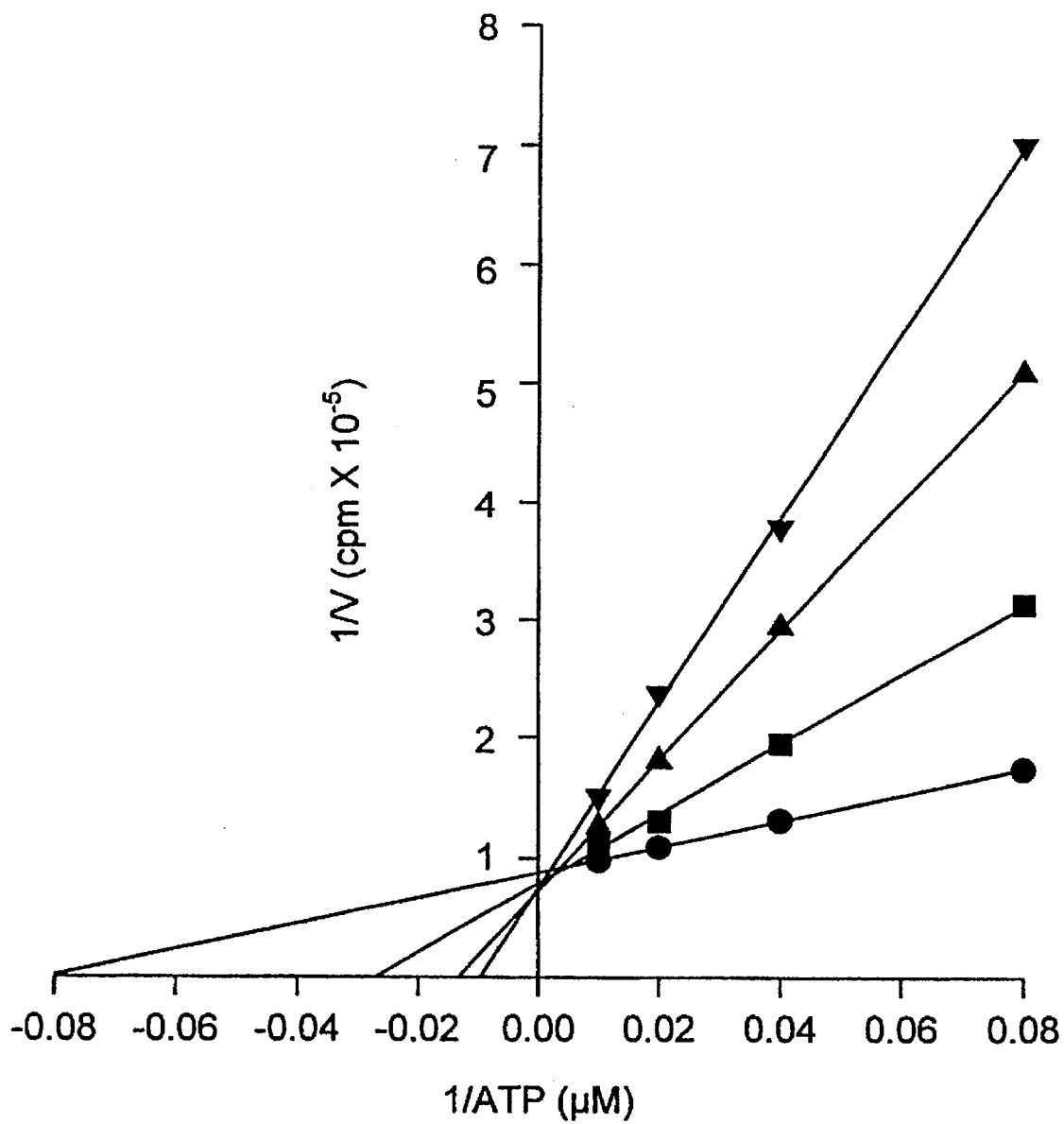
FIG. 13 is a chart showing an inhibition of EGF receptor tyrosine kinase by Example 27.
Figure 14:
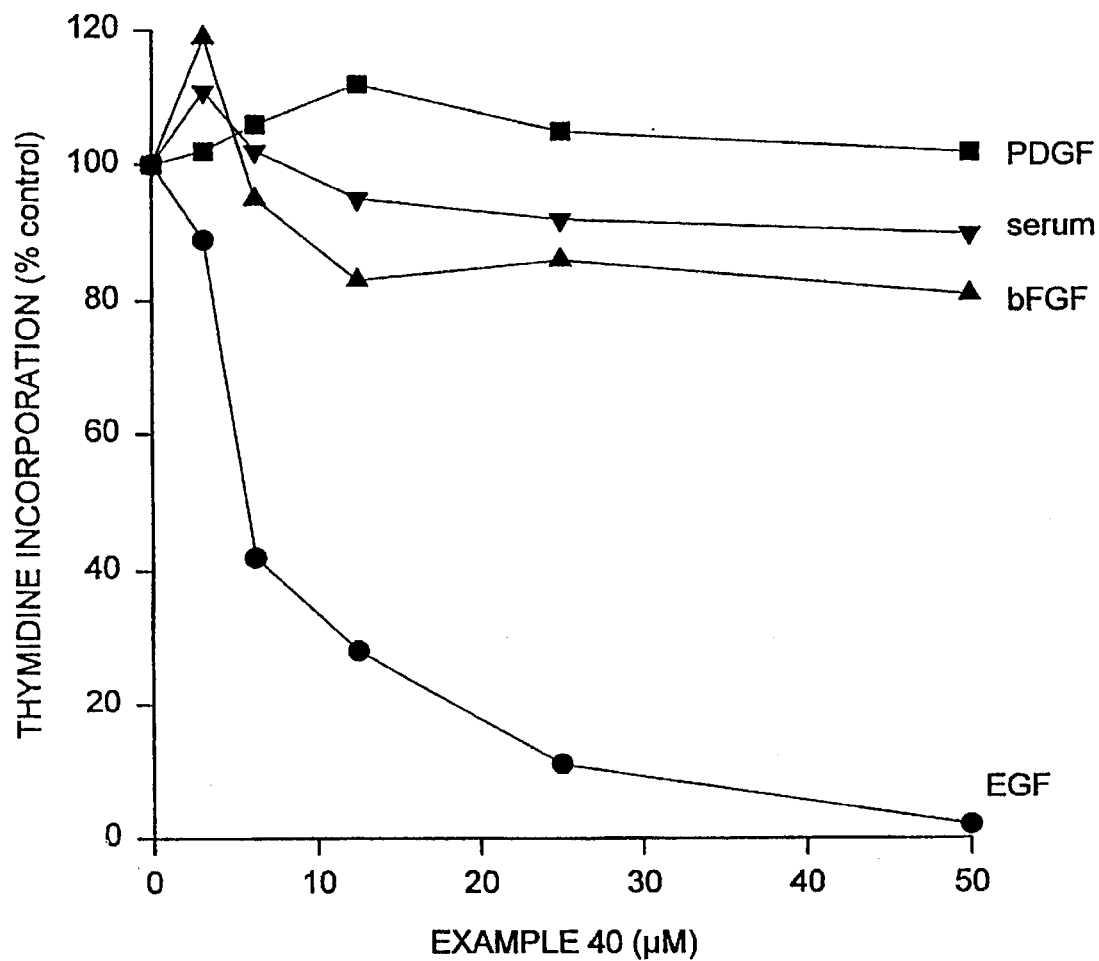
FIG. 14 is a graph showing an effect of Example 40 on growth factor-mediated mitogenesis in Swiss 3T3 murine fibroblasts.
Figure 15:
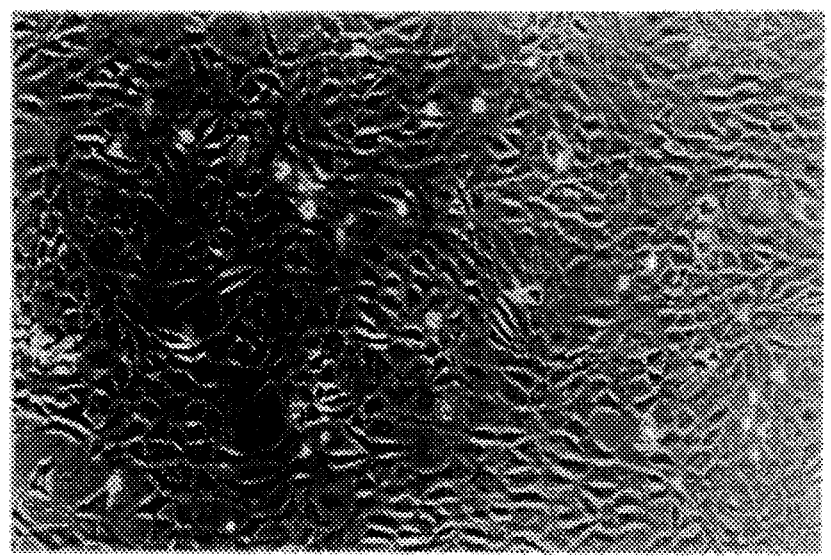
FIG. 15 is a photograph of an NIH 3T3 mouse fibroblast line, transfected with the human EGFR gene showing a normal flattened morphology.
Figure 16:
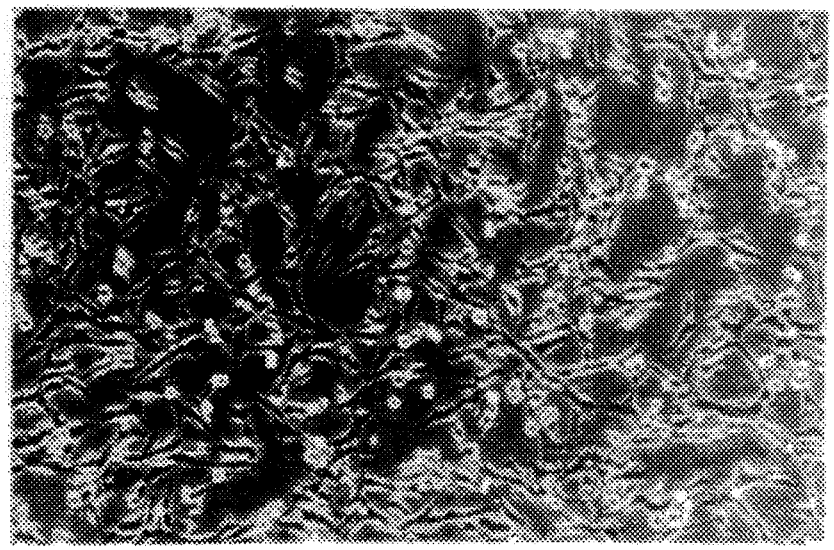
FIG. 16 is a photograph of the same cell line treated with 100 ng/mL of EGF showing a typical spindly transformed morphology.
Figure 17:
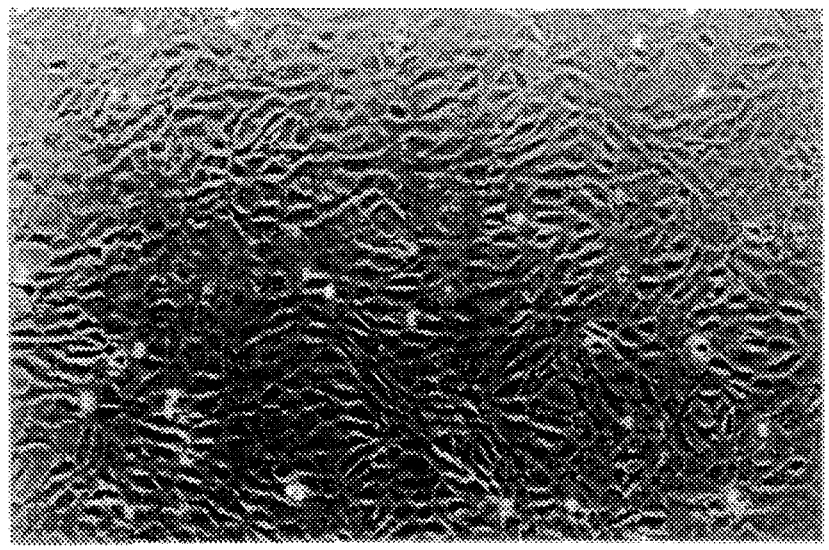
FIG. 17 is a photograph of the same cell line in the presence of both 100 ng/mL of EGF and 5 μm of Example 27 showing the morphology reverted from the transformed type back to the normal type.

B104-1-1—NIH-3T3 fibroblasts transfected by the neu oncogene, Stem et al., Science, 234, pp. 321–324 (1987)
SK-BR-3—Human breast carcinoma overexpressing erbB-2 and erbB-3
MDA-468—Human breast carcinoma overexpressing the EGF receptor The above gels, developed as detailed in the experimental section, demonstrate the efficacy of compounds of the current invention at blocking certain EGF-stimulated mitogenic signalling events in whole cells. The numbers to the left of the gels indicated the positions of molecular weight standards in kiloDaltons. The lane labelled control shows the degree of expression of the growth-related signal in the absence of EGF stimulation, whereas the lane labelled EGF (or PDGF or b-FGF) shows the magnitude of the growth factor-stimulated signal. The other lanes show the effect of the stated quantities of the named drug on the growth factor-stimulated activity being measured, demonstrating that the compounds of the present invention have potent effects in whole cells, consistent with their ability to inhibit the tyrosine kinase activity of the EGF receptor. Gel of Example 40 (FIG. 7) detects mRNA for c-jun by hybridization with a specific radiolabelled RNA probe for c-jun. The gel demonstrates that the growth factors EFG, PDGF and b-FGF stimulate c-jun production in Swiss 3T3 cells, and that compound 40 blocks this production for EGF-stimulated cells, but not for PDGF or b-FGF stimulated cells.

Effect of Example 40 on Growth Factor Mediated Expression of $p39^{c\text{-}jun}$ This gel shows the amount of c-jun induced in Swiss 3T3 cells by the growth factor EGF, PDGF and b-FGF, quantitating with an anti-c-jun-specific monoclonal antibody. It demonstrates the ability of Example 40 to block c-jun expression in Swiss 3T3 when stimulated by EGF, but not when stimulated by PDGF or b-FGF.

It is to be appreciated that the compounds described herein can be used in combination with other components to enhance their activity. Such additional components are anti-neoplastic materials as, doxorubicin, taxol, cis platin, and the like.

It has been found that the compounds described herein may inhibit both the erb-B2 and erb-B4 receptors and therefore have significantly increased clinical activity advantageously in combination with the aforementioned anti-neoplastic agents.

See also the results shown in FIGS. 1–17.

Some preferred structures are as follows:

| Ex # | Z |
|---|---|
| 4 | -fluorine |
| 6 | —NH$_2$ |
| 7 | —NHCH$_3$ |
| 8 | —N(CH$_3$)$_2$ |

| Ex # | Z | R$_2$ |
|---|---|---|
| 22 | NH$_2$ | —NO$_2$ |
| 27 | NH$_2$ | Br |

| Ex # | Z | R$_2$ |
|---|---|---|
| 59 | —OCH$_3$ | Br |
| 60 | —NHCH$_3$ | Br |
| 61 | —N(CH$_3$)$_2$ | Br |

Chemical Experimental

Listed below are preferred embodiments wherein all temperatures are in degrees Centigrade and all parts are parts by weight unless otherwise indicated.

EXAMPLE 1

4-Anilinopyrido[3,2-d]pyrimidine mesylate

3H-Pyrido[3,2-d]pyrimidin-4-one. A solution of 6-chloro-3-nitropicolinamide (2.00 g, 9.91 mmol) in EtOAc/MeOH (1:1, 100 mL) is hydrogenated over 5% Pd-C (0.40 g) at 60 psi for 6 days, with additions of fresh catalyst after 2 and 4 days. After removal of the catalyst by filtration the solution is concentrated to dryness, to give 3-aminopicolinamide as an orange oil, which is used directly in the next step. The crude product is stirred under reflux with triethyl orthoformate (50 mL) for 42 h, during which time a tan precipitate forms. After cooling, the solid is filtered off, washed well with petroleum ether, and dried under vacuum to give 3H-pyrido[3,2-d]pyrimidin-4-one (1.27 g, 87%), mp 343°–345° C. [Price, C. C. and Curtin, D. Y. J. Amer. Chem. Soc. 68, 914, 1946 report mp 346°–347° C.].

4-Chloropyrido[3,2-d]pyrimidine. A suspension of the above pyrimidinone (1.00 g, 6.80 mmol) in POCl$_3$ (30 mL) is heated under reflux for 4 h, and then concentrated to dryness under reduced pressure. The residue is partitioned between CH$_2$Cl$_2$ and saturated NaHCO$_3$ solution, and the organic layer worked up to give 4-chloropyrido[3,2-d]pyrimidine (0.97 g, 86%) as a tan solid, mp 335° C. (dec), which is used without further characterisation.

4-Anilinopyrido[3,2-d]pyrimidine mesylate. A solution of 4-chloropyrido[3,2-d]pyrimidine (84 mg, 0.5 mmol), aniline (56 mg, 0.6 mmol) and triethylamine (62 mg, 0.6 mmol) in EtOH (2 mL) are refluxed under N$_2$ with stirring for 2 h. The crude reaction mixture is purified on a preparative tlc plate (silica), eluting once with 3% MeOH in CHCl$_3$. The major band is extracted, and evaporated to dryness under reduced pressure, and the residual solid is dissolved in acetone, (5 mL), filtered, and methanesulfonic acid (32 μL, 0.5 mmol) is added slowly with swirling. The precipitate is collected by suction filtration, rinsed with acetone and dried in a vacuum oven to give 4-anilinopyrido[3,2-d]pyrimidine mesylate (91 mg, 57%) as dull yellow needles. $^1$H NMR (DMSO) δ 11.75 (1H, slbrs), 9.11 (1H, dd, J=1.5, 4.3 Hz), 8.97 (1H, s), 8.32 (1H, dd, J=1.5, 8.4 Hz), 8.12 (1H, dd, J=4.3, 8.5 Hz), 7.88 (2H, d, J=8.2 Hz), 7.49 (2E, t, J=8.0 Hz), 7.32 (1H, t, J=7.0 Hz), 2.34 (3H, s).

EXAMPLE 2

4-Benzylaminopyrido[3,2-d]pyrimidine

A solution of freshly prepared 4-chloropyrido[3,2-d]pyrimidine (0.10 g, 0.60 mmol) (prepared as described in the previous experimental) and benzylamine (0.13 mL, 1.20 mmol) in propan-2-ol (15 mL) containing a trace of conc. HCl is warmed at 50° C. for 30 min, and then concentrated to dryness. The residue is partitioned between water and EtOAc, and the organic layer worked up and chromatographed on silica gel. EtOAc elutes foreruns, while MeOE/EtOAc (1:9) elutes 4-(benzylamino) pyrido [3,2-d] pyrimidine (0.11 g, 77%). $^1$H NMR (CDCl$_3$) δ 8.67 (1H, s), 6.50 (1H, dd, J=4.3, 1.5 Hz), 8.10 (1H, dd, J=8.5, 1.5 Hz), 7.63 (1H, dd, J=8.8, 4.3 Hz), 7.55 (1H, brs), 7.41–7.29 (5H, m), 4.86 (2H, d, J=5.9 Hz).

EXAMPLE 3

4-(3-Bromoanilino)pyrido[3,2-d]pyrimidine

Reaction of 4-chloropyrido[3,2-d]pyrimidine (prepared as described in a previous experimental) with 3-bromoaniline in propan-2-ol containing a trace of conc. HCl at 50° C. for 30 min, followed by chromatography of the product on silica gel, gives 4-(3-bromophenyl) aminopyrido[3,2-d] pyrimidine (87% yield). $^1$H NMR (CDCl$_3$) δ 9.19 (1H, brs), 8.83 (1H, s), 8.80 (1H, dd, J=4.3, 1.5 Hz), 8.29 (1H, brs), 8.19 (1H, dd, J=8.5, 1.5 Hz), 7.83 (1H, m), 7.76 (1H, dd, J=8.5, 4.3 Hz), 7.29–7.27 (2H, m).

EXAMPLE 4

4-(3-Bromoanilino)-6-fluoropyrido[3,2-d]pyrimidine 2-cyano-6-fluoro-3-nitropyridine. A mixture of 6-chloro-2-cyano-3-nitropyridine [Colbry, N. L.; Elslager, E. F.;

Werbel, L. M.; *J. Het. Chem.*, 1984, 21, 1521–1525] (10.0 g, 0.054 mol) and KF (9.48 g, 0.163 mol) in MeCN (200 mL) is heated under reflux with stirring for 18 h, then poured into water and extracted with EtOAc. The extract is washed with water and worked up, and the residue is chromatographed on silica gel, eluting with EtOAc/petroleum ether (3:7), to give after removal of the solvent under reduced pressure 2-cyano-6-fluoro-3-nitropyridine (7.2 g, 79%). $^1$H NMR (CDCl$_3$) δ 8.79 (1H, dd, J=9.0, 6.0 Hz), 7.48 (1H, dd, J=9.0, 3.0 Hz).

6-Fluoro-3-nitropyridine-2-carboxamide. A solution of 2-cyano-6-fluoro-3-nitropyridine (1.40 g, 8.39 mmol) in 90% H$_2$SO$_4$ (30 mL) is warmed at 70° C. for 90 min, then cooled, poured onto ice and basified with conc. ammonia. Extraction with EtOAc and workup gives 6-fluoro-3-nitropyridine-2-carboxamide (0.94 g, 61%). $^1$HNMR (CDCl$_3$) δ 8.70 (1H, dd, J=8.9, 6.5 Hz), 8.30, 8.03 (1H, 1H, brs), 7.62 (1H, dd, J=8.9, 2.9 Hz).

6-Fluoro-3H-pyrido[3,2-d]pyrimid-4-one. A solution of 6-fluoro-3-nitropyridine-2-carboxamide (1.50 g, 8.10 mmol) in EtOAc (80 mL) is hydrogenated over 5% Pd-C (0.30 g) at 60 psi for 2 h. After removal of the catalyst by filtration, the solvent is removed under reduced pressure, to give a residue of crude 3-amino-6-fluoropyridine-2-carboxamide which is used directly in the next step. Triethyl orthoformate (60 mL) is added and the mixture is then heated under reflux with vigorous stirring for 18 h. The cooled mixture is diluted with an equal volume of petroleum ether, and the resulting precipitate collected by filtration and is washed well with petroleum ether to give 6-fluoro-3H-pyrido[3,2-d]pyrimid-4-one (1.26 g, 84%). $^1$H NMR (DMSO) δ 12.72 (1H, brs), 8.31 (1H, dd, J=8.6, 7.7 Hz), 8.20 (1H, s), 7.66 (1H, dd, J=8.6, 3.0 Hz).

4-(3-Bromoanilino)-6-fluoropyrido[3,2-d)pyrimidine. A suspension of 6-fluoro-3H-pyrido[3,2-d]pyrimid-4-one (0.20 g, 1.21 mmol) in POCl$_3$ (30 mL) is heated under reflux with stirring until homogeneous (2 h), and then for a further 1 h. Excess POCl$_3$ is removed under reduced pressure, and the residue is partitioned between CH$_2$Cl$_2$ and saturated aqueous NaHCO$_3$. Workup of the organic portion gives crude 4-chloro-6-fluoropyrido[3,2-d]pyrimidine (100%) as an unstable white solid which is used directly in the next step.

A solution of 4-chloro-6-fluoropyrido[3,2-d]pyrimidine (0.20 g, 1.1 mmol) and 3-bromoaniline (0.12 mL, 2.18 mmol) in propan-2-ol (20 mL) containing conc. HCl (1 drop) is heated under reflux for 15 min, then cooled, poured into water and extracted with EtOAc. The extract is worked up, and the residue chromatographed on silica gel, eluting with EtOAc/petroleum ether (1:2)to give after removal of the solvent under reduced pressure 4-(3-bromoanilino)-6-fluoropyrido[3,2-d)pyrimidine (0.18 g, 52%). $^1$H NMR (CDCl$_3$) δ 8.82 (1H, s), 8.65 (1H, brs), 8.31 (1H, t, J=7.4 Hz), 8.27 (1H, brs), 7.77 (1H, m) 7.41 (1H, dd, J=8.9, 2.2 Hz), 7.29 (2H, brs).

EXAMPLE 5

4-(3-Bromoanilino)-6-chloropyrido[3,2-d] pyrimidine 6-chloro-3-nitropicolinamide. A solution of 6-chloro-3-nitropicolinonitrile (1.00 g, 5.45 mmol) in 90% H$_2$SO$_4$ (15 mL) is warmed at 70° C. for 3.5 h, and then poured into ice-water. The mixture is extracted four times with EtOAc and the combined extracts worked up to give 6-chloro-3-nitropicolinamide (0.80 g, 73%). $^1$H NMR (DMSO) δ 8.55 (1H, d, J=8.5 Hz), 8.31, 8.04 (1H, 1H, 2 brs), 7.93 (1H, d, J=8.5 Hz).

6-Chloro-3H-pyrido[3,2-d)pyrimidin-4-one. A solution of 6-chloro-3-nitropicolinamide (0.30 g, 1.49 mmol) in EtOAc (30 mL) is hydrogenated at 60 psi over 5% Pd-C (0.10 g) for 20 min. After removal of the catalyst by filtration the solution is concentrated to dryness to give 3-amino-6-chloropicolinamide as a yellow oil, which is used directly in the next step. It is dissolved in triethylorthoformate (30 mL) and the mixture is heated under reflux for 18 h. Petroleum ether (30 mL) is added to the cooled solution, and the resulting precipitate of crude 6-chloro-3H-pyrido[3,2-d) pyrimidin-4-one (0.27 g, 99%) is filtered off and dried in a vacuum oven.

4-(3-Bromoanilino)-6-chloropyrido[3,2-d]pyrimidine. A suspension of the above quinazolone (0.20 g, 1.10 mmol) in POCl$_3$ (30 mL) is heated under reflux for 3 h, and then concentrated to dryness under reduced pressure. The residue is partitioned between CH$_2$Cl$_2$ and saturated NaHCO$_3$ solution; and the organic portion is worked up to give 4,6-dichloropyrido[3,2-d]pyrimidine (0.16 g, 73%) as a tan solid, which is used directly in the next step. A solution of the crude dichloropyridopyrimidine (0.16 g, 0.80 mmol) and 3-bromoaniline (0.17 mL, 1.60 mmol) in propan-2-ol (25 mL) containing a trace of conc. HCl is warmed at 50° C. for 30 min. The cooled mixture is poured into saturated NaHCO$_3$ and extracted with EtOAc, and the extract is worked up and chromatographed on silica gel. Elution with EtOAc/petroleum ether (1:4) gives 3-bromoaniline, while EtOAc/petroleum ether (1:1) elutes 4-(3-bromoanilino)-6-chloropyrido[3,2-d]pyrimidine (0.17 g, 63%). $^1$H NMR (CDCl$_3$) δ 8.90 (1H, brs,) 8.84 (1H, s), 8.30 (1H, dd, J=2.1, 2.0 Hz) 8.17 (1H, d, J=8.8 Hz), 7.82–7.78 (1H, m) 7.73 (1H, d, J=8.8 Hz), 7.32–7.29, (2H, m).

EXAMPLE 6

4-(3-Bromoanilino)-6-aminopyrido[3,2-d]pyrimidine

Reaction of 4-(3-bromoanilino)-6-fluoropyrido [3,2-d) pyrimidine (0.12 g, 0.38 mmol) (described in a previous experimental) with a saturated solution of ammonia in ethanol in a pressure vessel at 100° C. for 18 h gives 6-amino-4-(3-bromoanilino)pyrido[3,2-d]pyrimidine, (87 mg, 72%). $^1$ H NMR (CDCl$_3$) δ 8.76 (1H, brs), 8.64 (1H, s), 8.23 (1H, brs), 7.93 (1H, d, J=9.0 Hz), 7.81 (1H, dt, J$_d$=7.7 Hz, J$_f$=1.8 Hz), 7.28–7.22 (2H, m), 7.00 (1H, d, J=9.0 Hz), 4.90 (2H, brs).

EXAMPLE 7

4-(3-Bromoanilino)-6-methylaminopyrido[3,2-d] pyrimidine

Reaction of 4-(3-bromoanilino)-6-fluoropyrido[3,2-d) pyrimidine (50 mg, 0.16 mmol) (described in a previous experimental) with methylamine hydrochloride (32 mg, 0.47 mmol) and triethylamine (70 μL, 0.55 mmol) in ethanol (10 mL) in a pressure vessel at 100° C. for 18 h gives 6-methylamino-4-(3-bromoanilino)pyrido[3,2-d]pyrimidine (43 mg, 81%). $^1$H NMR (CDCl$_3$) δ 8.81 (1H, brs), 8.61 (1H, s), 8.19 (1H, t, J=1.8 Hz), 7.86 (1H, d, J=9.1 Hz,), 7.83 (1H, dt, J$_d$=7.7 Hz, J$_f$=1.8 H), 7.28–7.21 (2H, m), 6.92 (1H, d, J=9.1 Hz), 4.97 (1H, q, J=5.0 Hz), 3.13 (3H, d, J=5.0 Hz).

EXAMPLE 8

4-(3-Bromoanilino)-6-dimethylaminopyrido[3,2-d] pyrimidine

A mixture of 4-(3-bromoanilino)-6-fluoropyrido[3,2-d) pyrimidine (0.15 g, 0.47 mmol) (described in a previous experimental), dimethylamine hydrochloride (0.11 g, 1.41 mmol) and triethylamine (0.23 mL, 1.64 mmol) in EtOH (15 mL) is heated in a pressure vessel at 100° C. for 18 h. The solvent is removed under reduced pressure, and the residue is partitioned between EtOAc and water. The organic portion is worked up, and the residue chromatographed on silica gel. Elution with EtOAc/petroleum ether (1:1) gives foreruns, while EtOAc elutes off 4-(3-bromoanilino)-6-dimethylaminopyrido[3,2-d]pyrimidine (0.14 g, 86%). $^1$HNMR (CDCl$_3$) δ 8.72 (1H, brs), 8.56 (1H, s), 8.17 (1H, t, J=1.9 Hz), 7.85 (1H, d, J=9.3 Hz), 7.77 (1H, dt, J$_d$=7.5 Hz, J$_f$=1.9 Hz), 7.27–7.18 (2H, m), 7.08 (1H, d, J=9.3 Hz), 3.21 (6H, s).

EXAMPLE 9

4-(3-Bromoanilino)-6-methoxypyrido[3,2-d]pyrimidine 4-(3-Bromoanilino)-6-fluoropyrido[3,2-d]pyrimidine (described in a previous experimental) (0.11 g, 0.34 mmol) is added to a solution of NaOMe (prepared by the addition of Na metal (31 mg, 1.38 mmol) to dry MeOH (15 mL). After heating in a pressure vessel at 90° C. for 3 h, the solution is concentrated to dryness and the residue is partitioned between EtOAc and water. Workup of the organic portion gives 4-(3-bromophenyl) amino-6-methoxypyrido [3,2-d]pyrimidine (92 mg, 82%). $^1$H NMR (CDCl$_3$) δ 8.73 (1H, s), 8.66 (1H, brs), 8.18 (1H, m), 8.05 (1H, d, J=8.9 Hz), 7.83–7.80 (1H, m), 7.30–7.24 (2Ht, m), 7.23 (1H, d, J=8.9 Hz), 4.12 (3H, s).

EXAMPLE 10

4-Anilinopyrido[4,3-d]pyrimidine 4-(N-t-Butoxycarbonylamino)pyridine. To a mixture of 4-aminopyridine (2 g, 21.24 mmol), potassium hydroxide (3.57 g, 63.72 mmol), water (10 mL), and 2-methyl-2-propanol (4 mL) on ice is added di-t-butyl-dicarbonate (6.95 g, 31.87 mmol). The resulting biphasic solution is stirred at 25° C. for 1 week, then water (20 mL) is added. The solution is extracted with 1X CH$_2$Cl$_2$ and 2X EtOAc. The organic layer is dried (MgSO$_4$) and concentrated under reduced pressure to give 4-(N-t-butoxycarbonylamino)pyridine (4.08 g, 99%). $^1$H NMR (DMSO) δ 9.84 (1H, s), 8.35 (2H, d, J=6 Hz), 7.44 (2H, d, J=7 Hz), 1.49 (9H, s).

4-(N-t-Butoxycarbonylamino)nicotinic acid. n-Butyl lithium (2.18M, 24 mL, 52.51 mmol) is added slowly to a solution of 4-(N-t-butoxycarbonylamino)pyridine (4.08 g, 21 mmol) in THF (50 mL, stirred under N$_2$ at –78° C. The solution is allowed to warm to 0° C., stirred for 3 h, then cooled again to –78° C. and poured into ether (100 mL) containing dry ice. The solution is warmed to room temperature with constant stirring. Water is added and the mixture is neutralized with acetic acid. The resulting solid is collected by vacuum filtration and dried in a vacuum oven to give 4-(N-t-butoxycarbonylamino)nicotinic acid (2.72 g, 54%) as a brown solid. $^1$H NMR (DMSO) δ 11.75 (1H, brs), 8.95 (1H, s), 8.50 (1H, d, J=6.0 Hz), 8.20 (1H, d, J=6.0 Hz), 1.49 (9H, s).

4-Amino nicotinic acid. A mixture of 4-(N-t-butoxycarbonylamino) nicotinic acid (2.72 g, 11.4 mmol), TFA (10 mL), and CH$_2$Cl$_2$ (20 mL) is stirred at room temperature for 12 h. The volatiles are removed under reduced pressure, and the resulting crude 4-amino nicotinic acid is used directly in the next reaction.

3H-Pyrido[4,3-d]pyrimidin-4-one. Crude 4-amino nicotinic acid (2.72 g, 11.4 mmol) in formamide (20 mL) is heated to 170° C. for 12 h. The volatiles are distilled out under reduced pressure (0.8 mm Hg). The residual solid is then purified on a medium pressure silica gel column, eluting with 10% MeOH in CHCl$_3$ to give 3H-pyrido[4,3-d]pyrimidin-4-one (780 mg, 47%) as a whitish yellow solid. $^1$H NMR (DMSO) δ 12.64 (1H, brs), 9.28 (1H, s), 8.83 (1H, d, J=5.5 Hz), 8.30 (1H, s), 7.58 (1H, d, J=5.8 Hz).

3H-Pyrido [4,3 -d]pyrimidin-4-thione. Phosphorous pentasulfide (2.59 g, 5.83 mmol) is added to a solution of 3H-pyrido[4,3-d]pyrimidin-4-one (780 mg, 5.3 mmol) in pyridine (5 mL). The mixture is refluxed for 5 h. On cooling a precipitate forms and the supernatent is decanted off. The solid is suspended in water (20 mL) and then filtered to yield 3H-pyrido[4,3-d]pyrimidin-4-thione (676 mg, 78%) as a black solid. $^1$H NMR (DMSO) δ 14.53 (1H, brs), 9.65 (1H, s), 8.84 (1H, d, J=7.0 Hz), 8.32 (1H, s), 7.64 (1H, d, J=8.0 Hz).

4-Methylthiopyrido[4,3-d]pyrimidine. A mixture of 3H-pyrido[4,3-d]pyrimidin-4-thione (676 mg, 4.14 mmol), triethylamine (1.4 mL, 10.31 mmol), DMSO (4 mL), and iodomethane (0.48 mL, 7.72 mmol) is stirred for 12 h under N$_2$ at 25° C. The mixture is poured onto water and extracted with EtOAc. The organic extracts are dried (MgSO$_4$), and the solvent is removed under reduced pressure to yield 4-methylthiopyrido[4,3-d]pyrimidine (1.15 g, quant.) as a brown solid. $^1$H NMR (DMSO) δ 9.52 (1H, s), 9.16 (1H, s), 8.95 (1H, d, J=6 Hz), 7.86 (1H, d, J=8 Hz), 2.75 (1H, s).

4-Anilinopyrido[4,3-d]pyrimidine. A mixture of 4-methylthiopyrido[4,3-d]pyrimidine (174 mg, 0.97 mmol), and aniline (186.2 mg, 1.99 mmol) in EtOH (2 mL) is refluxed under N$_2$ for 12 h. Cooling to 0° C. forms a solid which is filtered to yield 4-anilinopyrido[4,3-d]pyrimidine (34.5 mg, 16%). $^1$H NMR (DMSO) δ 10.29 (1H, brs), 9.86 (1H, s), 8.82 (1H, d, J=5.8 Hz), 8.72 (1H, s), 7.85 (2H, d, J=7.5 Hz), 7.66 (1H, d, J=5.5 Hz), 7.45 (2H, t, J=8.0 Hz), 7.23 (1H, t, J=7.3 Hz).

EXAMPLE 11

4-(3-Bromoanilino)pyrido[4,3-d]pyrimidine

A mixture of 4-methylthiopyrido[4,3-d]pyrimidine (171 mg, 0.96 mmol), (see previous experimental) and 3-bromoaniline (1 mL) is heated to 100° C. for 2 h. A solid precipitates on cooling and is collected by vacuum filtration and then recrystallized from EtOH to yield 4-(3-bromoanilino)pyrido[4,3-d]pyrimidine (30 mg, 10%). $^1$H NMR (DMSO) δ 10.33 (1H, s), 9.86 (1H, s), 8.84 (1H, d, J=5.8 Hz), 8.79 (1H, s), 8.22 (1H, s), 7.89 (1H, d, J=7.2 Hz), 7.69 (1H, d, J=5.8 Hz), 7.40 (2H, dt, J$_d$=8.0 Hz, J$_f$=1.5 Hz).

EXAMPLE 12

4-(3-Bromoanilino)-7-fluoropyrido[4,3-d]pyrimidine

3-Cyano-4,6-diaminopyridine. Crude 2-bromo-3-cyano-4,6-diaminopyridine [W. J. Middleton, U.S. Pat. No. 2,790, 806 (Apr. 30, 1957), Du Pont; Chem. Abst. 51: P14829 (1957), see also next experimental] (15.1 g, 0.071 mole) is hydrogenated in THF/MeOH (200 mL, 2:1) containing KOAc (7.0 g, 0.071 mole) and 5% Pd/C (4 g) at 55 p.s.i. and 20° C. for 7 days. Filtration over celite, washing with THF/MeOH and removal of the solvent gives a solid, which is dissolved in dilute HCl and water. Adjustment of the solution pH to 10 (conc. NaOH) and cooling gives 3-cyano-4,6-diaminopyridine (6.58 g, 69%) as a yellow solid, mp 197°–198° C. [Metzger, R.; Oberdorfer, J.; Schwager, C.; Thielecke, W.; Boldt, P. Liebigs Ann. Chem. 1980, 946–953 record mp (benzene) 205° C.]. Extraction of the remaining liquor with EtOAc (4×200 mL) gives further product (2.12 g, 22%). $^1$H NMR (DMSO) δ 7.91 (1H, s), 6.26, 6.24 (2H, 2H, brs), 5.63 (1H, s).

4,6-Diamino-3-pyridylcarboxamide. 3-Cyano-4,6-diaminopyridine (4.30 g, 0.032 mole) is added to 90% $H_2SO_4$ (25 mL), then stirred at 60°–70° C. for 3 h. The resulting solution is added to cold conc. NaOH (40%) to give a mixture of 4,6-diamino-3-pyridylcarboxamide and inorganic salts. An analytically pure sample is obtained by chromatography on alumina (10–50% MeOH/CHCl$_3$) to give a pale yellow solid. $^1$HNMR (DMSO) δ 8.15 (1H, s), 6.91 (2H, brs), 7.7–6.3 (2H, brm), 5.78 (2H, brs), 5.56 (1H, s).

7-Amino-4-oxo-3H-pyrido[4,3-d]pyrimidine. Crude 4,6-diamino-3-pyridylcarboxamide (9.2 g) is heated in purified (EtO)$_3$CH (distilled from Na, 60 mL) at 170° C. for 1.5 d. After removing the solvent, the residue is dissolved in hot 2M NaOH, filtered, neutralized (conc. HCl) and cooled to give 7-amino-4-oxo-3H-pyrido[4,3-d]pyrimidine (3.57 g, 69% from the nitrile) as a light brown solid $^1$H NMR (DMSO) δ 11.79 (1H, brs), 8.74 (1H, s), 7.97 (1H, s), 6.76 (2H, brs), 6.38 (1H, s).

7-Fluoro-4-oxo-3H-pyrido[4,3-d]pyrimidine. A solution of 7-amino-4-oxo-3H-pyrido[4,3-d]pyrimidine (1.00 g, 6.17 mmol) in 60% HBF$_4$ (25 mL) at 0° C. is treated with solid NaNO$_2$ (0.85 g, 12.3 mmol, added in portions over 2 h), and is then stirred at 0° C. for a further 1 h and at 20° C. for 30 min. The resulting mixture is ice-cooled, neutralized with saturated aqueous Na$_2$CO$_3$, and extracted with EtOAc (4×100 mL). The extract is washed with water, then filtered through silica gel (EtOAc) to give 7-fluoro-4-oxo-3H-pyrido[4,3-d]pyrimidine (0.48 g, 47%) as a cream solid. $^1$H NMR (DMSO) δ 12.69 (1H, brs), 9.01 (1H, s), 8.31 (1H, s), 7.34 (1H, s).

4-(3-Bromoanilino)-7-fluoropyrido[4,3-d]pyrimidine. A suspension of 7-fluoro-4-oxo-3H-pyrido[4,3-d]pyrimidine (0.23 g, 1.39 mmol) in POCl$_3$ (10 mL) is stirred under reflux for 3.5 h, and is then concentrated under vacuum. The resulting oil is ice-cooled, diluted with CH$_2$Cl$_2$ (100 mL), saturated aqueous Na$_2$CO$_3$ (40 mL) and ice, and stirred at 20° C. for 2 h. The CH$_2$Cl$_2$ extract is separated and the aqueous portion further extracted with CH$_2$Cl$_2$ (2×100 mL), and then the combined extracts are dried (Na$_2$SO$_4$) and filtered to give crude 4-chloro-7-fluoropyrido[4,3-d] pyrimidine. 3-Bromoaniline (1.26 g, 7.35 mmole), 3-bromoaniline hydrochloride (20 mg) and dry isopropanol (5 mL) are added, then the resulting solution is concentrated under vacuum to remove the CH$_2$Cl$_2$ and stirred at 20° C. for 1 h. Upon addition of dilute NaHCO$_3$ and water, the product crystallises. Filtration, washing with water and CH$_2$Cl$_2$, gives pure 4-(3-bromoanilino)-7-fluoropyrido[4,3-d] pyrimidine (297 mg, 67%) as a cream solid. $^1$H NMR (DMSO) δ 10.38 (1H, brs), 9.59 (1H, s), 8.72 (1H, s), 8.17 (1H, s), 7.85 (1H, m), 7.38 (3H, m).

EXAMPLE 13

7-Amino-4-anilinopyrido[4,3-d]pyrimidine 4,6-Diamino-2-bromo-3-cyanopyridine. HBr is bubbled for 2 h into a mixture of malononitrile (16.3 g, 0.247 mol) and toluene (400 mL) at 0° C. A light yellow precipitate forms. The reaction mixture is then heated at 100° C. for 2 h, with much gas evolution. After cooling to room temperature, the yellow solid is isolated via suction filtration, washed with toluene and air dried. The solid (25.96 g) is mixed with water (500 mL), and the pH of the suspension is adjusted to 9–10 with NH$_4$OH (conc.~15 mL). After stirring at room temperature for 1 h, the mixture is filtered. Recrystallization from EtOH affords a yellow solid. After drying at 60° C. in a vacuum oven, 4,6-diamino-2-bromo-3-cyanopyridine (12.95 g, 49%) is obtained. $^1$H NMR (DMSO) δ 6.67 (2H,brs), 6.55 (2H,brs), 5.59 (1H, s).

2,4-Diamino-5-cyanopyridinium acetate. 4,6-Diamino-2-bromo-3-cyanopyridine (12.77 g, 60 mmol) is hydrogenated in THF/MeOH (240 mL, 2:1) containing KOAc (5.9 g, 60 mmol) and 20% Pd/C (0.5 g) at 18 psi at 25° C. for 4 h. The mixture is celite filtered and the solvent is stripped under reduced pressure to give a solid (11.15 g) which is stirred with THF (100 mL) at room temperature for 20 min. The mixture is refiltered and the filtrate is stripped to dryness to give the desired product. After drying in a vacuum oven, 2,4-diamino-5-cyanopyridinium acetate (10.65 g, 92%) is collected as a yellow solid. $^1$H NMR (DMSO) δ 7.90 (1H, s), 6.26 (4H, brs), 5.62 (1H, s), 1.90 (3H, s).

7-Amino-4-thiono-3H-pyrido[4,3-d]pyrimidine. A mixture of 2,4-diamino-5-cyanopyridinium acetate (0.199 g, 1.0 mmol), triethyl orthoformate (1.95 mL) and Ac$_2$O (1.95 mL) is refluxed under N$_2$ with stirring for 3 h. The solvent is then stripped and the residue is dissolved in MeOH (10 mL) containing NaOMe (0.81 g, 15 mmol). H$_2$S is bubbled through the mixture for ~5 min, which is then refluxed overnight. After the solvent is stripped, the residue is dissolved in hot water and boiled with charcoal. After filtration, the filtrate is neutralized with acetic acid whilst hot to generate a yellow solid. On cooling, the solid is collected by suction filtration, and is dried in a vacuum oven overnight. 7-Amino-4-thiono-3H-pyrido[4,3-d]pyrimidine (84 mg, 51%) is isolated as light yellow solid. $^1$H NMR (DMSO) δ 9.82 (1H, s), 9.34 (1H, s), 8.37 (1H, s), 7.80 (2H, d, J=7.5 Hz), 7.38 (2H, t, J=7.5 Hz), 7.12 (1H, t, J=7.5 Hz), 6.61 (2H, brs) 6.43 (1H, s).

7-Amino-4-methylthiopyrido[4,3-d]pyrimidine. NEt$_3$ (6 mL, 43 mmol) is added to a solution of 7-amino-4-thiono-3H-pyrido[4,3-d]pyrimidine (0.77 g, 4.3 mmol) in DMSO (7 mL) stirred under N$_2$ at 25° C. After the two phases have been stirred for 20 min, MeI (0.26 mL, 4.2 mmol) is added. After 2 h, the reaction mixture is poured onto stirring ice-water. Solid forms instantly. After further cooling at 0° C., the solid is collected by suction filtration and dried in a vacuum oven to give 7-amino-4-methylthiopyrido[4,3-d] pyrimidine (0.564 g, 68%). $^1$H NMR (DMSO) δ 8.98 (1H, s), 8.71 (1H, s), 6.94 (2H, brs), 6.49 (1H, s) 2.63 (3H, s).

7-Amino-4-anilinopyrido[4,3-d]pyrimidine. A mixture of 7-amino-4-methylthiopyrido[4,3-d]pyrimidine (0.136 g, 0.7 mmol) and aniline (0.5 mL, 5.5 mmol) is refluxed under N$_2$ at 180° C. for 2 h. The reaction mixture is cooled to 25° C., when it precipitates. The solid is collected by suction filtration and recrystallized from isopropanol, and dried in a vacuum oven overnight. 7-Amino-4-anilinopyrido[4,3-d] pyrimidine (84 mg, 51%) is isolated as a light yellow solid. $^1$H NMR (DMSO) δ 9.82 (1H, s), 9.34 (1H, s), 8.37 (1H, s), 7.80 (2H, d, J=7.5 Hz), 7.38 (2H, t, J=7.5 Hz), 7.12 (1H, t, J=7.5 Hz), 6.61 (2H, brs) 6.43 (1H, s).

EXAMPLE 14

7-Amino-4-(3-hydroxyanilino)pyrido[4,3-d] pyrimidine

A mixture of 7-amino-4-methylthiopyrido[4,3-d] pyrimidine (299 mg, 1.56 mmole) and 3-aminophenol (1.60 g, 14.7 mmole) is stirred at 160° C. for 15 min. The resulting product is chromatographed over silica gel (9% MeOH/CH$_2$Cl$_2$) to give 7-amino-4-(3-hydroxyanilino)pyrido[4,3-d]pyrimidine (108 mg, 18%) as a pale orange solid. $^1$H NMR (DMSO) δ 9.69 (1H, brs), 9.44 (1H, brs), 9.33 (1H, s), 8.38 (1H, s), 7.37 (1H, t, J=2.1 Hz), 7.21 (1H, brd, J=8.4 Hz), 7.14 (1H, t, J=8.0 Hz), 6.59 (2H, brs), 6.53 (1H, ddd, J=7.9, 2.2, 0.8 Hz), 6.43 (1H, s).

EXAMPLE 15

7-Amino-4-(3 -methoxyanilino)pyrido[4,3-d]pyrimidine

A mixture of 7-amino-4-methylthiopyrido[4,3-d]pyrimidine (226 mg, 1.18 mmol) (described in the previous experimental) and m-anisidine (1.00 mL, 8.90 mmol) is stirred under N$_2$ at 190° C. for 1.5 h. The resulting product is chromatographed over silica gel (5–7% EtOH/EtOAc) to give 7-amino-4-(3-methoxyanilino)pyrido[4,3-d]pyrimidine (136 mg, 43%) as a light brown solid. $^1$H NMR (DMSO) δ 9.78 (1H, brs), 9.34 (1H, s), 8.40 (1H, s), 7.50 (1H, brs), 7.44 (1H, d, J=8.0 Hz), 7.28 (1H, t, J=8.2 Hz), 6.71 (1H, dd, J=8.2, 2.3 Hz), 6.61 (2H, brs), 6.45 (1H, s), 3.77 (3H, s).

EXAMPLE 16

7-Amino-4-(2-methoxyanilino)pyrido[4,3-d]pyrimidine

A mixture of 7-amino-4-methylthiopyrido[4,3-d]pyrimidine (227 mg, 1.18 mmole) and o-anisidine (1.00 mL, 8.87 mmol) is stirred under N$_2$ at 180° C. for 2.5 h. The resulting product is chromatographed over silica gel (5% EtOH/EtOAc) to give 7-amino-4-(2-methoxyanilino)pyrido[4,3-d]pyrimidine (147 mg, 47%) as a yellow solid. $^1$H NMR (DMSO) δ 9.44 (1H, brs), 9.25 (1H, s), 8.22 (1H, s), 7.54 (1H, dd, J=7.7, 1.4 Hz), 7.24 (1H, ddd, J=8.1, 7.4, 1.5 Hz), 7.10 (1H, dd, J=8.2, 1.2 Hz), 6.98 (1H, dt, J$_d$=1.3 Hz, J$_t$=7.5 Hz), 6.52 (2H, brs), 6.41 (1H, s), 3.79 (3H, s).

EXAMPLE 17

7-Amino-4-(3-aminoanilino)pyrido[4,3-d]pyrimidine

A mixture of 7-amino-4-methylthiopyrido[4,3-d]pyrimidine (307 mg, 1.60 mmol) (described in a previous experimental) and 3-nitroaniline (2.00 g, 14.5 mmol) is stirred at 200° C. for 1.5 h, and the crude product is suspended in MeOH/THF (4:1, 250 mL) and hydrogenated over 5% Pd/C (2 g) at 60 psi and 20° C. for 24 h. The solution is filtered over celite, washing thoroughly (hot MeOH), and is then absorbed onto alumina and chromatographed on alumina (4–8% EtOH/CHCl$_3$) to give 7-amino-4-(3-aminoanilino)pyrido[4,3-d]pyrimidine (66 mg, 16%) as a green solid. $^1$H NMR (DMSO) δ 9.57 (1H, brs), 9.30 (1H, s), 8.33 (1H, s), 7.04 (1H, t, J=2.0 Hz), 6.99 (1H, t, J=8.0 Hz), 6.88 (1H, brd, J=8.0 Hz), 6.55 (2H, brs), 6.40 (1H, s), 6.34 (1H, dd, J=7.9, 1.3 Hz), 5.10 (2H, brs).

EXAMPLE 18

7-Amino-4-(4-aminoanilino)pyrido[4,3-d]pyrimidine

7-Amino-4-(4-acetamidoanilino)pyrido[4,3-d]pyrimidine. A mixture of 7-amino-4-methylthiopyrido[4,3-d]pyrimidine (138 mg, 0.72 mmole) and 4-aminoacetanilide (1.50 g, 10.0 mmole) is stirred under N$_2$ at 200° C. for 1 h. The resulting product is chromatographed over alumina (8–10% MeOH/CH$_2$Cl$_2$) to give 7-amino-4-(4-acetamidoanilino)pyrido[4,3d]pyrimidine (110 mg, 52%) as a pale yellow solid. $^1$H NMR (DMSO) δ 9.94, 9.79 (1H, 1H, 2 brs), 9.31 (1H, s), 8.34 (1H, s), 7.69 (2H, d, J=8.9 Hz), 7.57 (2H, d, J=8.9 Hz), 6.57 (2H, brs), 6.43 (1H, s), 2.05 (3H, s).

7-Amino-4-(4 -aminoanilino)pyrido[4,3-d]pyrimidine. A solution of 7-amino-4-(4-acetamidoanilino)pyrido[4,3-d]pyrimidine (0.30 g, 1.02 mmole) in aqueous NaOH (2M, 10 mL) and MeOH (10 mL) is stirred at 100° C. for 7 h. The resulting product is chromatographed over alumina (3–4% EtOH/CHCl$_3$) to give 7-amino-4-(4-aminoanilino)pyrido[4,3-d]pyrimidine (86 mg, 33%) as an orange solid. $^1$H NMR (DMSO) δ 9.58 (1H, brs), 9.24 (1H, s), 8.25 (1H, s), 7.31 (2H d, J=8.6 Hz), 6.58 (2H, d, J=8.6 Hz), 6.48 (2H, brs), 6.39 (1H, s), 5.00 (2H, brs).

EXAMPLE 19

7-Amino-4-(3-dimethylaminoanilino)pyrido[4,3-d]pyrimidine

A mixture of 7-amino-4-methylthiopyrido[4,3-d]pyrimidine (245 mg, 1.28 mmol) (described in a previous experimental) and N,N-dimethyl-1,3-phenylenediamine (1.60 g, 11.8 mmol) is stirred under N$_2$ at 190° C. for 1 h, and the resulting product is chromatographed (twice) over alumina (3% EtOH/CHCl$_3$) to give 7-amino-4-(3-dimethylaminoanilino)pyrido[4,3-d]pyrimidine (113 mg, 32%) as a pale yellow solid. 1H NMR (DMSO) δ 9.66 (1H, brs), 9.33 (1H, s), 8.36 (1H, s), 7.22 (1H, brd, J=7.8 Hz), 7.16 (2H, m), 6.57 (2H, brs), 6.51 (1H, ddd, J=8.0, 2.3, 1.2 Hz), 6.42 (1H, s), 2.91 (6H, s).

EXAMPLE 20

7-Amino-4-(4-dimethylaminoanilino)pyrido[4,3-d]pyrimidine

A mixture of 7-amino-4-methylthiopyrido[4,3-d]pyrimidine (256 mg, 1.33 mmole) and N,N-dimethyl-1,4-phenylenediamine (1.95 g, 14.4 mmole) is stirred under N$_2$ at 190° C. for 20 min. The resulting product is chromatographed over alumina (3–7% EtOH/CHCl$_3$) to give 7-amino-4-(4-dimethylaminoanilino)pyrido[4,3-d]pyrimidine (198 mg, 53%) as an orange solid. $^1$H NMR (DMSO) δ 9.67 (1H, brs), 9.27 (1H, s), 8.27 (1H, s), 7.51 (2H, d, J=8.9 Hz), 6.75 (2H, d, J=8.9 Hz), 6.51 (2H, brs), 6.39 (1H, s), 2.89 (6H, s).

EXAMPLE 21

7-Amino-4-(2-nitroanilino)pyrido[4,3-d]pyrimidine

A mixture of 7-amino-4-methylthiopyrido[4,3d]pyrimidine (220 mg, 1.15 mmole) and 2-nitroaniline (2.00 g, 14.5 mmole) is heated to 100° C., then excess dry HCl gas is added to the hot stirred solution, and the mixture stirred at 160° C. for 20 min. The resulting product is neutralized with excess NaHCO$_3$, dissolved in MeOH/CHCl$_2$, dried onto silica gel and chromatographed over silica gel (2–4% MeOH/CH$_2$Cl$_2$) to give 7-amino-4-(2-nitroanilino)pyrido[4, 3-d]pyrimidine (108 mg, 33%) as a yellow brown solid. $^1$H NMR (DMSO) δ 10.40 (1H, brs), 9.24 (1H, brs), 8.20 (1H, brs), 8.12 (1H, brs), 8.01 (2H, brs), 7.75 (1H, brs), 6.70 (2H, brs), 6.43 (1H, brs).

EXAMPLE 22

7-Amino-4-(3-nitroanilino)pyrido[4,3-d]pyrimidine

A mixture of 7-amino-4-methylthiopyrido[4,3-d]pyrimidine (127 mg, 0.66 mmol) (described in a previous experimental) and 3-nitroaniline (1.70 g, 12.3 mmol) is stirred under $N_2$ at 200° C. for 1.5 h. The resulting product is chromatographed over alumina (5–20% EtOH/CHCl$_3$) to give 7-amino-4-(3-nitroanilino)pyrido[4,3-d]pyrimidine (81 mg, 39%) as a brown solid. $^1$H NMR (DMSO) δ 10.17 (1H, brs), 9.37 (1H, s), 8.87 (1H, brs), 8.48 (1H, s), 8.33 (1H, brd, J=7.5 Hz), 7.95 (1H, ddd, J=8.2, 2.1, 1.0 Hz), 7.67 (1H, t, J=8.2 Hz), 6.70 (2H, brs), 6.47 (1H, s).

EXAMPLE 23

7-Amino-4-(3-fluoroanilino)pyrido[4,3-d]pyrimidine

A mixture of 7-amino-4-methylthiopyrido[4,3-d]pyrimidine (215 mg, 1.12 mmol) and 3-fluoroaniline (1.16 g, 10.4 mmol) is stirred at 160° C. for 30 min. The resulting product is chromatographed over silica gel (6–7% MeOH/CH$_2$Cl$_2$) to give 7-amino-4-(3-fluoroanilino)pyrido[4,3-d]pyrimidine (185 mg, 65%) as a white solid. $^1$H NMR (DMSO) δ 9.94 (1H, brs), 9.36 (1H, s), 8.46 (1H, s), 7.91 (1H, brd, J=11.9 Hz), 7.63 (1H, brd, J=8.1 Hz), 7.41 (1H, dd, J=15.7, 7.7 Hz), 6.93 (1H, dt, J$_f$=8.5 Hz, J=2.4 Hz), 6.68 (2H, brs), 6.38 (1H, s).

EXAMPLE 24

7-Amino-4-(3-chloroanilino)pyrido[4,3-d]pyrimidine

A mixture of 7-amino-4-methylthiopyrido[4,3-d]pyrimidine (208 mg, 1.08 mmol) and 3-chloroaniline (1.21 g, 9.48 mmol) is stirred at 150° C. for 20 min. The resulting product is chromatographed over alumina (5–10% MeOH/CH$_2$Cl$_2$) to give 7-amino-4-(3-chloroanilino)pyrido[4,3-d]pyrimidine (177 mg, 60%) as a white solid. $^1$H NMR (DMSO) δ 9.92 (1H,brs), 9.35 (1H, s), 8.45 (1H, s), 8.08 (1H, brs), 7.79 (1H, brd, J=8.0 Hz), 7.40 (1H, t, J=8.1 Hz), 7.16 (1H, dd, J=7.9, 1.3 Hz), 6.68 (2H, brs), 6.46 (1H, s).

EXAMPLE 25

7-Amino-4-(3,4-dichloroanilino)pyrido[4,3-d]pyrimidine

A mixture of 7-amino-4-methylthiopyrido[4,3-d]pyrimidine (247 mg, 1.29 mmol) and 3,4-dichloroaniline (1.50 g, 9.26 mmol) is stirred at 165° C. for 30 min. The resulting product is chromatographed over silica gel (7–8% MeOH/CH$_2$Cl$_2$) to give 7-amino-4-(3,4-dichloroanilino)pyrido[4,3-d]pyrimidine (252 mg, 64%) as a pale yellow solid. $^1$H NMR (DMSO) δ 9.97 (1H, brs), 9.34 (1H, s), 8.47 (1H, s), 8.29 (1H, brs), 7.86 (1H, brd, J=8.6 Hz), 7.62 (1H, d, J=8.8 Hz), 6.70 (2H, brs), 6.46 (1H, s).

EXAMPLE 26

7-Amino-4-(2-bromoanilino)pyrido[4,3-d]pyrimidine

A mixture of 7-amino-4-methylthiopyrido[4,3-d]pyrimidine (198 mg, 1.03 mmol) (described in a previous experimental) and 2-bromoaniline (1.00 mL, 9.18 mmol) is stirred under $N_2$ at 180° C. for 2.5 h, and the resulting product is chromatographed on alumina (1% EtOR/CHCl$_3$) to give 7-amino-4-(2-bromoanilino)pyrido[4,3-d]pyrimidine (108 mg, 33%) as a pale yellow solid, $^1$H NMR (DMSO) δ 9.91 (1H, brs), 9.27 (1H, s), 8.20 (1H, s), 7.73 (1H, d, J=7.9 Hz), 7.50 (1H, m), 7.44 (1H, t, J=6.9 Hz), 7.25 (1H, m), 6.59 (2H, brs), 6.42 (1H, s).

EXAMPLE 27

7-Amino-4-(3-bromoanilino)pyrido[4,3-d]pyrimidine

A mixture of 7-amino-4-methylthiopyrido[4,3-d]pyrimidine (167 mg, 0.87 mmol) (described in a previous experimental) and 3-bromoaniline (0.75 mL, 7.8 mmol) is stirred under $N_2$ at 190° C. for 2.5 h, and the precipitate which appears on cooling is recrystallized from Pr$^i$OH. $^1$H NMR (DMSO) δ 9.91 (1H, brs), 9.34 (1H, s), 8.45 (1H, s), 8.19 (1H, s), 7.84 (1H, d, J=8.0 Hz), 7.34 (1H, t, J=8.0 Hz), 7.29 (1H, d, J=8.2 Hz), 6.68 (2H, brs), 6.45 (1H, s).

EXAMPLE 28

7-Amino-4-(4-bromoanilino)pyrido[4,3-d]pyrimidine

A mixture of 7-amino-4-methylthiopyrido[4,3-d]pyrimidine (261 mg, 1.36 mmole) and 4-bromoaniline (1.00 g, 5.81 mmole) is stirred under $N_2$ at 200° C. for 15 min. The resulting product is chromatographed on silica gel (10–15% EtOH/EtOAc) to give 7-amino-4-bromoanilino)pyrido[4,3-d]pyrimidine (200 mg, 46%) as a pale yellow solid. $^1$H NMR. (DMSO) δ 9.88 (1H, brs), 9.34 (1H, s), 8.40 (1H, s), 7.83 (2H, d, J=8.8 Hz), 7.55 (2H, d, J=8.8 Hz), 6.64 (2H, brs), 6.44 (1H, s).

EXAMPLE 29

7-Amino-4-(3-iodoanilino)pyrido[4,3-d]pyrimidine

A mixture of 7-amino-4-methylthiopyrido[4,3-d]pyrimidine (72 mg, 0.37 mmol) and 3-iodoaniline (1.25 g, 5.71 mmol) is stirred at 160° C. for 30 min. The resulting product is chromatographed over silica gel (5–7% MeOH/CH$_2$Cl$_2$) to give 7-amino-4-(3-iodoanilino)pyrido[4,3-d]pyrimidine (83 mg, 61%) as a light brown rosettes. $^1$H NMR (DMSO) δ 9.84 (1H, brs), 9.34 (1H, s), 8.44 (1H, s), 8.30 (1H, brs), 7.90 (1H, dd, J=7.9, 0.8 Hz), 7.47 (1H, d, J=7.7 Hz), 7.18 (1H, t, J=8.0 Hz), 6.66 (2H, brs), 6.46 (1H, s).

EXAMPLE 30

7-Amino-4-(2-trifluoromethylanilino)pyrido[4,3-d]pyrimidine

A mixture of 7-amino-4-methylthiopyrido[4,3-d]pyrimidine (300 mg, 1.56 mmol), 2-aminobenzotrifluoride hydrochloride (1.00 g, 5.06 mmol) and 2-aminobenzotrifluoride (2.00 g, 12.4 mmol) is stirred at 160° C. for 10 min. The resulting product is neutralized with excess NaHCl, dissolved in MeOH/CHCl$_3$, dried onto silica gel and chromatographed over silica gel (6–7% MeOH/CH$_2$Cl$_2$) to give 7-amino-4-(2-trifluoromethylanilino)pyrido[4,3-d]pyrimidine (194 mg, 41%) as a cream solid, mp (MeOH/CHCl$_3$/light petroleum) 126°–130° C. (dec.). $^1$H NMR (DMSO) δ 10.60 (1H, brs), 9.17 (1H, brs), 8.13 (1H, brs), 7.76, 7.69 (1H, 1H, m, m), 7.45 (2H, m), 6.66 (2H, brs), 6.36 (1H, s).

EXAMPLE 31

7-Amino-4-(3-trifluoromethylanilino)pyrido[4,3-d]pyrimidine

A mixture of 7-amino-4-methylthiopyrido[4,3-d]pyrimidine (234 mg, 1.22 mmol) (described in a previous experimental) and 3-aminobenzotrifluoride (2.00 mL, 16.0 mmol) is stirred under $N_2$ at 190°–200° C. for 2 h, and the resulting product is then chromatographed over silica gel (5–10% EtOH/EtOAc), and then over alumina (5–7% EtOH/CHCl$_3$) to give 7-amino-4-(3-trifluoromethylanilino)pyrido[4,3-d]pyrimidine (157 mg, 42%) as a cream solid. $^1$H NMR (DMSO) δ 10.04 (1H, s), 9.37 (1H, s), 8.46 (1H, s), 8.31 (1H, s), 8.19 (1H, d, J=8.2 Hz), 7.62 (1H, t, J=8.0 Hz), 7.45 (1H, d, J=7.7 Hz), 6.69 (2H, brs), 6.47 (1H, s).

EXAMPLE 32

7-Amino-4-(4-trifluoromethylanilino)pyrido[4,3-d]pyrimidine

A mixture of 7-amino-4-methylthiopyrido[4,3-d]pyrimidine (390 mg, 2.03 mmol), 4-aminobenzotrifluoride hydrochloride (0.40 g, 2.02 mmol) and 4-aminobenzotrifluoride (1.61 g, 10.0 mmol) is stirred at 180° C. for 2 min. The resulting product is neutralized with excess $NaHCO_2$, dissolved in $MeOH/CHCl_3$, dried onto alumina and chromatographed over alumina (4–7% MeOH/ $CH_2Cl_2$) to give 7-amino-4-(4-trifluoromethylanilino) pyrido[4,3-d]pyrimidine (390 mg, 63%) as a cream solid. Analytically pure material was obtained by further chromatography over silica gel (5% $MeOH/CH_2Cl_2$) to give pale yellow needles. $^1H$ NMR (DMSO) $\delta$ 10.09 (1H, brs), 9.40 (1H, s), 8.48 (1H, s), 8.13 (2H, d, J=8.2 Hz), 7.74 (2H, d, J=8.7 Hz), 6.72 (2H, brs), 6.40 (1H, s).

EXAMPLE 33

4-(3-Bromoanilino)-7-methylaminopyrido[4,3-d]pyrimidine

A mixture of 7-fluoro-4-(3-bromoanilino)pyrido[4,3-d]pyrimidine (74 mg, 0.23 mmol), triethylamine (7 mL, 50 mmol) and methylamine hydrochloride (3.0 g, 44 mmol) in isopropanol (30 mL) contained in a steel bomb is stirred at 95° C. (oil bath) for 5 h. The resulting mixture is concentrated under vacuum, basified with aqueous $Na_2CO_3$, diluted with water and extracted with EtOAc (3×100 mL). Chromatography of this extract on silica gel (3% $MeOH/CH_2Cl_2$) gives 4-(3-bromoanilino)-7-methylaminopyrido[4,3-d] pyrimidine (50 mg, 65%) as a pale yellow solid. $^1H$ NMR (DMSO) $\delta$ 9.93 (1H, brs), 9.37 (1H, s), 8.47 (1H, s), 8.18 (1H, s), 7.84 (1H, d, J=7.8 Hz), 7.34 (1H, t, J=7.9 Hz), 7.30 (1H, brd, J=8.1 Hz), 7.19 (1H, q, J=4.7 Hz), 6.35 (1H, s), 2.85 (3H, d, J=4.8 Hz).

EXAMPLE 34

4-(3-Bromoanilino)-7-dimethylaminopyrido[4,3-d]pyrimidine

A mixture of 7-fluoro-4-(3-bromoanilino)pyrido[4,3-d]pyrimidine (101 mg, 0.32 mmol), triethylamine (4.4 mL, 32 mmole) and dimethylamine hydrochloride (2.58 g, 32 mmol) in isopropanol (30 mL) contained in a steel bomb is stirred at 100° C. (oil bath) for 4 h. The resulting solution is concentrated under vacuum, basified with aqueous $Na_2CO_3$ and diluted with water to give a solid. Filtration and recrystallisation from $MeOH/CHCl_3$ gives 7-dimethylamino-4-(3-bromoanilino)pyrido[4,3-d]pyrimidine (102 mg, 94%) as a pale yellow solid. $^1H$ NMR (DMSO) $\delta$ 9.93 (1H, brs), 9.42 (1H, s), 8.48 (1H, s), 8.19 (1H, s), 7.85 (1H, d, J=7.7 Hz), 7.35 (1H, t, J=7.9 Hz), 7.30 (1H, brd, J=7.8 Hz), 6.53 (1H, s), 3.16 (6H, s).

EXAMPLE 35

4-[N-(3-Bromophenyl)-N-methylamino]-7-methylaminopyrido[4,3-d]pyrimidine

A mixture of 7-fluoro-4-(3-bromoanilino)pyrido[4,3-d] pyrimidine (100 mg, 0.31 mmole), triethylamine (4.4 mL, 32 mmole) and methylamine hydrochloride (2.12 g, 32 mmole) in isopropanol (30 mL) contained in a steel bomb is stirred at 100° C. (oil bath) for 5 h. The resulting mixture is concentrated under vacuum, basified with aqueous $Na_2CO_3$, diluted with water and extracted with EtOAc (3×100 mL). Chromatography of this extract on silica gel (1–2% MeOH/ $CH_2Cl_2$) gives 4-[N-(3-bromophenyl)-N-methylamino]-7-methylaminopyrido[4,3-d]pyrimidine (23 mg, 21%) as a pale yellow solid. $^1H$ NMR (DMSO) $\delta$ 8.14 (1H, s), 7.79 (1H, s), 7.30 (1H, t, J=8.0 Hz), 7.20 (1H, ddd, J=7.9, 1.8, 0.8 Hz), 7.03 (1H, brq, J=4.9 Hz), 7.01 (1H, t, J=1.9 Hz), 6.82 (1H, ddd, J=7.8, 1.8, 0.9 Hz), 6.25 (1H, s), 3.40 (3H, s), 2.73 (3H, d, J=4.9 Hz).

EXAMPLE 36

7-Acetylamino-4-(3-bromoanilino)pyrido[4,3-d]pyrimidine

A mixture of 7-amino-4-(3-bromoanilino)pyrido[4,3-d] pyrimidine (0.154 g, 0.49 mmol), acetic anhydride (0.14 mL, 1.5 mmol), triethylamine (0.14 mL, 1.0 mmol) and a catalytic amount of 4-(N,N-dimethylamino)pyridine are stirred under $N_2$ at room temperature for 18 h. The reaction is then quenched by addition of ice water. The dark precipitate is collected by Buchner filtration and is purified by preparative tlc (Rf=0.25, 7% $MeOH/CHCl_3$). Recrystallization from EtOH gives 7-acetylamino-4-(3-bromoanilino) pyrido[4,3-d]-pyrimidine (13.5 mg, 7.7%). $^1H$ NMR (DMSO) $\delta$ 10.92 (1H, s), 10.22 (1H, s), 9.64 (1H, s), 8.70 (1H, s), 8.28 (1H, s), 8.21 (1H, s), 7.88 (1H, d, J=7.7 Hz) 7.41–7.34 (3H, m), 2.16 (3H, s).

EXAMPLE 37

4-(3-Bromoanilino)-7-methoxypyrido[4,3-d]pyrimidine

A solution of 7-fluoro-4-(3-bromoanilino)pyrido[4,3-d] pyrimidine (100 mg, 0.31 mmol) in 1M sodium methoxide-methanol (30 mL) is stirred under reflux for 42 h. The resulting mixture is concentrated under reduced pressure, diluted with water and neutralized with dilute HCl to give 7-methoxy-4-(3-bromoanilino)pyrido[4,3-d]pyrimidine (92 mg, 89%) as a white solid. $^1H$ NMR (DMSO) $\delta$ 10.22 (1H, brs), 9.57 (1H, s), 8.63 (1H, s), 8.19 (1H, s), 7.86 (1H, brd, J=7.9 Hz), 7.39 (1H, t, J=7.9 Hz), 7.35 (1H, dd, J=7.9, 1.5 Hz), 6.96 (1H, s), 4.00 (3H, s).

EXAMPLE 38

4-Benzylaminopyrido[4,3-d]pyrimidine

4-Methylthiopyrido[4,3-d]pyrimidine (160.4 mg, 0.902 mmol), and benzylamine (106.3 mg, 0.992 mmol) in EtOH (2 mL) are heated at 80° C. for 12 h, and then the solvent is removed under reduced pressure. The resulting solid is suspended in $CH_2Cl_2$, filtered, and the resulting solid is purified by preparative tlc on silica, eluting with 5% MeOH in $CHCl_3$. Removal of the solvent under reduced pressure yields 4-benzylaminopyrido[4,3-d]pyrimidine (36 mg, 17%). $^1H$ NMR (DMSO) $\delta$ 9.60 (1H, s), 9.37 (1H, t, J=5.8 Hz), 8.72 (1H, d, J=5.8 Hz), 8.57 (1H, s), 7.54 (1H, d, J=5.8 Hz), 7.37 (2H, d, J=7.0 Hz), 7.33 (2H, t, J=7.3 Hz), 7.25 (1H, t, J=7.2 Hz), 4.81 (2H, d, J=5.8 Hz).

EXAMPLE 39

4-([R]-1-Phenylethylamino)pyrido[4,3-d]pyrimidine

To a mixture of 4-methylthiopyrido[4,3-d]pyrimidine (85 mg, 0.48 mmol) and EtOH (2.5 mL) is added R-methylbenzylamine (0.13 mL, 1.0 mmol) dropwise. The resulting mixture is refluxed at 80° C. for 20 h. The solvent is removed under reduced pressure to give an oil which is crystallized from MeOH to give 4-([R]-1-phenylethylamino)pyrido[4,3-d]pyrimidine (41.6 mg, 35%), mp 138°–138.5° C. $^1$H NMR (DMSO) δ 9.77 (1H, d, J=0.7 Hz), 9.00 (1H, d, J=7.7 Hz), 8.73 (1H, d, J=5.8 Hz), 8.54 (1H, s), 7.53 (1H, dd, J=5.8, 0.5 Hz), 7.45 (2H, d, J=7.2 Hz), 7.33 (2H, t, J=7.6 Hz), 7.23 (1H, H, J=7.5, 1.2 Hz), 5.63 (1H, p, J=7.2 Hz), 1.61 (3H, t, J=7.0 Hz).

EXAMPLE 40

7-Amino-4-benzylaminopyrido[4,3-d]pyrimidine

A mixture of 2,4-diamino, 5-cyanopyridinium acetate (8.78 g, 45 mmol), formic acid (10.66 g, 0.204 mol) and benzylamine (45 mL, 0.41 mol) is heated at 200° C. under $N_2$ for 2 h. Upon cooling, it solidifies. Water (500 mL) is added and the gummy solid/water mixture is stirred for ~20 min. at 0° C. The liquid is decanted. The solid is washed with water and then recrystallized from isopropanol (25 mL). After drying in a vacuum oven overnight, 7-amino-2-benzylaminopyrido[4,3-d]pyrimidine (8.29 g, 73%) is obtained as a light yellow solid. $^1$H NMR (DMSO) δ 9.10 (1H, s), 8.85 (1H, t, J=5.8 Hz), 8.25 (1H, s), 7.21–7.36 (5H, m), 6.46 (2H, brs), 6.35 (1H, s), 4.74 (2H, d, J=6.0 Hz).

EXAMPLE 41

7-Amino-4-([R]-1-phenylethylamino)pyrido[4,3-d] pyrimidine

A mixture of [R]-1-phenylethylamine (0.072 mL, 0.55 mmol) and 7-amino-4-methylthiopyrido[4,3-d]pyrimidine (97 mg, 0.5 mmol) (described in a previous experimental) is heated at 180° C. under $N_2$ for 1.5 hr. The reaction is then cooled to room temperature producing a precipitate. The mixture is added to water and $CHCl_3$, sonicated and filtered. The phases are separated and the aqueous phase is extracted with $CHCl_3$. The combined extracts are washed with water, saturated brine and dried ($MgSO_4$). The solvent is removed under reduced pressure and the residue purified by using preparative tlc (5% MeOH/$CHCl_3$) and recrystallization from $CHCl_3$ to give 7-amino-4-([R]-1-phenylethylamino) pyrido[4,3-d]pyrimidine (14.5 mg, 11%), mp 231.8°–232.1° C. $^1$H NMR (DMSO) δ 9.23 (1H, s), 8.50 (1H, d, J=8.0 Hz), 8.19 (1H, s), 7.41 (2H, d, J=7.0 Hz), 7.31 (2H, t, J=8.0 Hz, 7.21 (1H, H, J=7.4, 1.2 Hz), 6.45 (2H, s), 6.33 (1H, s), 5.56 (1H, p, J=7.2 Hz), 1.55 (3H, d, J=7.0 Hz).

EXAMPLE 42

7-Amino-4-(2-aminobenzylamino)pyrido[4,3-d] pyrimidine

A mixture of 7-amino-4-methylthiopyrido[4,3-d] pyrimidine (136 mg, 0.71 mmol) (described in a previous experimental) and 2-aminobenzylamine (1.70 g, 13.8 mmol) in isopropanol (5 mL) is stirred at reflux for 1 h, and the resulting product is chromatographed on silica gel (7–20% EtOH/EtOAc) and alumina (6–10% EtOH/$CHCl_3$) to give 7-amino-4-(2-aminobenzylamino)pyrido[4,3-d]pyrimidine (89 mg, 47%) as a white solid. $^1$H NMR (DMSO) δ 9.08 (1H, s), 8.68 (1H, t, J=5.8 Hz), 8.26 (1H, s), 7.05 (1H, d, J=7.4 Hz), 6.96 (1H, t, J=7.6 Hz), 6.63 (1H, d, J=7.9 Hz), 6.51 (1H, t, J=7.4 Hz), 6.46 (2H, brs), 6.35 (1H, s), 5.20 (2 H, brs), 4.56 (2H, d, J=5.8 Hz).

EXAMPLE 43

7-Amino-4-(3-dimethylaminobenzylamino)pyrido[4,3-d]-pyrimidine

A mixture of 7-amino-4-methylthiopyrido[4,3-d] pyrimidine (236 mg, 1.23 mmol) (described in a previous experimental) and 3-dimethylamino-benzylamine (1.36 g, 9.07 mmol) in isopropanol (5 mL) is stirred under $N_2$ at reflux for 1 h, and the resulting product is chromatographed on silica gel (10–15% EtOH/EtOAc), then on alumina (1% EtOH/$CHCl_3$) to give 7-amino-4-(3-dimethylaminobenzylamino)pyrido[4,3-d]pyrimidine (145 mg, 40%) as a white solid. $^1$H NMR (DMSO) δ 9.11 (1H, s), 8.79 (1H, t, J=5.9 Hz), 8.26 (1H, s), 7.11 (1H, dd, J=8.0, 7.7 Hz), 6.73 (1H, brs), 6.63 (1H, d, J=7.6 Hz), 6.60 (1H, dd, J=8.1, 2.2 Hz), 6.44 (2H, brs), 6.35 (1H, s), 4.67 (2H, d, J=5.8 Hz), 2.86 (6H, s).

EXAMPLE 44

7-Amino-4-(3-nitrobenzylamino)pyrido[4,3-d] pyrimidine

A mixture of 7-amino-4-methylthiopyrido[4,3-d] pyrimidine (228 mg, 1.19 mmol) (described in a previous experimental) and 3-nitrobenzylamine (0.81 g, 5.33 mmol) is stirred under $N_2$ at 150°–160° C. for 1.5 h, and the resulting product chromatographed on silica gel (5–10% EtOH/EtOAc) to give 7-amino-4-(3-nitrobenzylmino) pyrido)[4,3-d]pyrimidine (151 mg, 43%) as a yellow solid. $^1$H NMR (DMSO) δ 9.11 (1H, s), 8.98 (1H, t, J=5.5 Hz), 8.26 (1H, s), 8.22 (1H, brs), 8.12 (1H, dd, J=8.0, 1.8 Hz), 7.83 (1H, d, J=7.7 Hz), 7.63 (1H, t, J=7.9 Hz), 6.50 (2H, brs), 6.38 (1H, s), 4.85 (2H, d, J=5.8 Hz).

EXAMPLE 45

7-Amino-4-(3-methoxybenzylamino)pyrido[4,3-d] pyrimidine

A mixture of 7-amino-4-methylthiopyrido[4,3-d] pyrimidine (136 mg, 0.71 mmol) (described in a previous experimental) and 3-methoxybenzylamine (1.37 g, 10.0 mmol) in isopropanol (3 mL) is stirred under $N_2$ at reflux for 3 h. Evaporation of the solvent and chromatography on silica gel (5–10% EtOH/EtOAc) gives 7-amino-4-(3-methoxybenzylamino)pyrido[4,3-d]pyrimidine (153 mg, 77%) as a white solid. $^1$H NMR (DMSO) δ 9.11 (1H, s), 8.83 (1H, t, J=5.7 Hz), 8.26 (1H, s), 7.24 (1H, dt, $J_d$=0.8 Hz, $J_t$=8.1 Hz), 6.92 (2H, m), 6.81 (1H, dt, $J_d$=8.2 Hz, $J_t$=1.2 Hz), 6.46 (2H, brs), 6.37 (1H, s), 4.71 (2H, d, J=5.8 Hz), 3.73 (3H, s).

EXAMPLE 46

7-Amino-4-(4-chlorobenzylamino)pyrido[4,3-d] pyrimidine mesylate

The free base (56 mg, 0.20 mmol) (prepared from 2,4-diamino, 5-cyanopyridinium acetate, formic acid and 4-chlorobenzylamine at 200° C. as described in a previous example is precipitated from acetone solution with methanesulfonic acid (105 μL, 0.23 mmol) to give a polymesylate salt. $^1$H NMR (DMSO) δ 10.59 (1H, t, J=5.6 Hz), 9.24(1H, s), 8.69 (1H, s), 7.42 (4H, s), 6.42 (1H, s), 5.8 (~6H, vbrs), 4.89 (2H, d, J=5.8 Hz), 2.41 (~7.5H, s).

EXAMPLE 47

7-Amino-4-(2-bromobenzylamino)pyrido[4,3-d] pyrimidine

A mixture of 7-amino-4-methylthiopyrido[4,3-d] pyrimidine (225 mg, 1.17 mmol) (described in a previous experimental) and 2-bromobenzylamine (0.84 g, 4.52 mmol) is stirred under $N_2$ at 140° C. for 1 h, and the resulting product chromatographed on silica gel (1–5% EtOH/EtOAc) to give 7-amino-4-(2-bromobenzylamino)pyrido[4,3-d] pyrimidine (175 mg, 45%) as a light brown solid. $^1$H NMR (DMSO) δ 9.16 (1H, s), 8.85 (1H, t, J=5.7 Hz), 8.24 (1H, s), 7.64 (1H, d, J=7.8 Hz), 7.34 (1H, dd, J=7.7, 7.1 Hz), 7.31 (1H, dd, J=7.7, 2.4 Hz), 7.21 (1H, ddd, J=7.8, 6.9, 2.4 Hz), 6.50 (2H, brs), 6.39 (1H, s), 4.74 (2H, d, J=5.7 Hz).

EXAMPLE 48

7-Amino-4-(3-bromobenzylamino)pyrido[4,3-d] pyrimidine

A mixture of 7-amino-4-methylthiopyrido[4,3-d] pyrimidine (228 mg, 1.19 mmol) (described in a previous experimental) and 3-bromobenzylamine (0.84 g, 4.52 mmol) is stirred under N$_2$ at 140° C. for 1 h. The resulting product is chromatographed on silica gel (2–10% EtOH/EtOAc) to give 7-amino-4-[(3-bromophenyl)methylamino]pyrido[4,3-d]pyrimidine (203 mg, 52%) as a light brown solid. $^1$H NMR (DMSO) δ 9.09 (1H, s), 8.86 (1H, t, J=5.8 Hz), 8.26 (1H, s), 7.54 (1H, s), 7.44 (1H, d, J=7.8 Hz,), 7.36 (1H, d, J=7.6 Hz), 7.29 (1H, t, J=7.7 Hz), 6.48 (2H, s), 6.37 (1H, s), 4.73 (2H, d, J=5.8 Hz).

EXAMPLE 49

7-Amino-4-(4-bromobenzylamino)pyrido[4,3-d] pyrimidine

A mixture of 7-amino-4-methylthiopyrido[4,3-d] pyrimidine (234 mg, 1.22 mmol) (described in a previous experimental) and 4-bromobenzylamine (0.84 g, 4.52 mmol) is stirred under N$_2$ at 140° C. for 1 h, and the resulting product chromatographed on silica gel (10% EtOH/EtOAc) to give 7-amino-4-(4-bromobenzylamino)pyrido[4,3-d] pyrimidine (192 mg, 48%) as a cream solid. $^1$H NMR (DMSO) δ 9.09 (1H, s), 8.87 (1H, t, J=5.7 Hz), 8.25 (1H, s), 7.51 (2H, d, J=8.3 Hz), 7.31 (2H, d, J=8.3 Hz), 6.46 (2H, brs), 6.37 (1H, s), 4.70 (2H, d, J=5.8 Hz).

EXAMPLE 50

7-Amino-4-(2-trifluoromethylbenzylamino)pyrido[4, 3-d]pyrimidine

A mixture of 7-amino-4-methylthiopyrido[4,3-d] pyrimidine (225 mg, 1.17 mmol) and 2-(trifluoromethyl) benzylamine (0.90 mL, 6.42 mmol) is stirred under N$_2$ at 150° C. for 1 h. The resulting product is chromatographed on silica gel (5% EtOH/EtOAc) to give 7-amino-4-(2-trifluoromethylbenzyl) aminopyrido[4,3-d]pyrimidine (0.22 g, 59%) as a white solid. $^1$H NMR (DMSO) δ 9.16 (1H, s), 8.88 (1H, t, J=5.7 Hz), 8.23 (1H, s), 7.75 (1H, d, J=7.7 Hz), 7.62 (1H, t, J=7.5 Hz), 7.50 (1H, d, J=7.4 Hz), 7.47 (1H, t, J=7.6 Hz), 6.51 (2H, brs), 6.39 (1H, s), 4.92 (2H, d, J=5.5 Hz).

EXAMPLE 51

7-Amino-4-(3-trifluoromethylbenzylamino)pyrido[4, 3-d]pyrimidine

A mixture of 7-amino-4-methylthiopyrido[4,3-d] pyrimidine (225 mg, 1.17 mmole) and 3-(trifluoromethyl) benzylamine (0.63 mL, 4.40 mmole) is stirred under N$_2$ at 140° C. for 1 h. The resulting product is chromatographed on silica gel (3–5% EtOH/EtOAc) to give 7-amino-4-[(3-trifluoromethylphenyl)methylamino]pyrido[4,3-d] pyrimidine (0.24 g, 63%) as a light brown solid. $^1$H NMR (DMSO) δ 9.10 (1H, s), 8.92 (1H, t, J=5.7 Hz), 8.26 (1H, s), 7.71 (1H, s), 7.66 (1H, d, J=7.4 Hz), 7.62 (1H, d, J=7.8 Hz), 7.57 (1H, t, J=7.6 Hz), 6.49 (2H, brs), 6.38 (1H, s), 4.82 (2H, d, J=5.8 Hz).

EXAMPLE 52

7-Amino-4-(4-trifluoromethylbenzylamino)pyrido[4, 3-d]pyrimidine

A mixture of 7-amino-4-methylthiopyrido[4,3-d] pyrimidine (225 mg, 1.17 mmol) and 4-(trifluoromethyl) benzylamine (0.63 mL, 4.42 mmol) is stirred under N$_2$ at 140° C. for 1 h. The resulting product is chromatographed on alumina (5–10% EtOH/CHCl$_3$) then silica gel (2–10% EtOH/EtOAc) to give 7-amino-4-[(4-trifluoromethylphenyl) methylamino]pyrido[4,3-d]pyrimidine (0.21 g, 56%) as a light brown solid. $^1$H NMR (DMSO) δ 9.12 (1H, s), 8.94 (1H, t, J=5.8 Hz), 8.24 (1H, s), 7.69 (2H, d, J=8.1 Hz), 7.56 (2H, d, J=8.1 Hz), 6.48 (2H, brs), 6.38 (1H, s), 4.82 (2H, d, J=5.8 Hz).

EXAMPLE 53

7-Amino-4-(thien-2-ylmethylamino)[4,3-d] pyrimidine dimesylate

The compound is obtained from 2,4-diamino,5-cyanopyridinium acetate (190 mg, 0.98 mmol), formic acid (0.23 g, 4.4 mmol) and thienylmethylamine (1.07 ml, 10 mmol) as described in a previous experimental. The crude product is converted into a dimesylate salt as described previously and recrystallized from Pr$^i$OH to give 7-amino-4-(thien-2-ylmethylamino)pyrido[4,3-d]pyrimidine dimesylate in 19% yield. 1H NMR (DMSO δ 10.67 (1H, t, J=5.8 Hz), 9.21 (1H, s), 8.77 (1H, s), 7.48 (1H, dd, J=5.1, 1.2 Hz) 7.16 (1H, dd, J=3.4, 0.7 Hz), 7.02 (1H, dd, J=4.8, 3.4 Hz), 6.42 (1H, s), 5.06 (2H, d, J=5.7 Hz), 2.41 (6H, s).

EXAMPLE 54

7-Acetylamino-4-benzylaminopyrido[4,3-d] pyrimidine

7-Acetylamino-4-methylthiopyrido[4,3-d]pyrimidine. Acetyl chloride (0.70 mL, 9.84 mmol) is added to a solution of 7-amino-4-methylthiopyrido[4,3-d]pyrimidine (0.20 g, 1.04 mmol) (described in a previous experimental) and Eton (1.51 mL, 10.8 mmol) in THF at 0° C., and then the mixture is stirred at 20° C. for 4 h. Water (50 mL) was added, then the solution was extracted with EtOAc (3×50 mL). Evaporation and chromatography on alumina (1% EtOH/CHCl$_3$) yields 7-acetylamino-4-methylthiopyrido[4,3-d]pyrimidine (0.12 g, 49%) as a yellow solid. $^1$H NMR (DMSO) δ 11.05 (1H, s), 9.30 (1H, s), 9.02 (1H, s), 8.38 (1H, s), 2.71 (3H, s), 2.18 (3H, s).

7-Acetylamino-4-benzylaminopyrido[4,3-d]pyrimidine. A mixture of 7-acetylamino-4-methylthiopyrido[4,3-d] pyrimidine (0.40 g, 1.71 mmol) and benzylamine (1.0 mL, 9.15 mmol) is stirred under N$_2$ at 140° C. for 1 h, and the resulting product is chromatographed on silica gel (EtOAc) to give 7-acetylamino-4-benzylaminopyrido[4,3-d] pyrimidine (0.31 g, 62%) as a white solid. $^1$H NMR (DMSO) δ 10.79 (1H, s), 9.42 (1H, s), 9.23 (1H, t, J=5.8 Hz), 8.49 (1H, s), 8.18 (1H, s), 7.39 (1H, dt, J$_d$=6.9 Hz, J$_t$=1.7 Hz), 7.34 (1H, tt, J=7.3, 1.7 Hz), 7.25 (1H, tt, J=7.1, 1.7 Hz), 4.80 (2H, d, J=5.8 Hz), 2.15 (3H, s).

EXAMPLE 55

4-Anilinopyrido[3,4-d]pyrimidine

4-Carboxamidonicotinic acid. 3,4 -Pyridine dicarboxylic anhydride (8.3 g, 55.6 mmol) is added to conc NH$_4$OH (12 mL) in H₂O (60 mL) stirred at 0° C. over 5 min. Upon addition a paste forms which is stirred for 1 h at room temperature. The white paste is sparged with N₂ for 30 rain and diluted with H₂O (10 mL) to form a clear solution. Then SO₂ is bubbled through the solution for 15 min reducing its pH to 2. Upon cooling the resulting solid is filtered, rinsed with H₂O, and oven dried to yield 4-carboxamidonicotinic acid (7 g, 76%) as a white solid. ¹H NMR (DMSO) δ 8.93 (1H, s), 8.76 (1H, d, J=5.0 Hz), 8.08 (1H, s), 7.62 (1H, s), 7.45 (1H, d, J=5.0 Hz).

Isoquinolinic imide. 4-Carboxamidonicotinic acid (280 mg, 1.68 mmol) is heated neat at 200° C. for 5 h to yield isoquinolinicimide (177.2 mg, 71%) as a white solid. ¹H NMR (DMSO) δ 11.68 (1H, s), 9.12–9.03 (2H, m), 7.80 (1H, d, J=5.1 Hz).

3-Amino isonicotinic acid. Bromine (1.71 g) is added to 10% KOH (30 mL) on ice. The resulting solution is added to finely ground isoquinolinic imide (1.46 g, 9.86 mmol). Upon addition the mixture begins to foam. When all of the solid is dissolved up aqueous KOH (15%, 7 mL) is added and the mixture is heated to 80° C. for 1 min then cooled. The mixture is neutralized with SO₂, and cooled to 0° C. until precipitation occurs. The solid is collected by suction filtration and washed with H₂O, and dried in a vacuum oven to yield of 3-amino isonicotinic acid (485 mg, 36%) as a white solid. ¹H NMR (DMSO) δ 9.5–8.8 (2H, brs), 8.20 (1H, s), 7.70 (1H, d, J=5 Hz), 7.46 (1H, d, J=5 Hz).

3H-Pyrido[3,4-d]pyrimid-4-one. A mixture of 3-amino isonicotinic acid (485 mg, 3.51 mmol) in formamide (3 mL) is heated to 160° C. for 12 h. Upon cooling, the resulting solid is filtered and washed with H₂O and dried in a vacuum oven to yield 3H-pyrido[3,4-d]pyrimid-4-one (373 mg, 72%). ¹H NMR (DMSO) δ 12.60 (1H, brs), 9.06 (1H, s), 8.68 (1H, d, J=5.3 Hz), 8.23 (1H, s), 7.96 (1H, d, J=5.1 Hz).

4-Thiopyrido[3,4-d]pyrimidine. Phosphorous pentasulfide (1.25 g, 2.74 mmol) is added to a solution of 3H-pyrido [3,4-d]pyrimid-4-one (366 mg, 2.49 mmol) in pyridine (4 mL). The mixture is refluxed for 4 h under N₂. The resulting black tar is dissolved in H₂O, and a solid forms. The solid is filtered and washed with H₂O and dried in a vacuum oven to yield 4-thiopyrido[3,4-d]pyrimidine (369.8 mg, 91%) as a yellow solid. ¹H NMR (DMSO) δ 14.48 (1H, brs), 9.13 (1H, s), 8.70 (1H, d, J=5.4 Hz), 8.29 (1H, s), 8.27 (1H, d, J=5.4 Hz).

4-Methylthiopyrido[3,4-d]pyrimidine. A mixture of 4-thiopyrido[3,4-d]pyrimidine (369.8 mg, 2.26 mmol), triethylamine (0.6 mL, 4.5 mmol), DMSO (2 mL), and iodomethane (0.24 mL, 3.96 mmol) is stirred under N2 at 25° C. for 12 h. The mixture is poured into H₂O and the resulting solid is filtered and dried in a vacuum oven to yield 4-methylthiopyrido[3,4-d]pyrimidine (222 mg, 55%) as a brown solid. ¹H NMR (DMSO) δ 9.51 (1H, s), 9.18 (1H, S), 8.79 (1H, d, J=8 Hz), 7.97 (1H, d, J=8 Hz).

4-Anilinopyrido[3,4-d]pyrimidine. A mixture of 4-methylthiopyrido[3,4-d]pyrimidine (75 mg, 0.42 mmol), and aniline (1 mL) is heated to 100° C. under N₂ for 2 h. The reaction mixture is then chromatographed on silica using MPLC and eluting with a gradient system (CHCl₃ to 5% MeOH in CHCl₃). The fractions are concentrated under reduced pressure, and the resulting solid is recrystallized from Et₂O to yield 4-anilinopyrido[3,4-d]pyrimidine (21.2 mg, 23%) as a yellow solid. ¹H NMR (DMSO) δ 10.09 (1H, s), 9.18 (1H, s), 8.74 (1H, d, J=5.3 Hz), 8.46 (1H, d, J=5.8 Hz), 7.89 (2H, d, J=8.5 Hz), 7.45 (2H, t, J=7.9 Hz), 7.21 (1H, t, J=7.4 Hz).

EXAMPLE 56

4-(3-Bromoanilino)pyrido[3,4-d]pyrimidine

A mixture of 4-methylthiopyrido[3,4-d]pyrimidine (75 mg, 0.42 mmol) (see previous experimental), and 3-bromoaniline (1 mL) is heated to 100° C. under N₂ for 2 h. The reaction mixture is then chromatographed on silica using MPLC and eluting with a gradient system (CHCl₃ to 5% MeOH in CHCl₃). The fractions are concentrated under reduced pressure, and the resulting solid is recrystallized from Et₂O to yield 4-(3-bromoanilino)pyrido[3,4-d] pyrimidine (66 mg, 52.7%) as a light brown solid. ¹H NMR (DMSO) δ 10.15 (1H, s), 9.21 (1H, s), 8.80 (1H, s), 8.76 (1H, d, J=5.8 Hz), 8.44 (1H, d, J=5.6 Hz), 8.25 (1H, s), 7.93 (1H, d, J=7.7 Hz), 7.45–7.37 (2H, m).

EXAMPLE 57

4-(3-Bromoanilino)-6-fluoropyrido[3,4-d]pyrimidine

5-[N-(tert-Butoxycarbonyl)amino]-2-fluoropyridine. 5-Amino-2-fluoropyridine is prepared by hydrogenation (Pd/C) of 2-fluoro-5-nitropyridine (obtained from from 2-chloro-5-nitropyridine by reaction with KF in MeCN with Ph₄PBr [J. H. Clark and D. J. Macquarrie, *Tetrahedron Lett.*, 1987, 28, 111–114]. Reaction of the crude amine with t-Boc anhydride gives 5-[N-(tert-butoxycarbonyl)amino]-2-fluoropyridine. ¹H NMR (CDCl₃ δ 8.07 (1H, s), 8.05 (1H, m), 6.89 (1H, dd, J=9.2, 3.3 Hz), 6.66 (1H, m), 1.52 (9H, s).

5-[N-(tert-Butoxycarbonyl)amino]-2-fluoropyridine-4-carboxylic acid. Reaction of 5-[N-(tert-butoxycarbonyl) amino]-2-fluoropyridine (5.3 g, 25 mmol) sequentially with n-BuLi and CO₂ as described in the following example gives 5-[N-(tert-butoxycarbonyl)amino]-2-fluoropyridine-4-carboxylic acid (1.60 g, 25%). ¹H NMR (DMSO) δ 9.83 (1H, brs), 8.84 (1H, s), 7.49 (1H, d, J=2.9 Hz), 1.47 (9H, s).

5-Amino-2-fluoropyridine-4-carboxylic acid. Reaction of 5-[N-(tert-butoxycarbonyl)amino]-2-fluoropyridine-4-carboxylic acid (1.0 g, 3.9 mmol) with TFA as described above gives 5-amino-2-fluoropyridine-4-carboxylic acid (0.46 g, 74%). ¹H NMR (DMSO) δ 7.85 (1H, d, J=1.5 Hz), 7.23 (1H, d, J=2.5 Hz).

6-Fluoro-3H-pyrido[3,4-d]pyrimidin-4-one. Reaction of 5-amino-2-fluoropyridine-4-carboxylic acid with formamide at 140° C. as above gave 6-fluoro-3H-pyrido[3,4-d] pyrimidin-4-one (~20%). ¹H NMR (DMSO) δ 12.48 (1H, m), 8.74 (1H, s), 8.16 (1H, s), 7.63 (1H, d, J=3 Hz).

4-(3-Bromoanilino)-6-fluoropyrido[3,4-d]pyrimidine. Reaction of 6-fluoro-3H-pyrido[3,4-d]pyrimidin-4-one (0.60 g, 3.6 mmol) with POCl₃, followed by reaction of the crude 4,6-dihalo compound with 3-bromoaniline gives 4-(3-bromoanilino)-6-fluoropyrido[3,4-d]pyrimidine (0.73 g, 63%). ¹H NMR (DMSO) δ 10.09 (1H, brs), 8.96 (1H, s), 8.75 (1H, s), 8.25 (2H, m), 7.90 (1H, brd, J=6.5 Hz), 7.44 –7.34 (2H, m).

EXAMPLE 58

4-(3-Bromoanilino)-6-chloropyrido[3,4-d]pyrimidine

5-[N-(tert-butoxycarbonyl)amino]-2-chloropyridine. A mixture of 5-amino-2-chloropyridine (12.86 g, 0.1 mol), di-tert-butyldicarbonate (24.0 g, 0.11 mol) and Eton (12.1 g, 1.12 mol) in CH₂Cl₂ (150 mL) is heated under reflux for 12 h, cooled, and the precipitate is filtered off. The organic layer is washed with water, dried (CaCl₂) and filtered through a short column of alumina. Removal of the solvent gives 5-[N-(tert-butoxycarbonyl)amino]-2-chloropyridine (11.9 g, 52%). ¹H NMR (CDCl₂) δ 8.31 (1H, d, J=2.9 Hz), 7.94 (1H, dd, J=8.6, 2.6 Hz), 7.24 (1H, d, J=8.7 Hz), 7.15 (1H, m), 1.51 (9 H, s).

5-[N-(tert -Butoxycarbonyl)amino]-2-chloropyridine-4-carboxylic acid. A solution of 5-[N-(tert-butoxycarbonyl)

amino]-2-chloropyridine (22.87 g, 0.1 mol) and TMEDA (47 mL, 0.31 mol) in dry Et$_2$O (600 mL) is cooled to −78° C., and n-BuLi (10M in hexanes, 30 mL, 0.3 mol) is added dropwise. The solution is allowed to warm to −10° C. and is then kept at that temperature for 2 h, before being recooled to −78° C. Dry CO$_2$ is then bubbled in, and the resulting mixture is allowed to warm to 20° C., before being quenched with water (300 mL) containing a small amount of NH$_4$OH. The resulting aqueous layer is washed with EtOAc, then acidified slowly with dilute HCl to precipitate 5-[N-(tert-butoxycarbonyl)amino]-2-chloropyridine-4-carboxylic acid (15.5 g, 57%). $^1$H NMR (DMSO) δ 10.00 (1H, s), 9.13 (1H, s), 7.74 (1H, s), 1.47 (9H, s).

5-Amino-2-chloropyridine-4-carboxylic acid. A stirred suspension of 5-[N-(tert-butoxycarbonyl)amino]-2-chloropyridine-4-carboxylic acid (1.91 g, 7 mmol) in CH$_2$Cl$_2$ (200 mL) is treated slowly with trifluoroacetic acid until homogeneous (ca. 12 mL). The solution is stirred overnight and extracted with dilute NH$_4$OH, and the aqueous layer is then acidified with dilute HCl to gave a precipitate of 5-amino-2-chloropyridine-4-carboxylic acid (1.05 g, 87% yield). $^1$H NMR (DMSO) δ 9.01 (2H, m), 8.03 (1H, s), 7.48 (1H, s).

6-Chloro-3H-pyrido[3,4-d]pyrimidin-4-one. A solution of 5-amino-2-chloropyridine-4-carboxylic acid (8.1 g, 4.7 mmol) in formamide (100 mL) is stirred at 140° C. for 12 h. Dilution of the cooled mixture with water gives a precipitate of 6-chloro-3H-pyrido[3,4-d]pyrimidin-4-one (7.3 g, 86% yield). $^1$H NMR (DMSO) δ 12.73 (1H, m), 8.90 (1H, d, J=0.7 Hz), 8.23 (1H, s), 7.97 (1H, d, J=0.7 Hz).

4,6-Dichloropyrido[3,4-d]pyrimidine. A stirred suspension of 6-chloropyrido[3,4-d]pyrimidin-4-one (1.82 g, 10 mmol) in POCl$_3$ (10 mL) is heated under reflux until dissolved (ca. 2 h) and for a further 30 min. Excess reagent is removed under reduced pressure, and the residue is treated with a mixture of CH$_2$Cl$_2$ and ice-cold aqueous Na$_2$CO$_3$. The resulting organic layer is dried (Na$_2$SO$_4$) and evaporated to give a quantitative yield of crude, unstable, 4,6-dichloropyrido[3,4-d]pyrimidine, which is used directly in the next step. $^1$H NMR (CDCl$_3$) δ 9.38 (1H, d, J=0.5 Hz), 9.19 (1H, s), 8.09 (1H, d, J=0.5 Hz).

4-(3-Bromoanilino)-6-chloropyrido[3,4-d]pyrimidine. A mixture of the above crude dichloropyrimidine and 3-bromoaniline (3.8 g, 22 mmol) is dissolved in i-PrOH (100 mL). One drop of conc. HCl is added to initiate the reaction, and the mixture is then heated under reflux for 30 min, cooled, and diluted with water to precipitate 4-(3-bromoanilino)-6-chloropyrido[3,4-d]pyrimidine (1.26 g, 38% yield). $^1$H NMR (DMSO) δ 10.12 (1H, s), 9.03 (1H, s), 8.77 (1H, s), 8.63 (1H, s), 8.21 (1H, s), 7.89 (1H, d, J=8.1 Hz), 7.43–7.32 (2H, m).

EXAMPLE 59

4-(3-Bromoanilino)-6-methoxypyrido[3,4-d]
pyrimidine

Treatment of 4-(3-bromoanilino)-6-fluoropyrido[3,4-d] pyrimidine (see a previous experimental) at 100° C. in a pressure vessel with sodium methoxide in methanol gives 4-(3-bromoanilino)-6-methoxypyrido[3,4-d]pyrimidine. $^1$H NMR (DMSO) δ 9.93 (1H, s), 8.94 (1H, s), 8.61 (1H, s), 8.26 (1H, brs), 7.94 (1H, brd, J=7.6 Hz), 7.88 (1H, s), 7.43 −7.32 (2H, m), 4.01 (3H, s).

EXAMPLE 60

4-(3-Bromoanilino)-6-methylaminopyrido[3,4-d]
pyrimidine

Treatment of 4-(3-bromoanilino)-6-fluoropyrido[3,4-d] pyrimidine (0.20 g, 0.63 mmol) (see a previous experimental) at 100° C. in a pressure vessel with methylamine in ethanol followed by chromatography on alumina (CH$_2$Cl$_2$/MeOH, 99:1) gives 4-(3-bromoanilino)-6-methylaminopyrido[3,4-d]pyrimidine (0.07 g, 34%). $^1$H NMR (DMSO) δ 9.69 (1H, s), 8.75 (1H, s), 8.41 (1H, s), 8.21 (1H, brs), 7.93 (1H, brd, J=7.6 Hz), 7.41–7.28 (2H, m), 7.06 (1H, s), 6.82 (1H, q, J=5.0 Hz), 4.95 (3H, d, J=5.0 Hz).

EXAMPLE 61

4-(3-Bromoanilino)-6-dimethylaminopyrido[3,4-d]
pyrimidine

Treatment of 4-(3-bromoanilino)-6-fluoropyrido[3,4-d] pyrimidine (see a previous experimental) at 100° C. in a pressure vessel with dimethylamine in ethanol gives 4-(3-bromoanilino)-6-dimethylaminopyrido[3,4-d]pyrimidine. $^1$H NMR (DMSO) δ 9.71 (1H, s), 8.83 (1H, s), 8.43 (1H, s), 8.21 (1H, brs), 7.94 (1H, brd, J=7.5 Hz), 7.42–7.29 (2H, m), 7.26 (1H, s), 3.17 (6H, s).

EXAMPLE 62

4-(Benzylamino)pyrido[3,4-d]pyrimidine

A mixture of 4-methylthiopyrido[3,4-d]pyrimidine (74 mg, 0.41 mmol)(see a previous experimental), and benzylamine (1 mL) is heated to 100° C. for 2 h. On cooling the mixture is concentrated under reduced pressure and purified directly by preparative tlc on silica gel eluting with CH$_2$Cl$_2$, to yield 4-(benzylamino)pyrido[3,4-d]pyrimidine (21.2 mg, 20%). 1H NMR (DMSO) δ 9.21 (1H, t, J=5.8 Hz), 9.19 (1H, s), 8.63 (1H, d, J=5.8 Hz), 8.58 (1H, s), 8.20 (1H, d, J=5.1 Hz), 7.41–7.30 (4H, m), 7.26 (1H, t, J=7.1 Hz).

EXAMPLE 63

4-(3-Bromoanilino)pyrido[2,3-d]pyrimidine 3H-pyrido[2,3-d]pyrimidin-4-one. 2-Amino nicotinic acid (15 g, 108.6 mmol) in formamide (35 mL) is heated to 165°–170° C. for 3.5 h. Upon cooling a solid precipitates. The solid is filtered and washed with H$_2$O and dried in a vacuum oven to give 3H-pyrido[2,3-d]pyrimidin-4-one (7.87 g, 49.4%). $^1$H NMR (DMSO) δ 12.50 (1H, s),8.97 (1H, dd, J=1.9, 4.5 Hz), 8.53 (1H, dd, J=2.1, 7.9 Hz), 8.34 (1H, s), 7.57 (1H, dd, J=4.6, 8.0 Hz).

4-Thiopyrido[2,3-d]pyrimidine. Phosphorous pentasulfide (6 g, 13.5 mmol) is added to a solution of 3H-pyrido [2,3-d]pyrimidin-4-one (2 g, 13.5 mmol) in pyridine (50 mL). The mixture is refluxed for 3 h. Upon cooling a solid formed and the pyridine is decanted off. The solid is suspended in H$_2$O (20 mL) and then filtered and dried in a vacuum oven to yield 4-thiopyrido[2,3-d]pyrimidine (1.72 g, 78%). $^1$H NMR (DMSO) δ 9.06 (1H, dd, J=1.9, 4.3 Hz), 8.90 (1H, dd, J=1.9, 8.2 Hz), 8.36 (1 H, s), 7.65 (1H, dd, J=4.3, 8.2 Hz).

4-Methylthiopyrido[2,3-d]pyrimidine. A mixture of 4-thiopyrido[2,3-d]pyrimidine (100 mg, 0.76 mmol), triethylamine (154 mg, 1.52 mmol), DMSO (2 mL), and iodomethane (161 mg, 1.14 mmol) is stirred for 12 h at 25° C. The mixture is poured into H$_2$O and extracted with EtOAc. The combined extracts are washed with water, saturated brine, and dried (MgSO$_4$), and the solvent is removed under reduced pressure to yield 4-methylthiopyrido[2,3-d]pyrimidine (134 mg, quant.). $^1$H NMR (DMSO) δ 9.25 (1H, dd, J=1.8, 4.2 Hz), 9.17 (1H, s), 8.59 (1H, dd, J=1.9, 8.2 Hz), 7.75 (1H, dd, J=4.3, 8.2 Hz), 2.73 (3H, s).

A mixture of 4-methylthiopyrido[2,3-d]pyrimidine (157 mg, 0.89 mmol, and 3-bromoaniline (1 mL) is heated to 100° C. for 2 h. On cooling a precipitate forms which is filtered then washed with EtOH and air dried to yield 4-(3-bromoanilino)pyrido[2,3-d]pyrimidine (55.5 mg, 20%. $^1$H NMR (DMSO) δ 10.13 (lit, s), 9.11 (1H, dd, J=1.7, 4.3 Hz), 9.01 (1H, dd, J=1.7, 8.2 Hz), 8.81 (1H, s), 8.22 (1H, s), 7.90 (1H, d, J=7.7 Hz), 7.71 (1H, dd, J=4.3, 8.0 Hz), 7.40 (2H, m).

EXAMPLE 64

4-(3-Bromoanilino)-7-fluoropyrido[2,3-d]pyrimidine 2,6-Difluoronicotinic acid. 2,6-Difluoropyridine (7.89 mL, 0.087 mmol) is added dropwise under $N_2$ at 78° C. to a stirred solution of lithium diisopropylamide (59.0 mL of a 1.5N solution in cyclohexane, 0.089 mmol) in THF (250 mL). After 2 h at 78° C., a stream of dry $CO_2$ is passed through the solution and the mixture is diluted with water and washed with EtOAc. The aqueous portion is neutralized with 3N HCl, extracted with EtOAc and worked up to give 2,6-difluoronicotinic acid (13.4 g, 97%). $^1$H NMR (DMSO) δ 8.59 (1H, dd, J=9.2, 8.2 Hz), 7.30 (1H, dd, J=8.2, 2.1 Hz), 4.03 (1H, brs).

2,6-Difluoronicotinamide. A solution 2,6-difluoronicotinic acid (7.4 g, 0.046 mmol) and $SOCl_2$ (20 mL) in 1,2-dichloroethane (60 mL) containing DMF (1 drop) is heated under reflux for 4 h, then concentrated to dryness under reduced pressure. The residue is dissolved in $Et_2O$ (100 mL), cooled to 0° C., and treated dropwise with concentrated ammonia (10.0 mL, 0.17 mmol). After 10 min the solution is washed with aqueous $NaHCO_3$ and worked up to give 2,6-difluoronicotinamide (5.61 g, 76%). $^1$H NMR ($CDCl_3$) δ 8.70 (1H, dd, J=9.6, 8.3 Hz), 7.00 (1H, ddd, J=8.3, 2.9, 1.1 Hz), 6.71, 6.55 (1H, 1H, 2 brs).

2-Amino-6-fluoronicotinamide. A solution of 2,6-difluoronicotinamide (4.68 g, 0.029 mmol) in dry formamide (30 mL) is saturated with ammonia and allowed to stand at room temperature for 24 h. Water (50 mL) is added and the resultant precipitate is filtered off and washed well with water, to give 6-amino-2-fluoronicotinamide (1.41 g, 31%) mp 236°–237° C. $^1$H NMR (DMSO) δ 7.89 (1H, dd, J=10.4, 8.4 Hz), 7.31, 7.16 (1H, 1H, 2 brs,), 6.93 (2H, brs), 6.36 (1H, dd, J=8.4, 2.4 Hz).

The filtrate and washings are combined and extracted exhaustively with EtOAc, and the extract is chromatographed on silica gel. EtOAc/petroleum ether (1:1) elutes forerun, while EtOAc/petroleum ether (2:1) and then EtOAc gives 2-amino-6-fluoronicotinamide (1.57 g, 35%), mp (EtOAc/petroleum ether) 199°–200° C. [Rogers, R. B. et al., U.S. Pat. No. 4,383,851, record mp 198°–200° C.]. $^1$H NMR (DMSO) δ 8.13 (1H, dd, J=10.4, 8.4 Hz), 7.90, 7.30 (1H, 1H, 2 brs), 7.65 (2H, brs), 6.23 (1H, dd, J=8.4, 2.6 Hz).

A suspension of 2-amino-6-fluoronicotinamide (0.74 g, 4.77 mmol) in triethyl orthoformate (25 mL) is heated at reflux for 8 h. After cooling to room temperature the precipitate is filtered off and washed well with petroleum ether to give 7-fluoropyrido[2,3-d]pyrimid-4(3H)-one (0.76 g, 96%), $^1$H NMR (DMSO) δ 12.75 (1H, brs), 8.66 (1H, dd, J=10.4, 8.4 Hz), 8.38 (1H, s), 7.33 (1H, dd, J=8.4, 2.6 Hz).

4-(3-Bromoanilino)-7-fluoropyrido[2,3-d]pyrimidine. A suspension of 7-fluoropyrido[2,3-d]pyrimid-4(3H)-one (0.20 g, 1.21 mmol) in $POCl_3$ (10 mL) is heated under reflux for 2 h. The volatiles are then removed under reduced pressure, and the residue is partitioned between aqueous NaHCl and EtOAc. The organic extract is worked up to give crude 4-chloro-7-fluoropyrido[2,3-d]pyrimidine, which is used directly in the next reaction. A solution of this product (0.20 g, 1.09 mmol) and 3-bromoaniline (0.23 mL, 2.18 mmol) in propan-2-ol (1.0 mL) and THF (10 mL) containing a trace of conc. HCl is stirred at 20° C. for 1 h, and then concentrated to dryness. The residue is dissolved in EtOAc, washed with aqueous $NaHCO_3$, and worked up to give an oil, which is chromatographed on silica gel. Elution with EtOAc/petroleum ether (1:5) gives 3-bromoaniline, while EtoAc/petroleum ether (1:1) elutes 4-(3-bromoanilino)-7-fluoropyrido[2,3-d]pyrimidine (0.18 g, 47%), mp (MeOH) 211°–213° C. $^1$H NMR (DMSO) δ 10.18 (1H, brs), 9.17 (1H, t, J=8.6 Hz), 8.80 (1H, s), 8.17 (1H, t, J=1.8 Hz), 7.85 (1H, dt, $J_d$=7.6 Hz, $J_t$=1.8 Hz), 7.53 (1H, dd, J=8.6, 2.7 Hz), 7.41–7.34 (2H, m).

EXAMPLE 65

7-Amino-4-(3-bromoanilino)pyrido[2,3-d]pyrimidine

A solution of 4-(3-bromoanilino)-7-fluoropyrido[2,3-d]pyrimidine (0.20 g, 0.63 mmol) in EtOH (20 mL) is saturated with ammonia and warmed at 100° C. in a pressure vessel for 30 h. The solvent is removed under reduced pressure to give 7-amino-4-(3-bromoanilino)pyrido[2,3-d]pyrimidine (0.18 g, 90%). $^1$H NMR (DMSO) δ 9.97 (1H, brs), 8.59 (1H, s), 8.51 (1H, d, J=9.3 Hz), 8.11 (1H, s, brs), 7.77 (1H, brd, J=6.3 Hz), 7.44 (2H, brs), 7.37–7.30 (2H, m), 6.81 (1H, d, J=9.3 Hz).

EXAMPLE 66

4-(3-Bromoanilino)-7-methylaminopyrido[2,3-d]pyrimidine

A solution of 4-(3-bromoanilino)-7-fluoropyrido[2,3-d]pyrimidine (see a previous experimental) (0.20 g, 0.63 mmol), methylamine hydrochloride (0.13 g, 1.88 mmol) and $Et_3N$ (0.30 mL) 2.19 mmol) in EtOH (15 mL) is heated at 100° C. in a pressure vessel for 18 h. The solvent is removed under reduced pressure, and the residue is partitioned between EtOAc and water. Workup of the organic layer gives 4-(3-bromoanilino)-7-(methylamino)pyrido[2,3-d]pyrimidine (0.16 g, 77%). $^1$H NMR (DMSO) δ 9.53 (1H, s), 8.54 (1H, s), 8.41 (1H, d, J=8.1 Hz), 8.17 (1H, t, J=1.8 Hz), 7.83 (1H, dd, J=8.0, 1.9 Hz), 7.66 (1H, brs), 7.32 (1H, t, J=8.0 Hz), 7.24 (1H, dd, J=8.0, 1.8 Hz), 6.77 (1H, d, J=8.1 Hz), 2.92 (3H, d, J=4.8 Hz).

EXAMPLE 67

4-(3-Bromoanilino)-7-dimethylaminopyrido[2,3-d]pyrimidine

Reaction of 4-(3-bromoanilino)-7-fluoropyrido[2,3-d]pyrimidine (see a previous experimental) (0.12 g, 0.38 mmol) with dimethylamine hydrochloride (92 mg, 1.13 mmol) and $Et_3N$ (0.18 mL, 1.32 mmol) in EtOH (15 mL) at 100° C. for 18 h in a pressure vessel, followed by evaporation of the solvent and workup, gives 4-(3-bromoanilino)-7-(dimethylamino)pyrido[2,3-d]pyrimidine (0.11 g, 84%). $^1$H NMR (DMSO) δ 9.58 (1H, brs), 8.56 (1H, d, J=9.3 Hz), 8.54 (1H, s), 8.18 (1H, t, J=1.9 Hz), 7.84 (dt, $J_d$=8.0, Hz, $J_t$=1.9 Hz), 7.33 (1H, dd, J=8.1, 8.0 Hz) 7.25 (1H, dt, $J_d$=9.3, Hz, $J_t$=1.9 Hz), 7.10 (1H, d, J=9.3 Hz), 3.18 (6H, s).

EXAMPLE 68

4-(3-Bromoanilino)-7-methoxypyrido[2,3-d]pyrimidine

A solution of 4-(3-bromoanilino)-7-fluoropyrido[2,3-d]pyrimidine (0.26 g, 0.81 mmol) and sodium methoxide (prepared from 75 mg of sodium, 3.26 mmol) in dry MeOH (15 mL) is heated at 90° C. in a pressure vessel for 18 h. The mixture is poured into water and extracted with EtOAc to give 4-(3-bromoanilino)-7-methoxypyrido[2,3-d] pyrimidine (0.23 g, 86%). $^1$H NMR (DMSO) δ 9.88 (1H, brs), 8.82 (1H, d, J=8.9 Hz), 8.71 (1H, s), 8.18 (1H, dd, J=8.0, 1.9 Hz), 7.36 (1H, dd, J=8.1, 8.0 Hz), 7.29 (1H, ddd, J=8.1, 1.9, 1.9 Hz) 7.15 (1H, d, J=8.9 Hz), 4.01 (3H, s).

EXAMPLE 69

4-Benzylamino-7-methylaminopyrimido[4,5-d] pyrimidine

S-Ethylisothiouronium iodide. A solution of thiourea (3.80 g, 50 mmol) and iodoethane (4 mL, 50 mmol) in MeOH (100 mL) is refluxed for 24 h. The solvent is stripped under reduced pressure, and the residual light yellow oil, is dried under vacuum, solidifying spontaneously. The desired compound (13.98 g) is obtained quantitatively.

4-Amino-5-cyano-2-ethylthiopyrimidine. A suspension of NaOMe (2.7 g, 50 mmol) in EtOH (200 mL) is added to a mixture of S-ethylisothiourea hydroiodide (11.58 g, 50 mmol), ethoxymethylidenemalononitrile (6.1 g, 50 mmol) and ethanol (250 mL) at 25° C. The reaction mixture is refluxed under N$_2$ for 2 h, and then the solution is concentrated on a hot plate until precipitation is observed. After cooling, the solid is collected by suction filtration and is stirred in water at 25° C. Filtration and vacuum oven drying affords 4-amino-5-cyano-2-ethylthiopyrimidine (4.02 g, 45%) as a brown solid. $^1$H NMR δ (DMSO) 8.45 (1H, s), 7.90 (2H, brs), 3.00 (2H, q, J=7.3 Hz), 1.27 (3H, t, J=7.3 Hz).

4-Amino-2-ethylthiopyrimidine-5-carboxamide. 4-Amino-5-cyano-2-ethylthiopyrimidine (4.0 g, 22.3 mmol) is added to sulfuric acid (conc., 4.3 mL) in small portions. The mixture is then stirred under N$_2$ at 40° C. for 1.5 h. The reaction is quenched with ice-water and NH$_4$OH is used to adjust the pH to ~9. The solid is collected via suction filtration and dried in a vacuum oven overnight. 4-Amino-2-ethylthiopyrimidine-5-carboxamide (2.58 g, 58%) is obtained as a light brown solid. $^1$H NMR: (DMSO) δ 8.52 (1H, s), 7.98 (2H, brs), 7.42 (2H, brs), 3.04 (2H, q, J=7.3 Hz), 1.27 (3H, t, J=7.3 Hz).

4-Oxo-7-ethylthio-3H-pyrimido[4,5-d]pyrimidine. A mixture of 4-amino-2-ethylthiopyrimidine-5-carboxamide (4.66 g, 23.5 mmol) and triethyl orthoformate (150 mL) is refluxed under N$_2$ for 24 h, and is then cooled to 25° C. The brown solid is isolated by suction filtration and dried in a vacuum oven to give 4-oxo-7-ethylthio-3H-pyrimido[4,5-d] pyrimidine (3.54 g, 72%). $^1$H NMR: (DMSO) δ 12.80 (1H, s), 9.20 (1H, s), 8.45 (1H, s), 3.18 (2H, q, J=7.4 Hz), 1.35 (3H, t, J=7.4 Hz).

4-Thiono-7-ethylthio-3H-pyrimido[4,5-d]pyrimidine. A mixture of 4-oxo-7-ethylthio-3H-pyrimido[4,5-d] pyrimidine (1.33 g, 6.7 mmol), P$_2$S$_5$ (1.48 g, 6.6 mmol) and pyridine (15 mL) is refluxed under N$_2$ for 3 h. The pyridine is then stripped under reduced pressure, and the residue is dissolved in NaOH solution (0.5M, 75 mL) and boiled with charcoal. After filtration, the filtrate is neutralized with acetic acid to generate a gold brown solid. Buchner filtration and drying in a vacuum oven affords 4-thiono-7-ethylthio-3H-pyrimido[4,5-d]pyrimidine (1.42 g, 95%). $^1$H NMR (DMSO) δ 9.47 (1H, s), 8.46 (1H, s), 3.20 (2H, q, J=7.3 Hz), 1.35 (3H, t, J=7.3 Hz).

7-Ethylthio-4-methylthiopyrimido[4,5-d]pyrimidine. The same procedure described for 7-amino-4-methylthiopyrido [4,3-d]pyrimidine in Example 21 is used. $^1$H NMR (DMSO) δ 9.52(1H, s), 9.15 (1H, s), 3.23 (2H, q, J=7.3 Hz), 2.72 (3H, s), 1.38 (3H, t, J=7.3 Hz).

4-Benzylamino-7-ethylthiopyrimido[4,5-d]pyrimidine. The same procedure described for 7-amino-4-anilinopyrido [4,3-d]pyrimidine in example 21 is used.

4-Benzylamino-7-methylaminopyrimido[4,5-d] pyrimidine. 4-Benzylamino-7-ethylthiopyrimido[4,5-d] pyrimidine in EtOH containing excess methylamine is heated to 150° C. in a stainless steel bomb for 5 h. The solid is filtered off and dried to give 4-benzylamino-7-methylaminopyrimido[4,5-d]pyrimidine.

EXAMPLE 70

4-Benzylamino-7-hydrazinopyrimido[4,5-d] pyrimidine

4-Benzylamino-7-ethylthio pyrimido[4,5-d]pyrimidine in EtOH containing excess hydrazine is heated to 150° C. in a stainless steel bomb for 5 h. The solid is filtered off and dried to give 4-benzylamino-7-hydrazinopyrimido[4,5-d] pyrimidine.

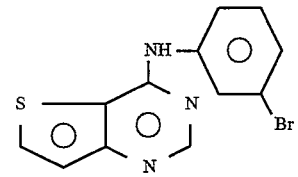

EXAMPLE 71

4-(3-Bromoanilino)thieno[3,2-d]pyrimidine hydrochloride

3H-Thieno[3,2-d]pyrimid-4-one. A mixture of methyl 3-aminothiophene-2-carboxylate (1 g, 6.3 mmol) and formamide (2 g) is heated at 240° C. for 10 min. Upon cooling a precipitate appeared. It is dissolved in EtOH and filtered. The filtrate is concentrated under reduced pressure and the residue is purified by silica gel chromatography eluting with 10% MeOH in CH$_2$Cl$_2$ to yield 3H-thieno[3,2-d]pyrimid-4-one (249 mg, 26%) as a solid. $^1$H NMR (DMSO) δ 12.61 (1H, brs), 8.20 (1H, s), 8.17 (1H, d, J=5 Hz), 7.42 (1H, d, J=5 Hz).

4-Chlorothieno[3,2-d]pyrimidine. To a solution of DMF (170.3 µL, 2.2 mmol) and dichloroethane (1.2 mL) at 0° C. under N$_2$, oxalyl chloride (279.2 mg, 3.2 mmol) is added slowly and stirred for 10 min. 3H-thieno[3,2-d]pyrimid-4-one (152.2 mg, 1.0 mmol) is added and refluxed for 5 h. The reaction mixture is poured into water and extracted with CH$_2$Cl$_2$. The organic layer is stripped under reduced pressure to yield 4-chlorothieno[3,2-d]pyrimidine (140 mg, 82%) as a yellow solid. $^1$H NMR (DMSO) δ 9.05 (1H, s), 8.62 (1H, d, J=5 Hz), 7.79 (1H, d, J=5 Hz).

4-(3-Bromoanilino)thieno[3,2-d]pyrimidine hydrochloride. A mixture of 4-chlorothieno[3,2-d]-pyrimidine (135 mg, 0.79 mmol) and 3-bromoaniline (95 µL, 0.89 mmol) in 2-methoxyethanol (2 mL) is heated to 79° C. for 30 min. The resulting precipitate is filtered and washed with CH$_2$Cl$_2$ to yield 4-(3-bromoanilino)thieno[3,2-d]pyrimidine hydrochloride (195.5 mg, 72%) as a light yellow solid. $^1$H NMR (DMSO) δ 11.33 (1H, s), 8.94 (1H, s), 8.23 (1H, s), 8.53 (1H, d, J=5.3 Hz), 8.07 (1H, s), 7.77 (1H, d, J=7.9 Hz), 7.6 (1H, d, J=5.3 Hz), 7.48 (2H, m).

EXAMPLE 72

4-Benzylaminothieno[3,2-d]pyrimidine

As described in the previous experiment 4-chlorothieno[3,2-d]pyrimidine (100 mg, 0.586 mmol) and benzylamine (710 µL, 0.645 mmol) in 2-methoxyethanol (2 mL) yields 4-benzylaminothieno[3,2-d]pyrimidine (37 mg, 26%). $^1$H NMR (DMSO) δ 8.42 (1H, s), 8.12 (1H, d, J=5.5 Hz), 7.39 (1H, d, J=5.3 Hz), 7.40–7.30 (4H, m), 7.24 (1H, t, J=6.8 Hz).

EXAMPLE 73

4-(3-Bromoanilino)thieno[2,3-d]pyrimidine

Methyl 2-aminothiophene-3-carboxylate. A mixture of methyl cyanoacetate (3.25 g, 32.3 mmol), 1,4dithiane-2,5diol (5 g, 32.8 mmol), triethylamine (1 mL, 7.71 mmol) in EtOH (50 mL) is stirred at 40° C. for 1 h. The cooled solution is eluted through a silica plug with $CH_2Cl_2$. The filtrate is stripped to dryness to give crude methyl 2-aminothiophene-3-carboxylate which is carried on to the next reaction. $^1$H NMR (DMSO) δ 7.26 (1H, s), 6.82 (1H, d, J=5.8 Hz), 6.28 (1H, d, J=5.8 Hz), 3.69 (3H, s).

3H-Thieno[2,3-d]pyrimid-4-one. A solution of methyl 2-aminothiophene-3-carboxylate (602.1 mg, 3.83 mmol) in formamide (5 mL) is heated at 200 ° C. for 12 h. The resulting tar is dissolved in $CH_2Cl_2$ (10 mL) then placed on a silica plug and eluted with 10% MeOH in $CH_2Cl_2$. The filtrate is stripped under reduce pressure and the resulting solid is washed with EtOH to yield 3H-thieno[2,3-d]pyrimid-4-one (231.4 mg, 40%) as an orange solid. $^1$H NMR (DMSO) δ 12.50 (1H, brs), 8.13 (1H, s), 7.60 (1H, d, J=5.8 Hz), 7.41 (1H, d, J=6.0 Hz).

4-Chlorothieno[2,3-d]pyrimidine. To a solution of DMF (90 µL) and $CH_2Cl_2$ (2 mL) at 0° C. under $N_2$, oxalyl chloride (148 mg, 1.2 mmol) is added slowly and stirred for 10 min. 3H-Thieno[2,3-d]pyrimid-4-one (81 mg, 0.52 mmol) is added as a solid to the solution and warmed with a heat gun until the solid dissolves. The reaction is stirred at 25° C. for 12 h under $N_2$. The reaction mixture is poured into water and extracted with $CH_2Cl_2$. The phases are separated and the organic layer is dried ($Na_2SO_4$) and stripped under reduced pressure to yield 4-chlorothieno[2,3-d]pyrimidine (87.6 mg, 97%) as a solid. $^1$H NMR (DMSO) δ 8.96 (1H, s), 8.17 (1H, d, J=6.0 Hz), 7.62 (1H, d, J=6.0 Hz).

4-(3-Bromoanilino)thieno[2,3-d]pyrimidine hydrochloride. A mixture of 4-chlorothieno[2,3-d]pyrimidine (135 mg, 0.79 mmol) and 3-bromoaniline (95 µL, 0.89 mmol) in 2-methoxyethanol (2 mL) is heated to 79° C. for 30 min with stirring. The resulting solid is filtered and washed with $CH_2Cl_2$ to yield 4-(3-bromoanilino)thieno[2,3-d]pyrimidine hydrochloride (197 mg, 73%). $^1$H NMR (DMSO) δ 9.99 (1H, s), 8.60 (1H, s), 8.23 (1H, s), 7.98 (1H, d, J=6.0 Hz), 7.88 (1H, d, J=8.0 Hz), 7.79 (1H, d, J=6.0 Hz), 7.37 (1H, t, J=8.0 Hz), 7.30 (1H, d, J=8.0 Hz).

EXAMPLE 74

4-Benzylaminopyrrolo[2,3-d]pyrimidine

4-Benzylaminopyrrolo[2,3-d]pyrimidine is prepared as described previously. G. H. Hitchings, K. W. Ledig and R. A. West, U.S. Pat. No. 3,037,980, 1962; *Chemical Abstracts* 1962, 57, 15130c.

EXAMPLE 75

N$^6$-(3-Bromophenyl)adenine

A mixture of 6-chloropurine (1.0 g, 6.47 mmol), 3-bromoaniline (0.78 mL, 7.12 mmol), and conc HCl (4 drops) in isopropanol (10 mL) is stirred at 80° C. for 5 h. Upon cooling, it precipitates. The solid is filtered and washed with isopropanol and air dried to yield N$^6$-(3-bromophenyl)adenine (1.93 g, 91%) as a light yellow solid. $^1$H NMR (DMSO) δ 11.38 (1H, s), 8.78 (1H, s), 8.75 (1H, s), 7.90 (1H, d, J=8.0 Hz), 7.38–7.34 (2H, m).

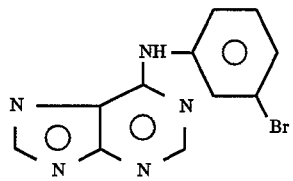

EXAMPLE 76

N$_6$-Benzyladenine

N$_6$-Benzyladenine is available commercially from the Aldrich Chemical Company, 1001 West Saint Paul Avenue, Milwaukee, Wis. 53233.

EXAMPLE 77

7-Amino-4-(3-methylanilino)pyrido[4,3-d]pyrimidine

A mixture of 7-amino-4-methylthiopyrido[4,3-d]pyrimidine (217 mg, 1.13 mmol) and m-toluidine (1.50 g, 14.0 mmol) is stirred at 155° C. for 30 min. The resulting product is chromatographed over silica gel (5% MeOH/$CH_2Cl_2$) to give 7-amino-4-(3-methylanilino)pyrido[4,3-d]pyrimidine (190 mg, 67%) as a pale yellow solid. $^1$H NMR (DMSO) δ 9.81 (1H, brs), 9.34 (1H, s), 8.38 (1H, s), 7.60 (2H, s), 7.26 (1H, dd, J=8.5, 7.6 Hz), 6.95 (1H, d, J=7.4 Hz), 6.63 (2H, brs), 6.44 (1H, s), 2.33 (3H, s).

EXAMPLE 78

7-Amino-4-(4-methoxyanilino)pyrido[4,3-d]pyrimidine

A mixture of 7-amino-4-methylthiopyrido[4,3-d]pyrimidine (129 mg, 0.62 mmol) and 4-methoxyaniline ((0.15 g, 1.2 mmol) was in ethanol (5 mL) was heated at 40° C. for 16 h, and then reflux for 3 h. The reaction mixture was cooled to 0° C. overnight, and the solid was collected by vacuum filtration and recrystalized from isopropanol to give 7-amino-4-(4-methoxyanilino)pyrido[4,3-d]pyrimidine (42 mg, 25%) as a yellow solid. $^1$H NMR (DMSO) δ 10.00 (1H, brs), 9.31 (1H, s), 8.35 (1H, s), 7.62 (2H, d, J=9.2 Hz), 6.96 (2H, d, J=9.2 Hz), 6.70 (2H, slbrs), 6.41 (1H, s), 3.77 (3H, s).

EXAMPLE 79

4-(3-Bromoanilino)-6-(piperidin-1-yl)pyrido[3,4-d]pyrimidide

Treatment of 4-(3-bromoanilino)-6-fluoropyrido[3,4-d]pyrimidine (see a previous experimental) at 100° C. in a pressure vessel with piperidine in ethanol gives 4-(3-bromoanilino)-6-dimethylaminopyrido[3,4-d]pyrimidine.

The pharmaceutical compositions of the invention can take any of a wide variety of oral and parenteral dosage forms. The dosage forms comprise as the active components an inhibitor as defined previously.

For preparing pharmaceutical compositions, one uses inert, pharmaceutically acceptable carriers that can be either solid or liquid. Solid form preparations include powders, tablets, dispersible granules, capsules, cachets, and suppositories. A solid carrier can be one or more substances which may also act as dilutents, flavoring agents, solubilizers, lubricants, suspending agents, binders, or tablet disintegrating agents; it can also be an encapsulating material. In powders, the carrier is a finely divided solid which is in admixture with the finely divided active compounds. In the tablet, the active compounds are mixed with carrier having the necessary binding properties in suitable proportions and compacted in the shape and size desired. The powders and tablets preferably contain from 5% or 10% to about 70% of active ingredients. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compounds with encapsulating materials as carrier, providing a capsule in which the active components (with or without other carriers) are surrounded by carrier, which are thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active components in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation may be subdivided into unit doses containing appropriate quantities of inhibitor and other anti-cancer materials individually or as a combination, i.e., in a mixture. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form. Additionally, the unit dosage form may be a dividable form having an inhibitor in one part and other anti-cancer materials in the other part, such as, a dividable capsule, a dividable package, or a two-part ampoule, vial or the like.

The quantity of an inhibitor in unit dosages of preparation may be varied or adjusted from about 0.01 mg/kg to 100.0 mg/kg, preferably 0.03 mg/kg to less than 1.0 mg/kg of inhibitor.

The pharmaceutical compositions preferably are constituted so that they can be administered parenterally or orally. Solutions of the active compounds as free bases and free acids or pharmaceutically acceptable salts can be prepared in water suitable mixed with a surfactant such as hydroxypropylcellulose. Dispersions can also be prepared in glycerol, liquid polyethylene glycols, and mixtures thereof and in oils. Under ordinary conditions of stomge and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and stomge and must be preserved against the contaminating action of the microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion, and by the use of surfactants. The prevention of the action of microorganisms can be brought about by various antibacterial and antifungal agents, for example, pamgens, chlorobutanol, phenol, sorbic acid, thimerosal, and the like. In many cases, it will be preferred to include isotonic agents, for example, sugars or sodium chloride. Prolonged absorption of the injectable compositions of agents delaying absorption, for example, gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients, into a sterile vehicle which contains the basic dispersion medium and the required other ingredients from those enumerated above. In the case of the sterile powders for the preparation of sterile injectable solutions, the preferred methods of preparation are vacuum drying and the freeze-drying technique which yields a powder of active ingredients plus an additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suitable as unitary dosages for the mammalian subjects to be treated; each unit containing a predetermined quantity of active materials calculated to produce the desired therapeutic effect in association with the required pharmaceutical carrier. The specification for the novel dosage unit forms of the invention are dictated by and directly dependent on (a) the unique characteristics of the active materials and the particular therapeutic effect to be achieved, and (b) the limitation inherent in the art of compounding such active materials for the treatment of disease in living subjects having a diseased condition in which bodily health is impaired as herein disclosed in detail.

The principal active ingredients are compounded for convenient and effective administration in effective amounts with a suitable pharmaceutically acceptable carrier in dosage unit form as hereinbefore disclosed. A unit parenteral dosage form can, for example, contain the principal active compound, i.e. an inhibitor, in amounts ranging from about 0.5 to about 100 mg, with from about 0.1 to 50 mg being preferred. The daily parenteral doses for mammalian subjects to be treated ranges from 0.01 mg/kg to 10 mg/kg of the inhibitor. The preferred daily dosage range is 0.1 mg/kg to 1.0 mg/kg.

For oral dosages, the daily amount may range from 0.01 mg of active compound/kg of mammalian subject to 100 mg/kg, preferably 0.1 to 10 mg/kg of subject.

The inhibitor described above may form commonly known, pharmaceutically acceptable salts such as alkali metal and other common basic salts or acid addition salts, etc. References to the base substances are therefore intended to include those common salts known to be substantially equivalent to the parent compound and hydrates thereof.

The active compounds described herein are capable of further forming both pharmaceutically acceptable acid addition and/or base salts. All of these forms are within the scope of the present invention.

Pharmaceutically acceptable acid addition salts of the active compounds include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono-and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M. et al, "Pharmaceutical Salts", JOURNAL OF PHARMACEUTICAL SCIENCE, 66, pp. 1–19 (1977)).

The acid addition salts of said basic compounds are prepared by contacting the free base form with a sufficient amount of the desired acid to produce the salt in the conventional manner. Preferably, an active compound can be converted to an acidic salt by treating with an aqueous solution of the desired acid, such that the resulting pH is less than 4. The solution can be passed through a C18 cartridge to absorb the compound, washed with copious amounts of water, the compound eluted with a polar organic solvent such as, for example, methanol, acetonitrile, and the like, and isolated by concentrating under reduced pressure followed by lyophilization. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge, S. M. et al, "Pharmaceutical Salts", JOURNAL OF PHARMACEUTICAL SCIENCE, 66, pp. 1–19 (1977)).

The base addition salts of said acidic compounds are prepared by contacting the free acid form with a sufficient amount of the desired base to produce the salt in the conventional manner. Preferably, an active compound can be converted to a base salt by treating with an aqueous solution of the desired base, such that the resulting pH is greater than 9. The solution can be passed through a C18 cartridge to absorb the compound, washed with copious amounts of water, the compound eluted with a polar organic solvent such as, for example, methanol, acetonitrile and the like, and isolated by concentrating under reduced pressure followed by lyophilization. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acids for purposes of the present invention.

Certain of the compounds of the present invention can exist in unsolvated forms as well as solvated forms, including hydrated forms. In general, the solvated forms, including hydrated forms are equivalent to unsolvated forms and are intended to be encompassed within the scope of the present invention.

Certain of the compounds of the present invention possess one or more chiral centers and such center may exist in the R(D) or S(L) configuration. The present invention includes all enantiomeric and epimeric forms as well as the appropriate mixtures thereof.

While the forms of the invention herein constitute presently preferred embodiments, many others are possible. It is not intended herein to mention all of the possible equivalent forms or ramifications of the invention. It is understood that the terms used herein are merely descriptive rather than limiting and that various changes may be made without departing from the spirit or scope of the invention.

Scheme 1. Synthesis of Preferred Groups 1–5; $R^4$ = H

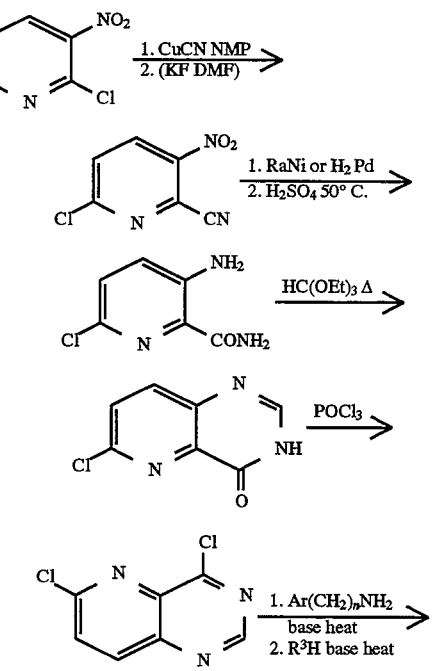

-continued
Scheme 1. Synthesis of Preferred Groups 1–5; $R^4$ = H
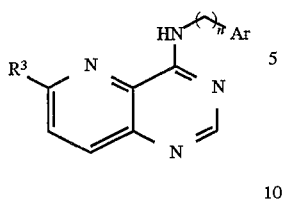
Scheme 2. Synthesis of Preferred Groups 1–5; $R^3$ = H
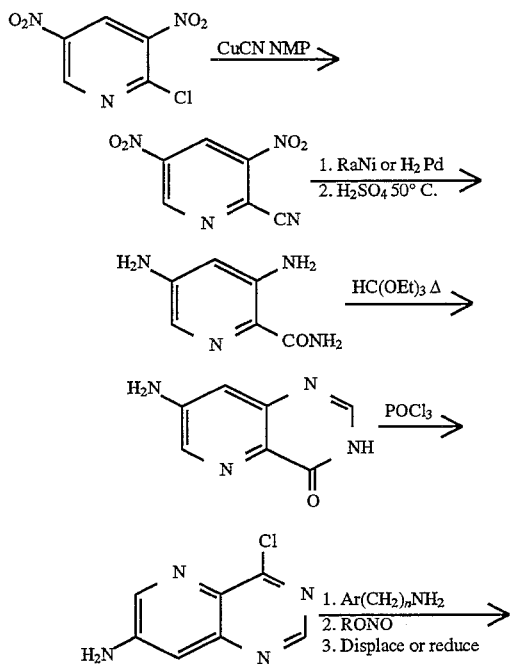
Scheme 3. Synthesis of Preferred Groups 6 and 8–10; $R^4$ = RO
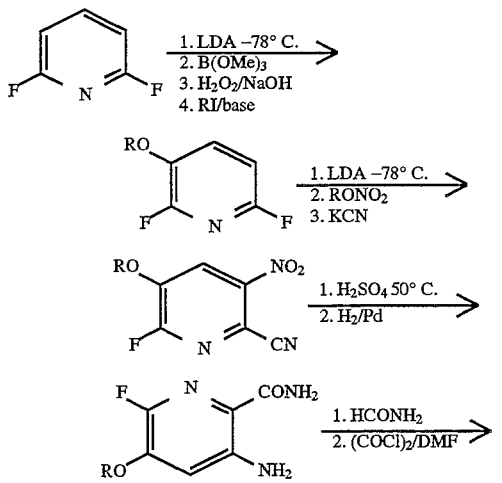
-continued
Scheme 3. Synthesis of Preferred Groups 6 and 8–10; $R^4$ = RO
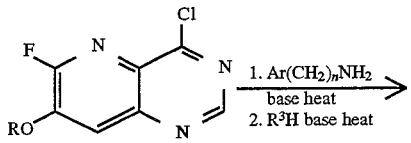
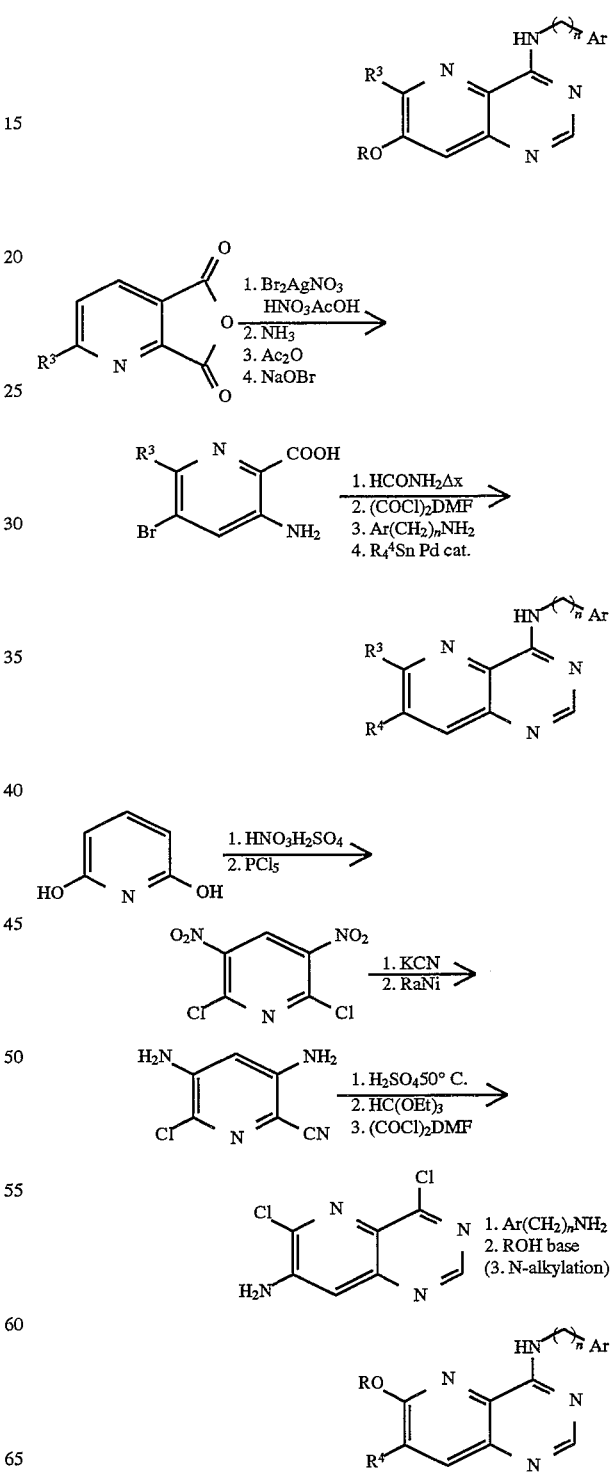

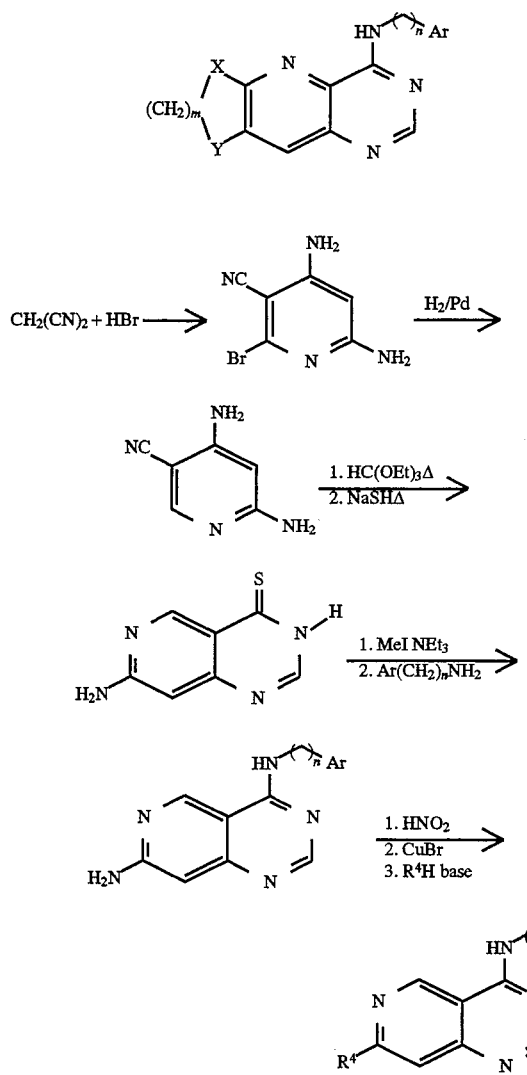
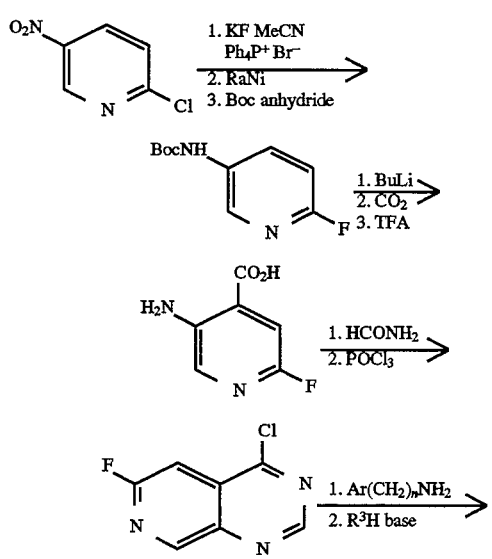
Scheme 8. Synthesis of Preferred Groups 17–21.
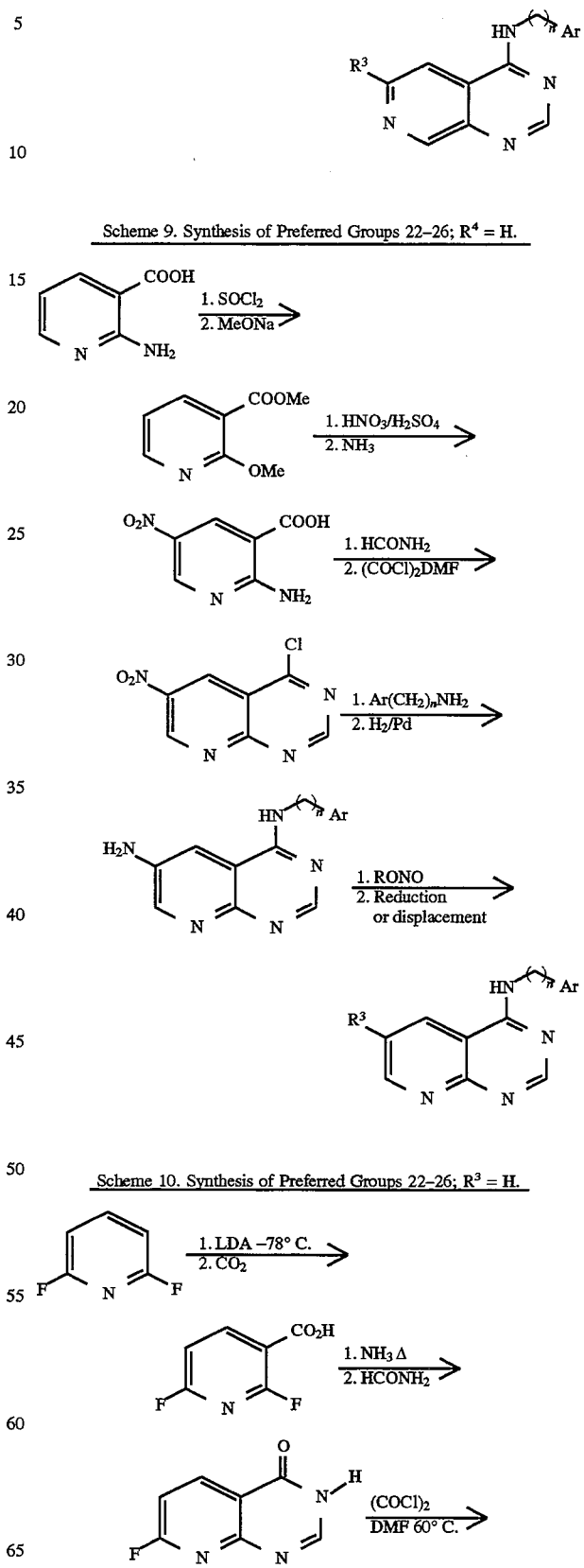
Scheme 9. Synthesis of Preferred Groups 22–26; $R^4$ = H.
Scheme 10. Synthesis of Preferred Groups 22–26; $R^3$ = H.
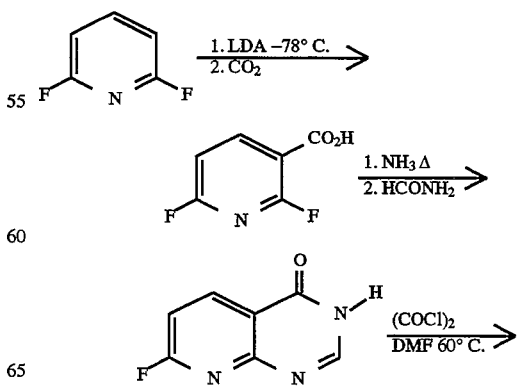

Scheme 10. Synthesis of Preferred Groups 22–26; $R^3$ = H.
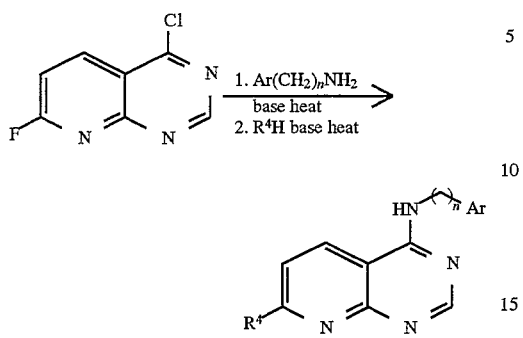
Scheme 11.
Synthesis of Preferred Groups 27 & 29–31; $R^3$ = RO
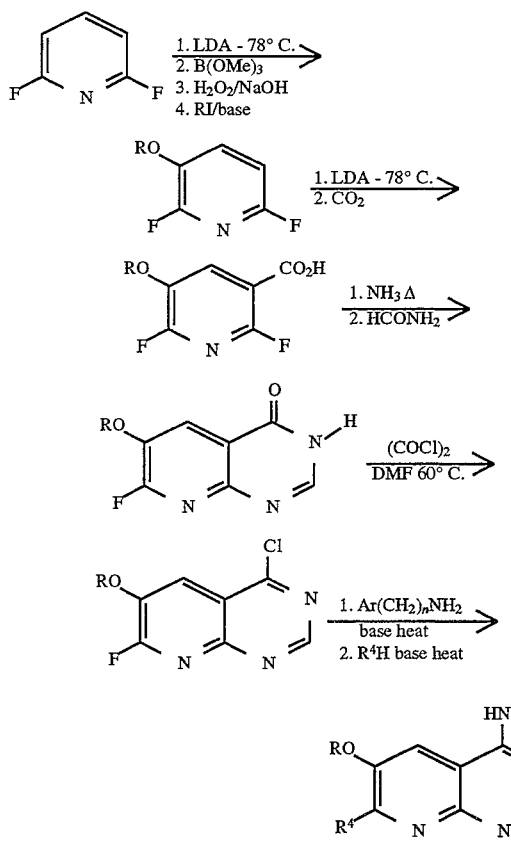
Scheme 12.
Synthesis of Preferred Groups 28
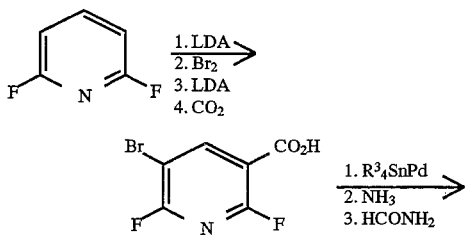
Scheme 12.
Synthesis of Preferred Groups 28
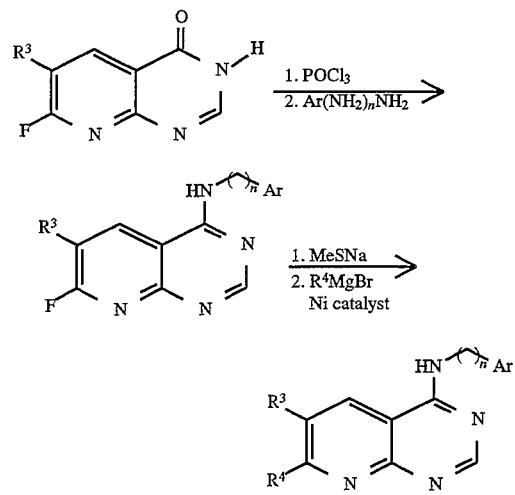
Scheme 13.
Synthesis of Preferred Groups 29 & 30; $R^4$ = OR
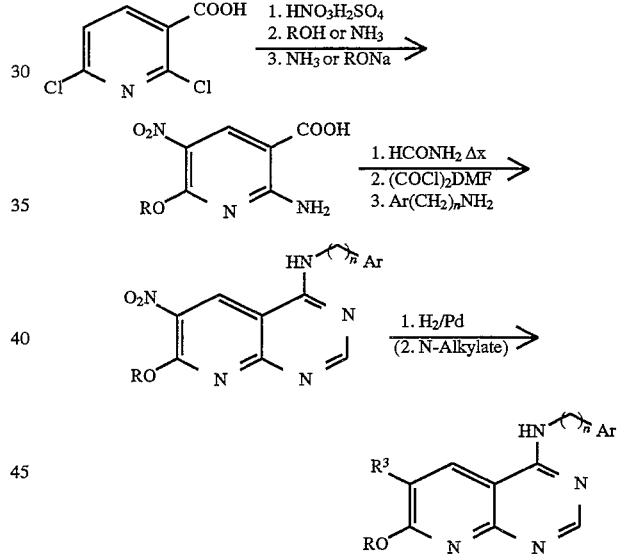
Scheme 14. Preferred Group 32.
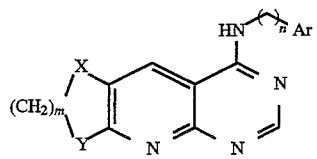
Scheme 15. Synthesis of Preferred Groups 33–36.
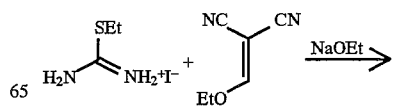

Scheme 15. Synthesis of Preferred Groups 33–36.
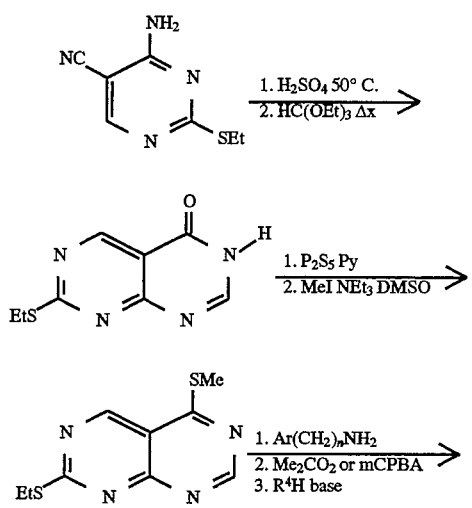
Scheme 16. Synthesis of Preferred Groups 37–40
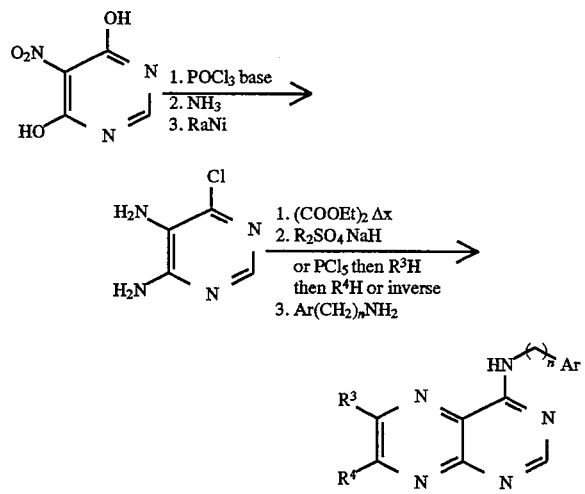
Scheme 17. Synthesis of Preferred Group 41; [3,2-d] ring fusion
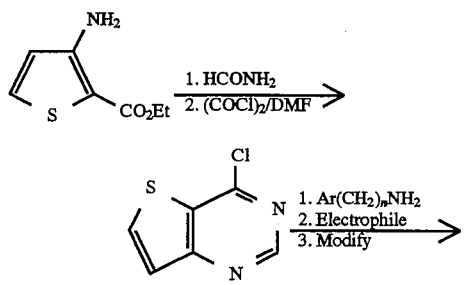
Scheme 17. Synthesis of Preferred Group 41; [3,2-d] ring fusion
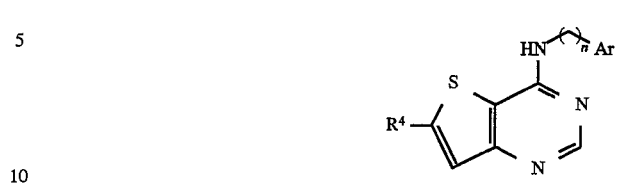
Scheme 18. Synthesis of Preferred Group 41; [2,3-d] ring fusion
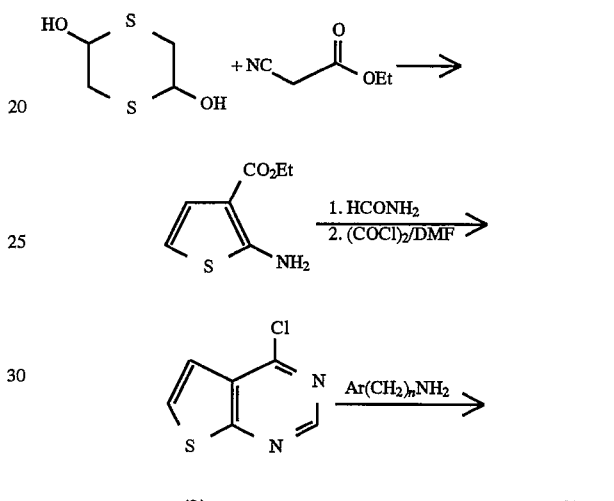
Scheme 19. Synthesis of Preferred Group 42; [3,2-d] ring fusion
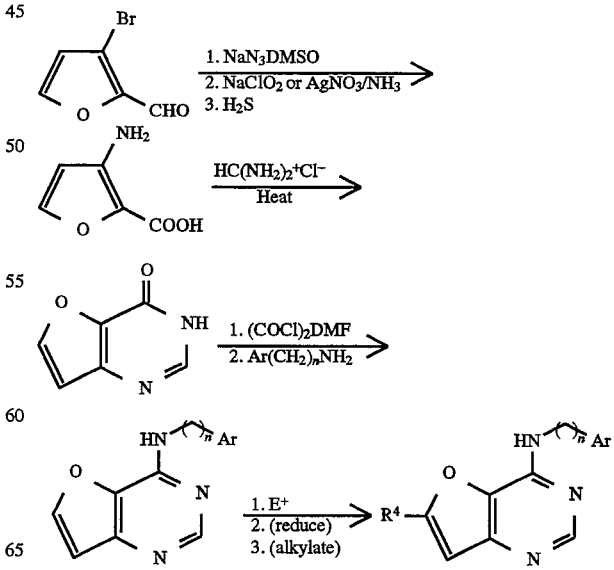

5,654,307

67

Scheme 20.
Synthesis of Preferred Group 42; [2,3-d] ring fusion

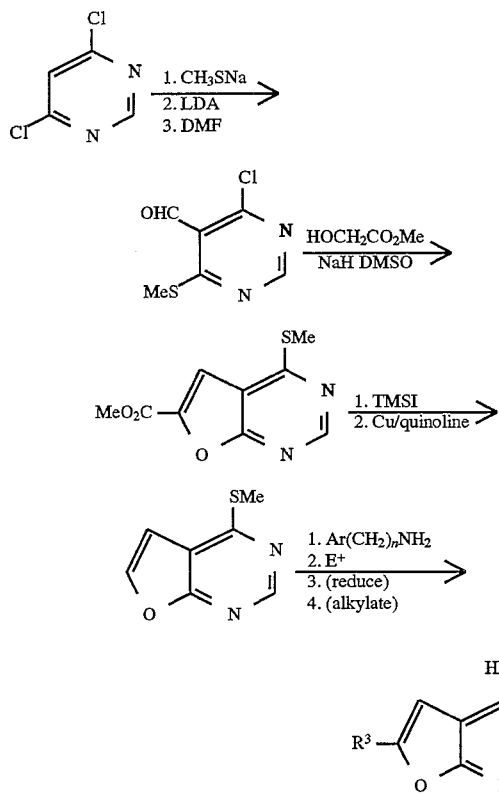

Scheme 21. Synthesis of Preferred Group 43; [2,3-d] ring fusion.

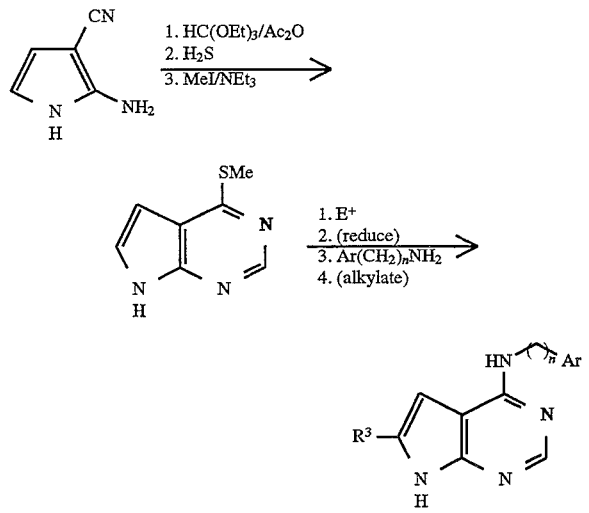

Scheme 22. Synthesis of Preferred Group 43; [2,3-d] ring fusion.

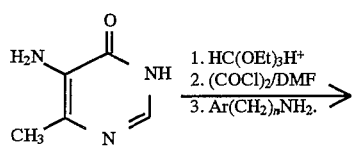

68

-continued

Scheme 22. Synthesis of Preferred Group 43; [2,3-d] ring fusion.

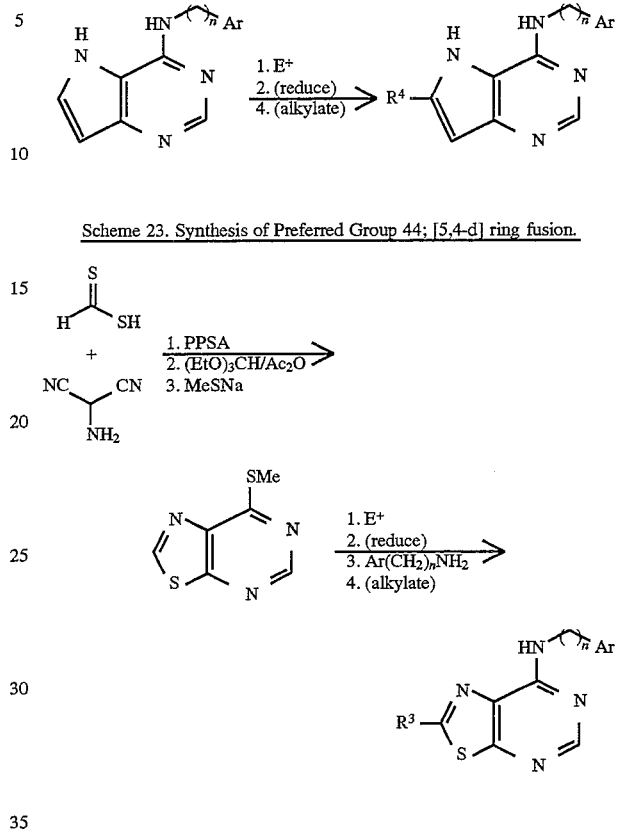

Scheme 23. Synthesis of Preferred Group 44; [5,4-d] ring fusion.

Scheme 24. Synthesis of Preferred Group 44; [4,5-d] ring fusion.

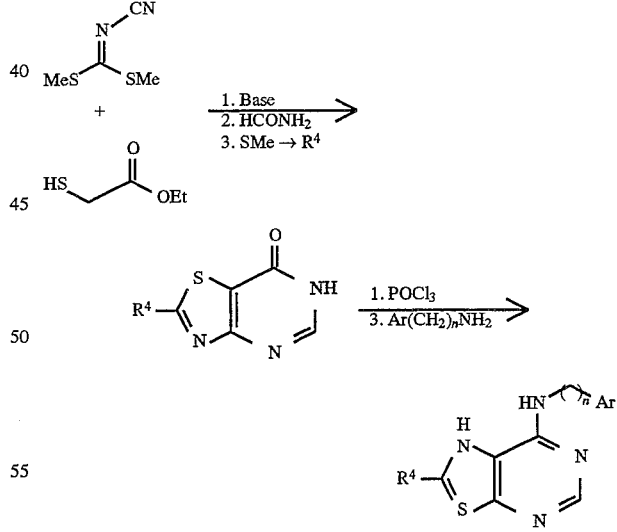

Scheme 25. Synthesis of Preferred Group 45; [5,4-d] ring fusion.

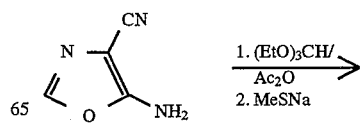

-continued
Scheme 25. Synthesis of Preferred Group 45; [5,4-d] ring fusion.

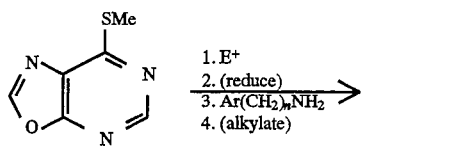

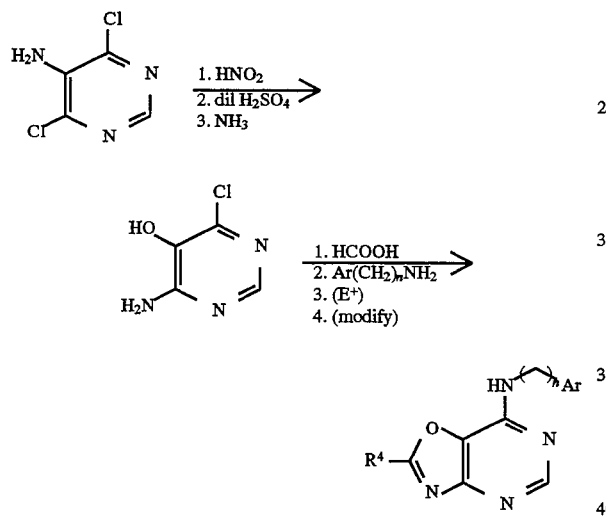

Scheme 27. Synthesis of Preferred Group 46.

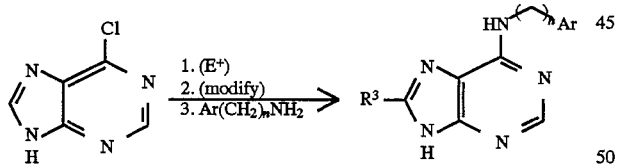

Scheme 28. Synthesis of Preferred Group 47; [5,4-d] ring fusion.

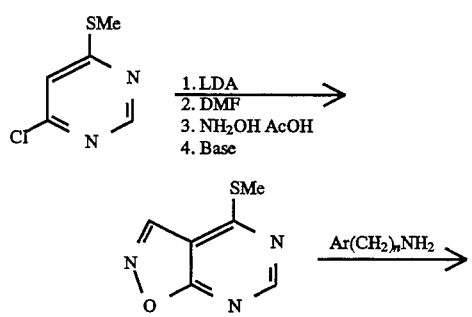

-continued
Scheme 28. Synthesis of Preferred Group 47; [5,4-d] ring fusion.

Scheme 29.
Synthesis of Preferred Group 47; [4,5-d]ring fusion.

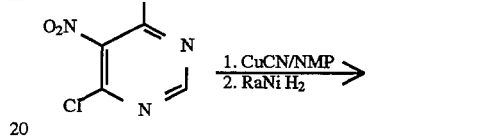

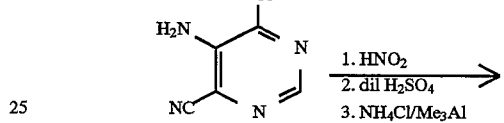

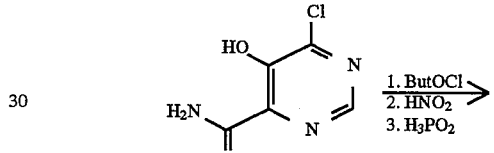

Scheme 30.
Synthesis of Preferred Group 48; [5,4-d]ring fusion.

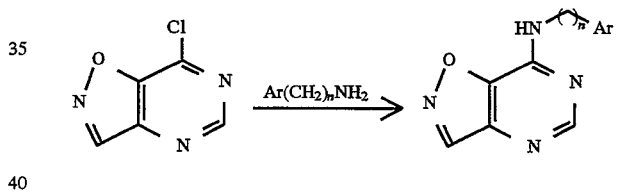

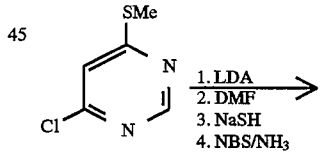

Scheme 31.
Synthesis of Preferred Group 48; [4,5-D]ring fusion.

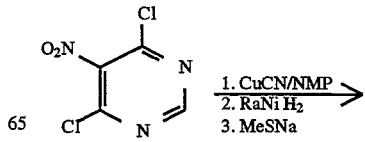

Scheme 31.
Synthesis of Preferred Group 48; [4,5-D]ring fusion.

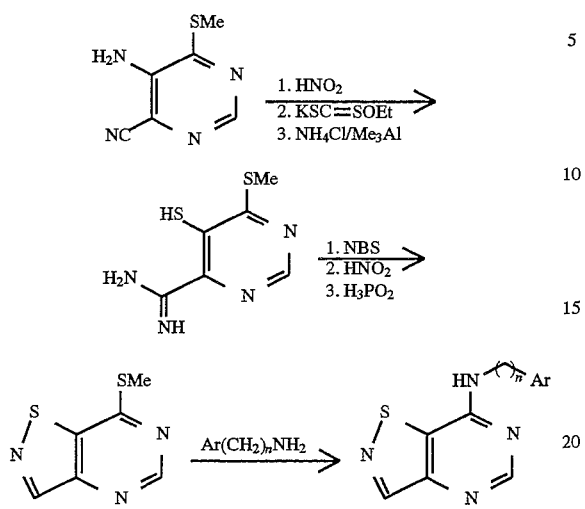

Scheme 32. Synthesis of Preferred Group 49; [3,4-d]ring fusion.

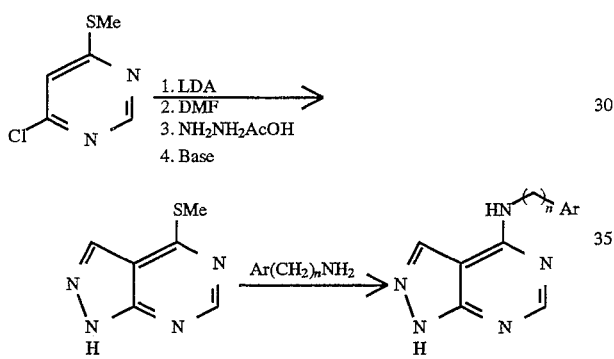

Scheme 33. Synthesis of Preferred Group 49; [4,3-d]ring fusion.

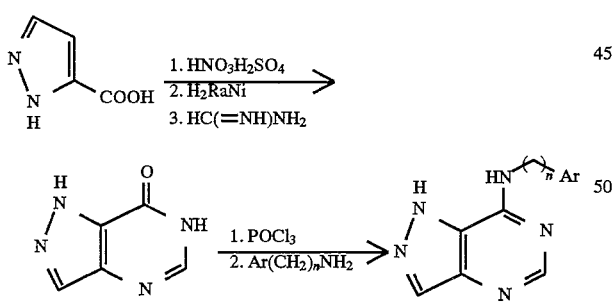

What is claimed is:

1. A compound of Formula Ia or Ib

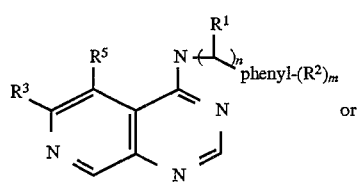

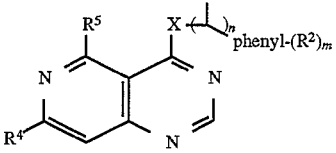

wherein X is NH or $NR^7$, wherein $R^7$ is selected from the group consisting of lower alkyl (1–4 carbon atoms), OH, $NH_2$, lower alkoxy (1–4 carbon atoms) and lower monoalkylamino (1–4 carbon atoms);

n is 0, 1 or 2;

$R^1$ is H or lower alkyl (1–4 carbon atoms); if n is 2, $R^1$ is independently H or lower alkyl (1–4 carbon atoms) on either linking carbon atom;

$R^2$ is selected from the group consisting of lower alkyl (1–4 carbon atoms), cycloalkyl (3–8 carbon atoms), lower alkoxy (1–4 carbon atoms), cycloalkoxy (3–8 carbon atoms), nitro, halo (fluoro, chloro, bromo, iodo), lower perfluoroalkyl (1–4 carbon atoms), hydroxy, lower acyloxy (1–4 carbon atoms; —O—C(O)—R), amino, lower mono or dialkylamino (1–4 carbon atoms), lower mono or dicycloalkylamino (3–8 carbon atoms), hydroxymethyl, lower acyl (1–4 carbon atoms; —C(O)R), cyano, lower thioalkyl (1–4 carbon atoms), lower sulfinylalkyl (1–4 carbon atoms), lower sulfonylalkyl (1–4 carbon atoms), thiocycioalkyl (3–8 carbon atoms), sulfinyicycloalkyl (3–8 carbon atoms), sulfonylcycloalkyl (3–8 carbon atoms), sulfonamido, lower mono or dialkylsulfonamido (1–4 carbon atoms), mono or dicycloalkylsulfonamido (3–8 carbon atoms), mercapto, carboxy, carboxamido (—C(O)—$NH_2$), lower mono or dialkylcarboxamido (1–4 carbon atoms), mono or dicycloalkoxycarboxamido (3–8 carbon atoms), lower alkoxycarbonyl (1–4 carbon atoms), cycloalkoxycarbonyl (3–8 carbon atoms), lower alkenyl (2–4 carbon atoms), cycloalkenyl (4–8 carbon atoms), lower alkynyl (2–4 carbon atoms), and two $R^2$ taken together on contiguous carbon atoms form a carbocyclic ring of 5–7 members or a monounsaturated ring selected from the group consisting of 1,3-dioxolanyl, 1,4-dioxanyl, 1,4-dioxepinyl, pyranyl, furanal, pyrrolidyl, piperidinyl, thiolanyl, oxazolanyl, thiazolanyl, diazolanyl, piperazinyl, morpholino and thiomorpholino;

m=0–3; and $R^3$, $R^4$, and $R^5$ are independently selected from the group consisting of H, lower alkyl (1–4 carbon atoms), cycloalkyl (3–8 carbon atoms), lower alkoxy (1–4 carbon atoms), cycloalkoxy (3–8 carbon atoms), hydroxy, lower acyloxy (1–4 carbon atoms), amino, lower mono or dialkylamino (1–4 carbon atoms), lower mono or dicycloalkylamino (3–8 carbon atoms), carbonato (—OC(O)OR) where the R is lower alkyl of 1 to 4 carbon atoms or cycloalkyl of 3–8 carbon atoms; ureido or thioureido or N- or O-linked urethane any one of which is optionally substituted by mono or di-lower alkyl (1–4 carbon atoms) or cycloalkyl (3–8 carbon atoms);

lower thioalkyl (1–4 carbon atoms), thiocycloalkyl (3–8 carbon atoms), mercapto, lower alkenyl (2–4 carbon atoms), hydrazino, N'-lower alkylhydrazino (1–4 carbon atoms), lower acylamino (1–4 carbon atoms), hydroxylamino, and lower O-alkylhydroxylamino (1–4 carbon atoms);

or optionally $R^3$ and $R^5$ taken together on contiguous carbon atoms form a carbocyclic ring of 5–7 members or a monounsaturated ring selected from the group consisting of 1,3-dioxolanyl, 1,4-dioxanyl, 1,4-dioxepinyl, pyranyl, furanyl, pyrrolidyl, piperidinyl, thiolanyl, oxazolanyl, thiazolanyl, diazolanyl, piperazinyl, morpholino and thiomorpholino;

any lower alkyl group substituent on any of the substituents in $R^3$–$R^5$ which moiety is optionally substituted with one or more groups selected from the group consisting of hydroxy, amino, lower monoalkylamino, lower dialkylamino, N-pyrrolidyl, N-piperidinyl, N-pyridinium, N-morpholino, N-thiomorpholino and N-piperazino;

with the proviso that $R^3$–$R^5$ on a neighboring C atom to one of the N atoms, cannot be either OH or SH;

with the further proviso that at least one of the group $R^3$ and $R^5$ or $R^4$ and $R^5$ substituents must be other than hydrogen, lower alkyl (1–4 carbon atoms), or lower alkoxy (1–4 carbon atoms);

optionally if any of the substituents $R^1$, $R^2$, $R^3$, $R^4$, $R^5$ have chiral centers, then all stereoisomers thereof both separately and as racemic and/or diastereoisomeric mixtures are included;

or a pharmaceutical salt or hydrate thereof.

2. The compound of claim 1 wherein the compound is selected from the group consisting of:

7-Amino-4-(3-nitroanilino)pyrido[4,3-d]pyrimidine;

7-Amino-4-(3-bromoanilino)pyrido[4,3-d]pyrimidine;

7-Amino-4-(4-bromoanilino)pyrido[4,3-d]pyrimidine;

7-Amino-4-(3-trifluoromethylanilino)pyrido[4,3-d]pyrimidine;

7-Acetylamino-4-(3-bromoanilino)pyrido[4,3-d]pyrimidine;

7-Acetamido-4-benzylaminopyrido[4,3-d]pyrimidine;

4-(3-Bromoanilino)-6-methylaminopyrido[3,4-d]pyrimidine;

and 4-(3-Bromoanilino)-6-dimethylaminopyrido[3,4-d]pyrimidine.

* * * * *

UNITED STATES PATENT AND TRADEMARK OFFICE
CERTIFICATE OF CORRECTION

PATENT NO.   : 5,654,307
DATED        : August 5, 1997
INVENTOR(S)  : Alexander James Bridges, et al It is certified that error appears in the above-identified patent and that said Letters Patent is hereby corrected as shown below:

Abstract, line 3, delete "kinase" and insert --kinases--.

Column 71, in Claim 1, the structure should read as follows:

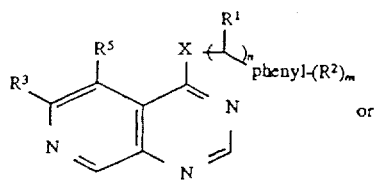

Column 72, line 29, delete "sulfinyicycloalkyl" and insert --sulfinylcycloalkyl--

Signed and Sealed this

Twelfth Day of January, 1999

Attest:

*Attesting Officer*       Acting Commissioner of Patents and Trademarks